United States Patent
Kato et al.

(10) Patent No.: US 9,757,462 B2
(45) Date of Patent: Sep. 12, 2017

(54) COMBINED PHARMACEUTICAL PREPARATION

(75) Inventors: Junji Kato, Hokkaido (JP); Rishu Takimoto, Hokkaido (JP)

(73) Assignee: Sapporo Medical University, Sapporo-shi, Hokkaido (JP)

( * ) Notice: Subject to any disclaimer, the term of this patent is extended or adjusted under 35 U.S.C. 154(b) by 460 days.

(21) Appl. No.: 13/885,811

(22) PCT Filed: Oct. 20, 2011

(86) PCT No.: PCT/JP2011/074221
§ 371 (c)(1),
(2), (4) Date: Jul. 30, 2013

(87) PCT Pub. No.: WO2012/066896
PCT Pub. Date: May 24, 2012

(65) Prior Publication Data
US 2014/0030186 A1   Jan. 30, 2014

(30) Foreign Application Priority Data

Nov. 19, 2010 (JP) ................. 2010-259311

(51) Int. Cl.
A61K 47/26 (2006.01)
A61K 47/48 (2006.01)

(52) U.S. Cl.
CPC ........ A61K 47/26 (2013.01); A61K 47/48092 (2013.01); A61K 47/48815 (2013.01)

(58) Field of Classification Search
CPC ........ A61K 47/48092; A61K 47/48815; A61K 47/26
See application file for complete search history.

(56) References Cited

U.S. PATENT DOCUMENTS

| | | | |
|---|---|---|---|
| 5,043,107 A | 8/1991 | Adler-Moore et al. | |
| 5,435,989 A | 7/1995 | Presant et al. | |
| 2006/0193906 A1 | 8/2006 | Yamazaki et al. | |
| 2007/0292494 A1* | 12/2007 | Gieseler | A61K 47/48815 424/450 |

FOREIGN PATENT DOCUMENTS

| | | |
|---|---|---|
| EP | 1655022 A1 | 5/2006 |
| JP | 61-158932 A | 7/1986 |
| JP | 63-66123 A | 3/1988 |
| JP | H01-221400 A | 9/1989 |
| JP | H05-194278 | 8/1993 |
| JP | H08-151335 | 6/1996 |
| JP | H08/310971 | 11/1996 |
| JP | 2002-308802 | 10/2002 |
| JP | 2004-522722 A | 7/2004 |
| JP | 2007-112768 | 5/2007 |
| JP | 2009-46441 A | 3/2009 |
| JP | 2010-235564 A | 10/2010 |
| WO | WO 2004/069284 A2 | 8/2004 |
| WO | WO 2005/092288 A1 | 10/2005 |
| WO | WO 2005/120587 A1 | 12/2005 |
| WO | WO 2007/091661 A1 | 8/2007 |

OTHER PUBLICATIONS

Biessen et al., Lysine-based cluster mannosides that inhibit ligand binding to the human mannose receptor at nanomolar concentration. J Biol Chem. Nov. 8, 1996;271(45):28024-30. Abstract only.
Chigurupati et al., Involvement of notch signaling in wound healing. PLoS One. Nov. 14, 2007;2(11):e1167. Abstract only.
Dhara, A rapid method for the synthesis of cis-[Pt (NH3) 2Cl2]. Indian J. Chem. Feb. 1970;8:193-194.
Gabius, Targeting of Neoglycoprotein-Drug Conjugates to Human Tumor Cells via Endogenous Lectins. Annals of the New York Academy of Sciences. 1987;507:337-338.
Ghosh et al., Grafting of different glycosides on the surface of liposomes and its effect on the tissue distribution of 125I-labelled gamma-globulin encapsulated in liposomes. Biochim Biophys Acta. Nov. 3, 1980;632(4):562-72. Abstract only.
Higuchi et al., Uptake characteristics of mannosylated and fucosylated bovine serum albumin in primary cultured rat sinusoidal endothelial cells and Kupffer cells. Int J Pharm. Dec. 9, 2004;287(1-2):147-54. Abstract only.
Hirai et al., Accumulation of liposome with Sialyl Lewis X to inflammation and tumor region: application to in vivo bio-imaging. Biochem Biophys Res Commun. Feb. 16, 2007;353(3):553-8. Epub Dec. 19, 2006. Abstract only.
Hirai et al., Novel and simple loading procedure of cisplatin into liposomes and targeting tumor endothelial cells. Int J Pharm. May 31, 2010;391(1-2):274-83. doi: 10.1016/j.ijpharm.2010.02.030. Epub Mar. 6, 2010. Abstract only.
Kawakami et al., Biodistribution characteristics of mannosylated, fucosylated, and galactosylated liposomes in mice. Biochim Biophys Acta. Dec. 15, 2000;1524(2-3):258-65.
Kerrigan et al., C-type lectins and phagocytosis. Immunobiology. Jul. 2009;214(7):562-75. doi: 10.1016/j.imbio.2008.11.003. Epub Mar. 3, 2009. Abstract only.
Lecchi et al., Instrumentation and probes for molecular and cellular imaging. Q J Nucl Med Mol Imaging. Jun. 2007;51(2):111-26. Abstract only.

(Continued)

Primary Examiner — Robert Cabral
(74) Attorney, Agent, or Firm — Wolf, Greenfield & Sacks, P.C.

(57) ABSTRACT

The invention relates to a combined pharmaceutical composition or pharmaceutical preparation, comprising a first component containing a first ligand for a polyspecific lectin in a reticuloendothelial cell and a second component containing a carrier, a labeling agent, or a medicament for treating a disease associated with a target cell, each of which is targeted by a second ligand for a polyspecific lectin in a reticuloendothelial cell different from the first ligand, and also relates to a method for labeling a target cell and a method for treating a disease associated with a target cell, each using the same.

19 Claims, 34 Drawing Sheets

(56) References Cited

OTHER PUBLICATIONS

Lee et al., 2-Imino-2-methoxyethyl 1-thioglycosides: new reagents for attaching sugars to proteins. Biochemistry. Sep. 7, 1976;15(18):3956-63. Abstract only.

Lee et al., Preparation and some biochemical properties of neoglycoproteins produced by reductive amination of thioglycosides containing an omega-aldehydoaglycon. Biochemistry. Jan. 8, 1980;19(1):156-63.

Lehrman et al., The binding of fucose-containing glycoproteins by hepatic lectins. The binding specificity of the rat liver fucose lectin. J Biol Chem. Jun. 5, 1986;261(16):7426-32. Abstract only.

Ma et al., Fucosylation in prokaryotes and eukaryotes. Glycobiology. Dec. 2006;16(12):158R-184R. Epub Sep. 14, 2006.

Mas et al., Fucosyltransferase activities in human pancreatic tissue: comparative study between cancer tissues and established tumoral cell lines. Glycobiology. Jun. 1998;8(6):605-13.

Négre et al., Antileishmanial drug targeting through glycosylated polymers specifically internalized by macrophage membrane lectins. Antimicrob Agents Chemother. Oct. 1992;36(10):2228-32. Abstract only.

Reddy et al., Contrast-enhanced endoscopic ultrasonography. World J Gastroenterol. Jan. 7, 2011;17(1):42-8. doi:10.3748/wjg.v17.i1.42. Abstract only.

Sato et al., Resolution of liver cirrhosis using vitamin A-coupled liposomes to deliver siRNA against a collagen-specific chaperone. Nat Biotechnol. Apr. 2008;26(4):431-42. doi: 10.1038/nbt1396. Epub Mar. 30, 2008.

Seymour, Soluble polymers for lectin-mediated drug targeting. Advanced Drug Delivery Reviews. Apr.-May 1994;14(1):89-111.

Takahashi et al., Distribution of murine mannose receptor expression from early embryogenesis through to adulthood. Cell Tissue Res. May 1998;292(2):311-23. Abstract only.

Taylor et al., Contribution to ligand binding by multiple carbohydrate-recognition domains in the macrophage mannose receptor. J Biol Chem. Jan. 25, 1992;267(3):1719-26. Abstract only.

Uccini et al., Kaposi's sarcoma cells express the macrophage-associated antigen mannose receptor and develop in peripheral blood cultures of Kaposi's sarcoma patients. Am J Pathol. Mar. 1997;150(3):929-38. Abstract only.

Vansteenkiste et al., Fate of glycosylated dextrans after in vivo administration. J Control Release. 1991;16:91-100.

Yamazaki et al., Neoglycoprotein-liposome and lectin-liposome conjugates as tools for carbohydrate recognition research. Methods Enzymol. 1994;242:56-65.

Yamazaki, Analysis of the carbohydrate-binding specificity of lectin-conjugated lipid vesicles which interact with polysaccharide fragments. J Membrane Sci. 1989;41:249-267.

Zelensky et al., The C-type lectin-like domain superfamily. FEBS J. Dec. 2005;272(24):6179-217. Abstract only.

Higuchi et al., The potential role of fucosylated cationic liposome/NFkappaB decoy complexes in the treatment of cytokine-related liver disease. Biomaterials. Jan. 2007;28(3):532-9. Epub Sep. 18, 2006.

Higuchi et al., Intravenous administration of mannosylated cationic liposome/NFkappaB decoy complexes effectively prevent LPS-induced cytokine production in a murine liver failure model. FEBS Lett. Jun. 26, 2006;580(15):3706-14.

Yoshida et al., Targeting anticancer drug delivery to pancreatic cancer cells using a fucose-bound nanoparticle approach. PLoS One. 2012;7(7):e39545. doi:10.1371/journal.pone.0039545. Epub Jul. 11, 2012.

\* cited by examiner

[Fig. 1]
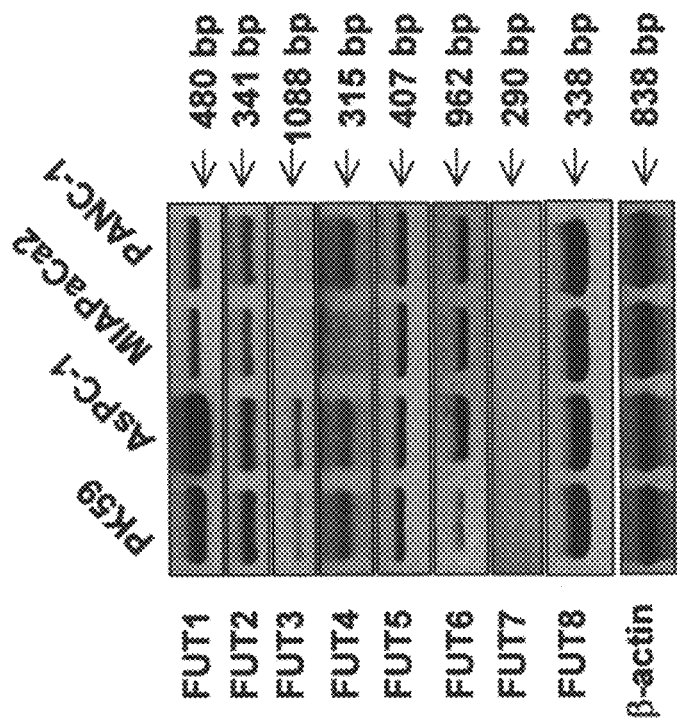
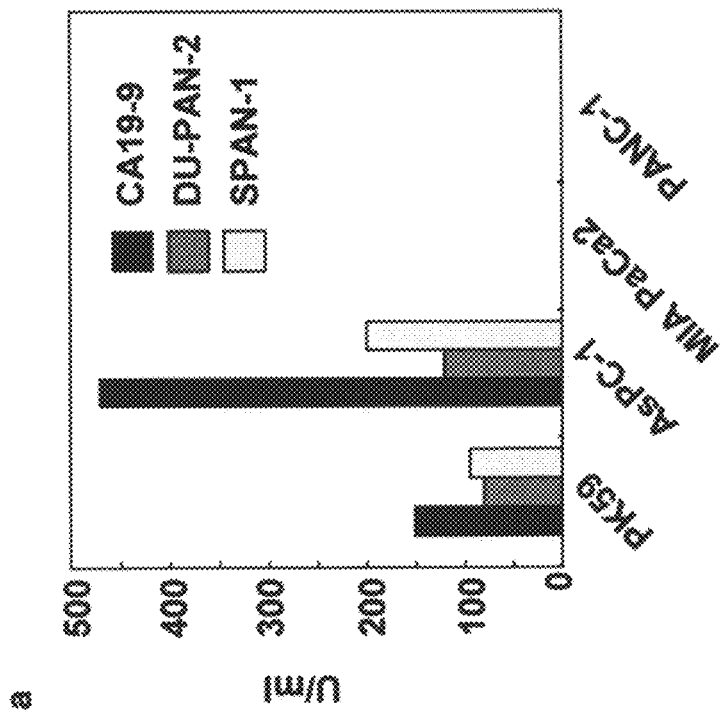

[Fig. 2]
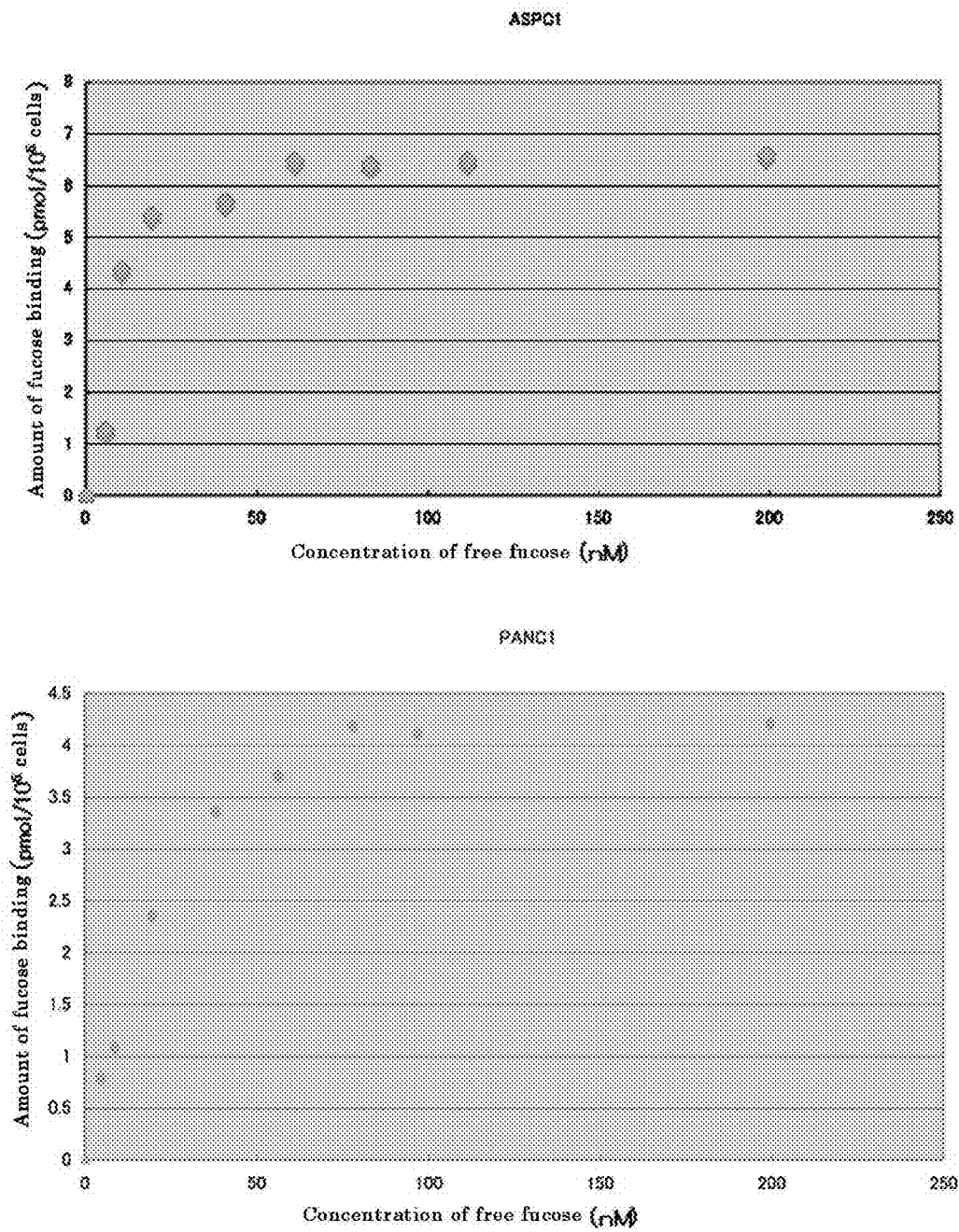

[Fig. 3]
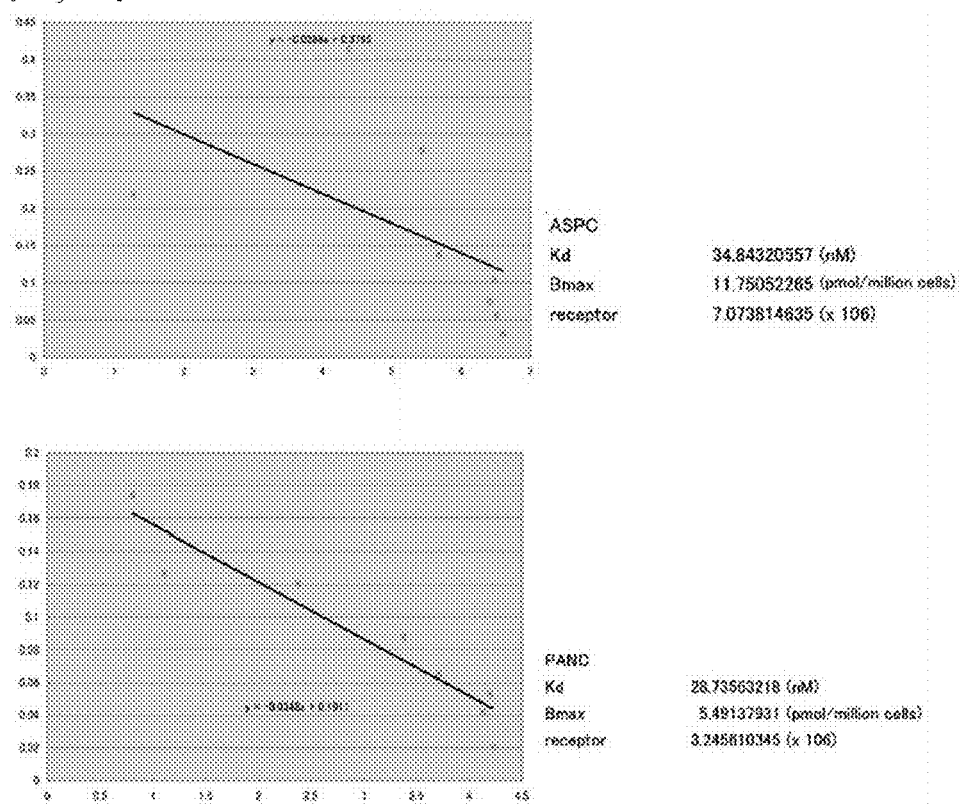
[Fig. 4]
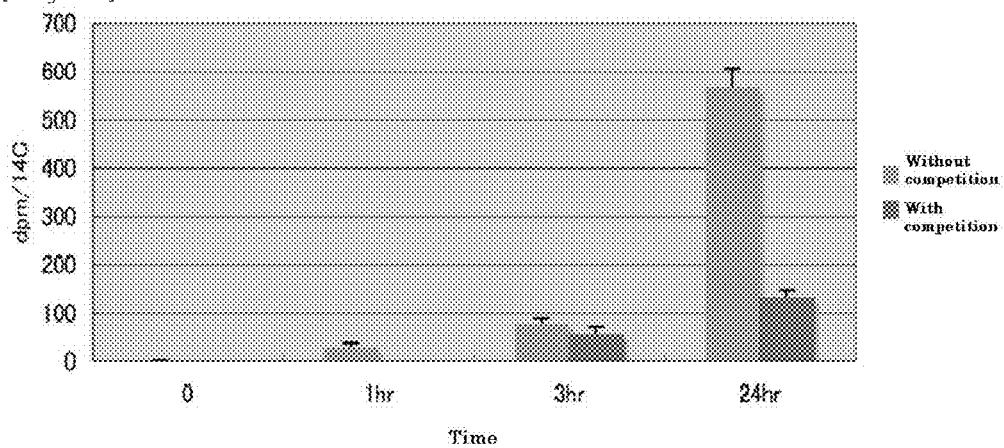

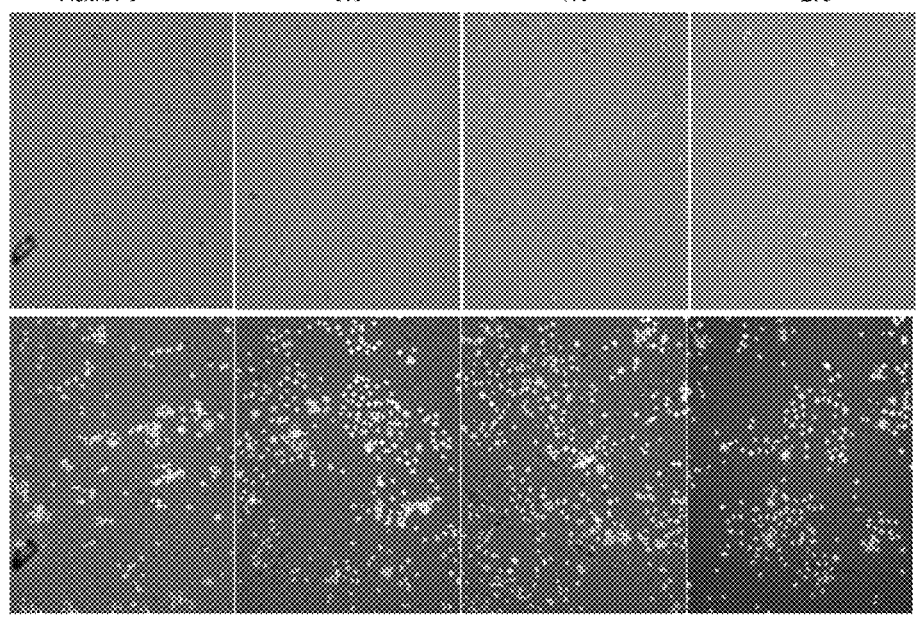
[Fig. 5]
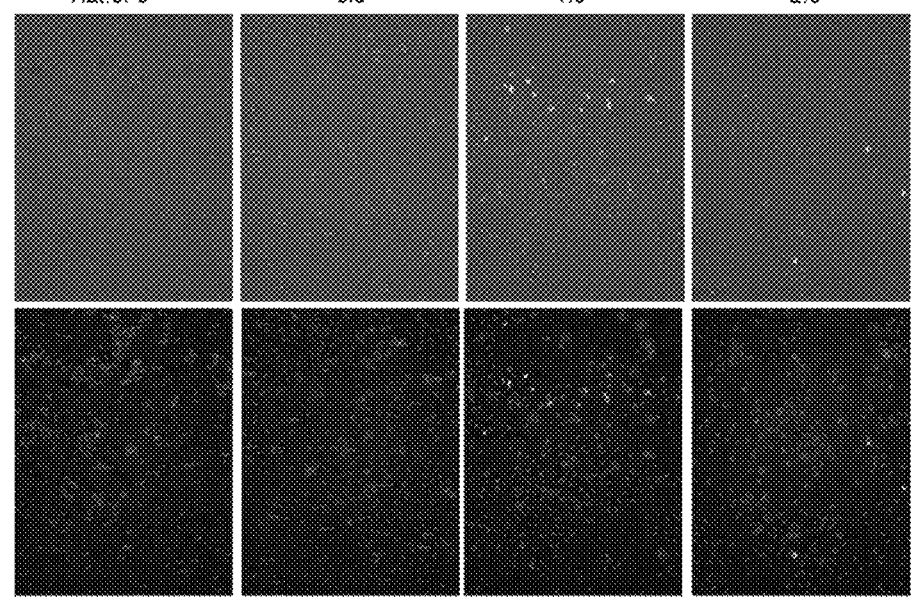
[Fig. 6]

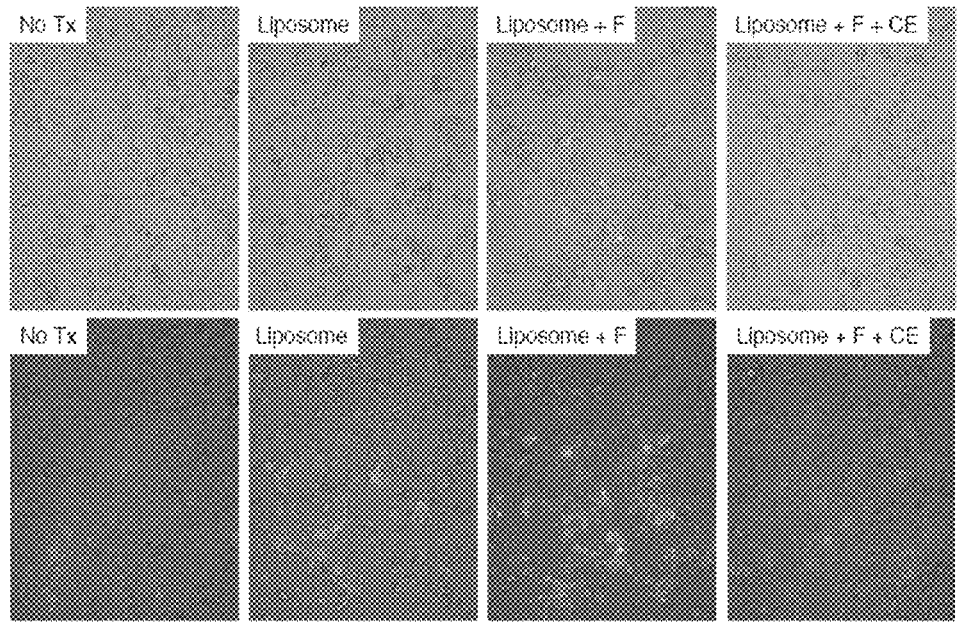
[Fig. 7]
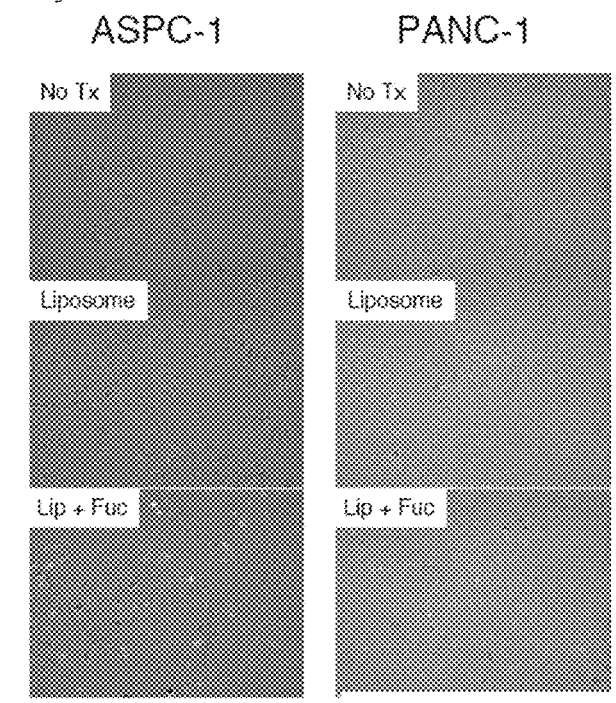
[Fig. 8]

[Fig. 9]
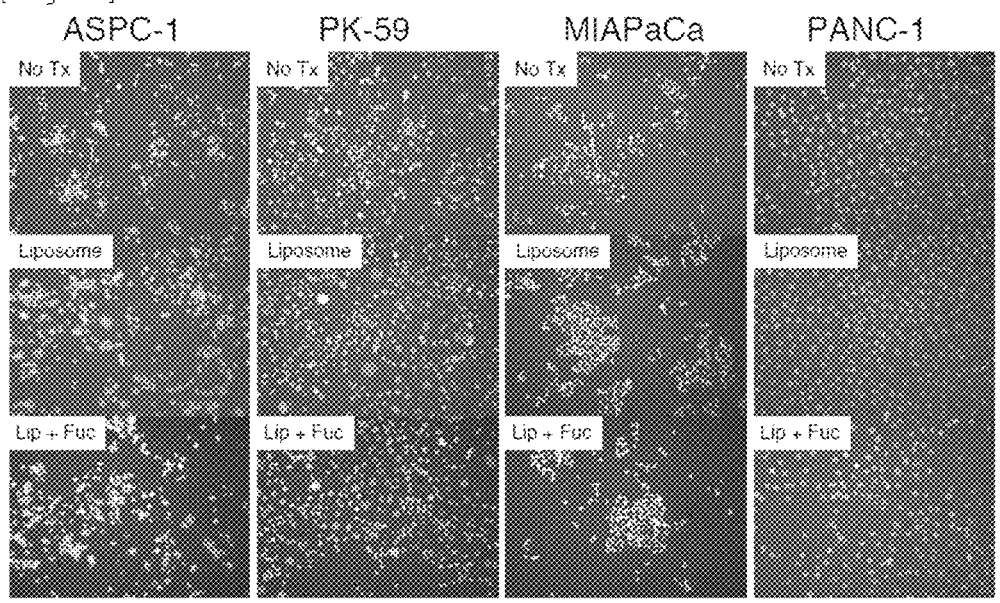
[Fig. 10]
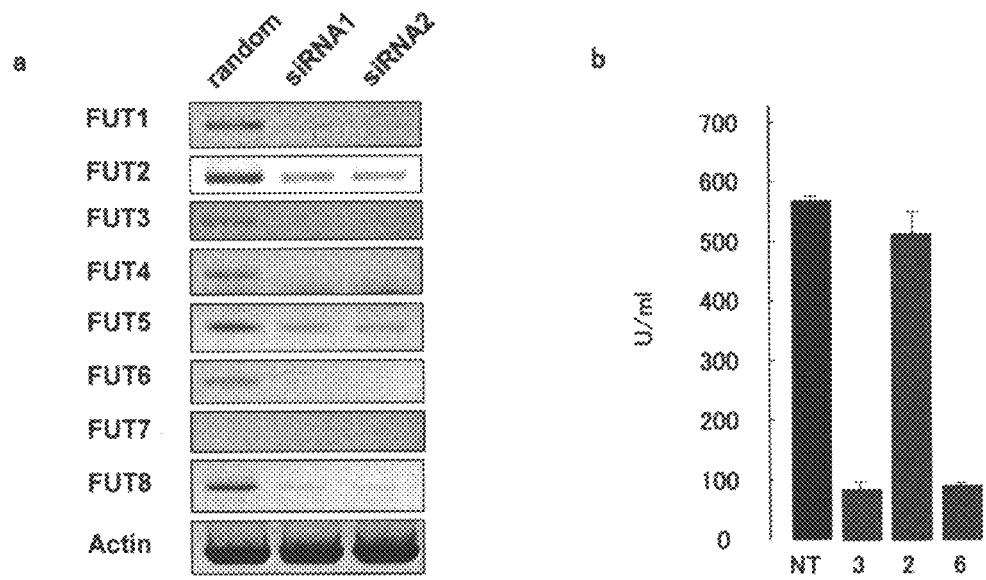

[Fig. 11]
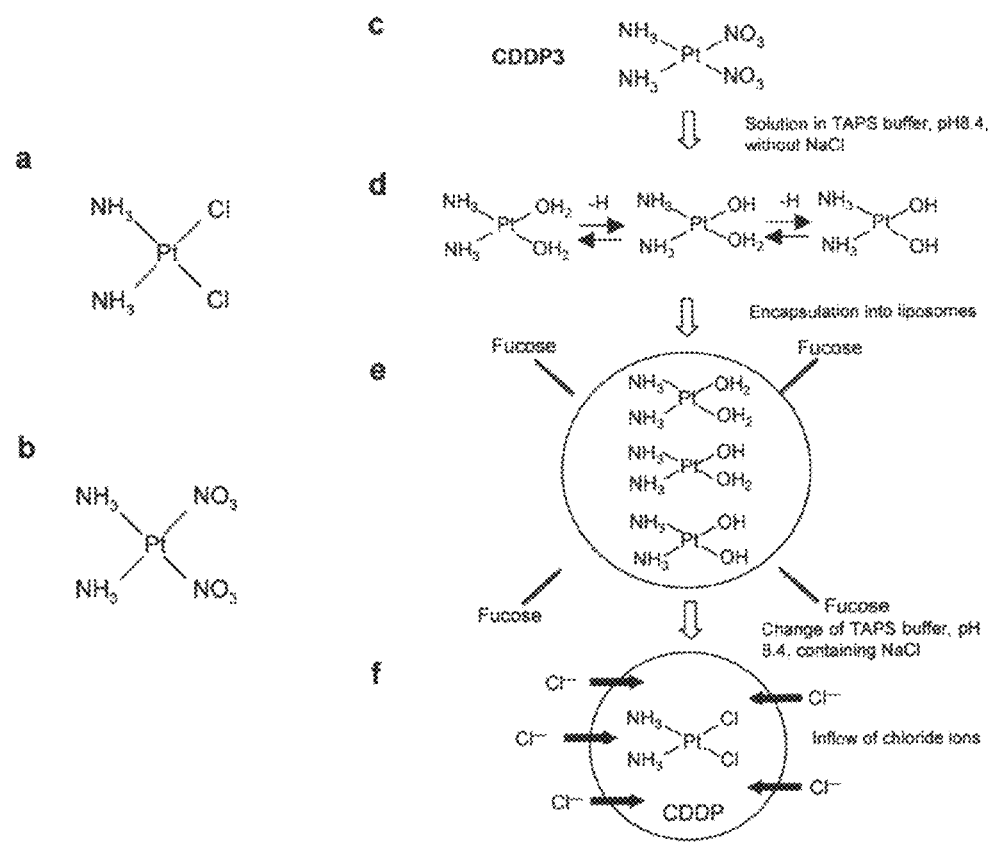

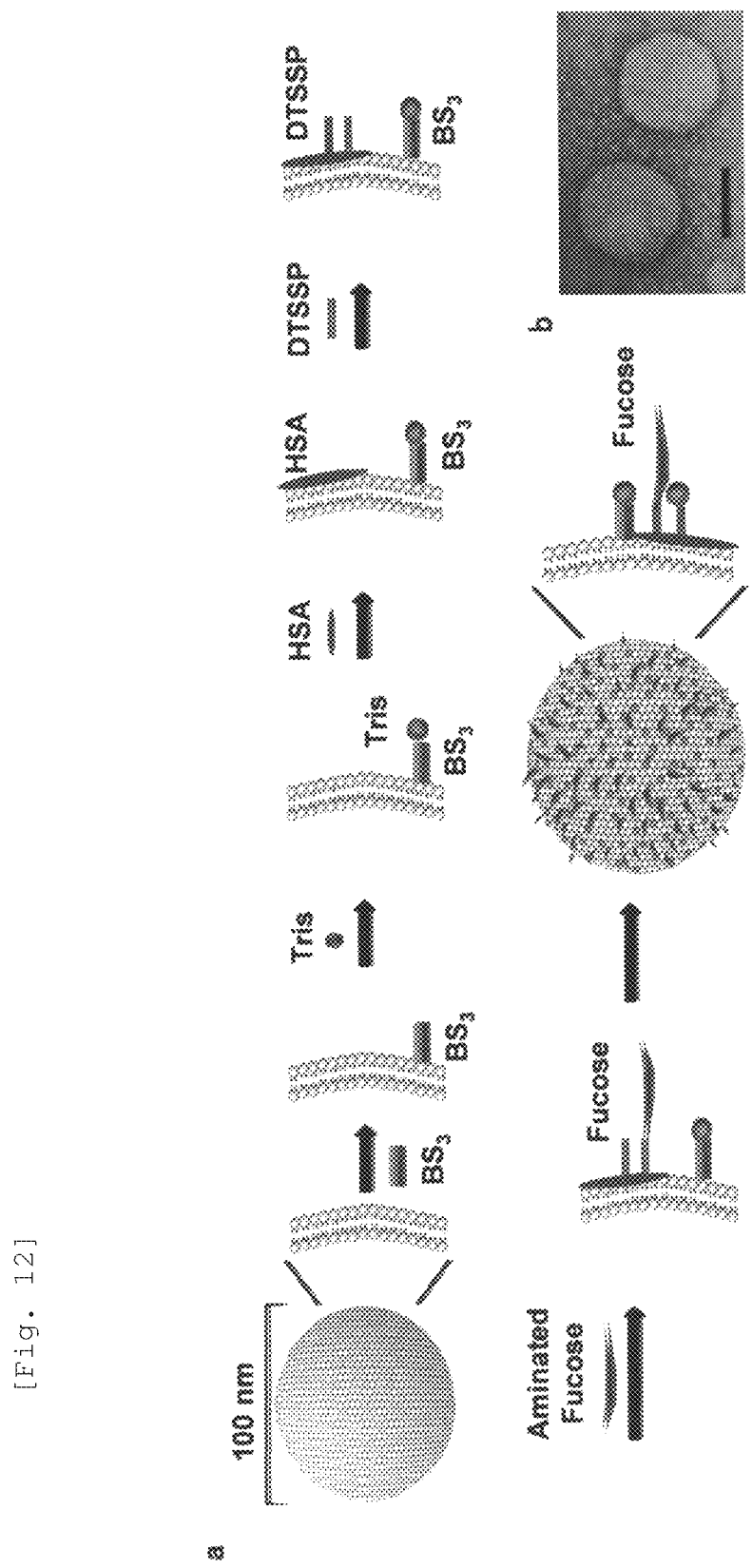
[Fig. 12]

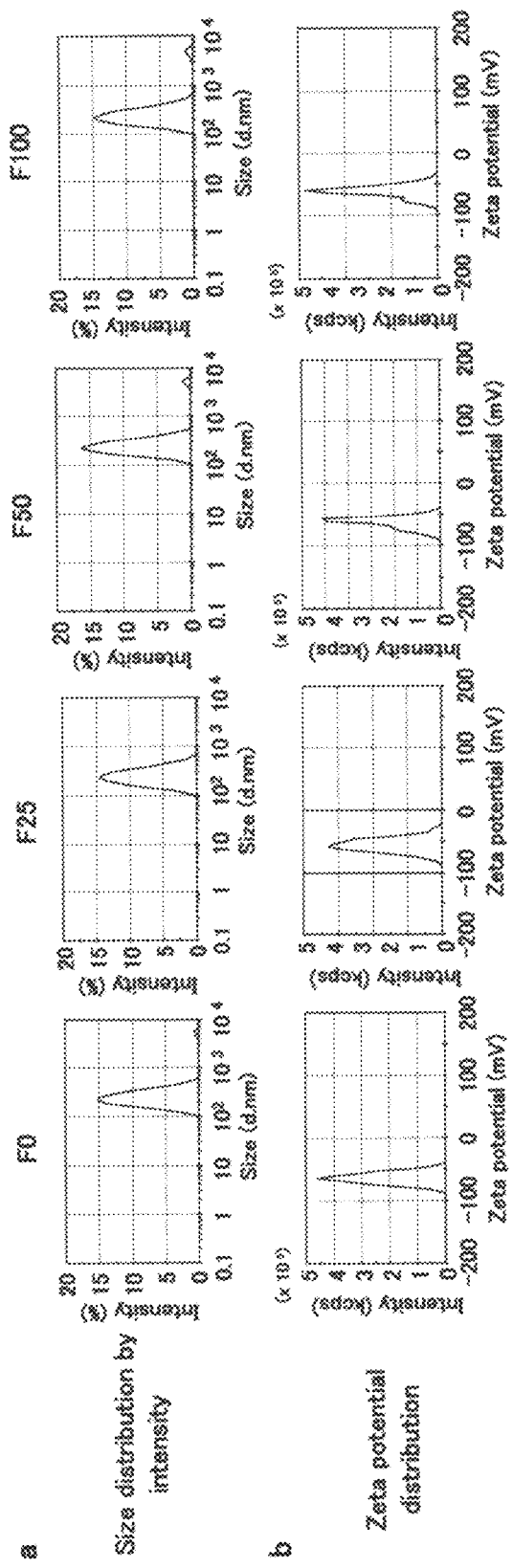
[Fig. 13]

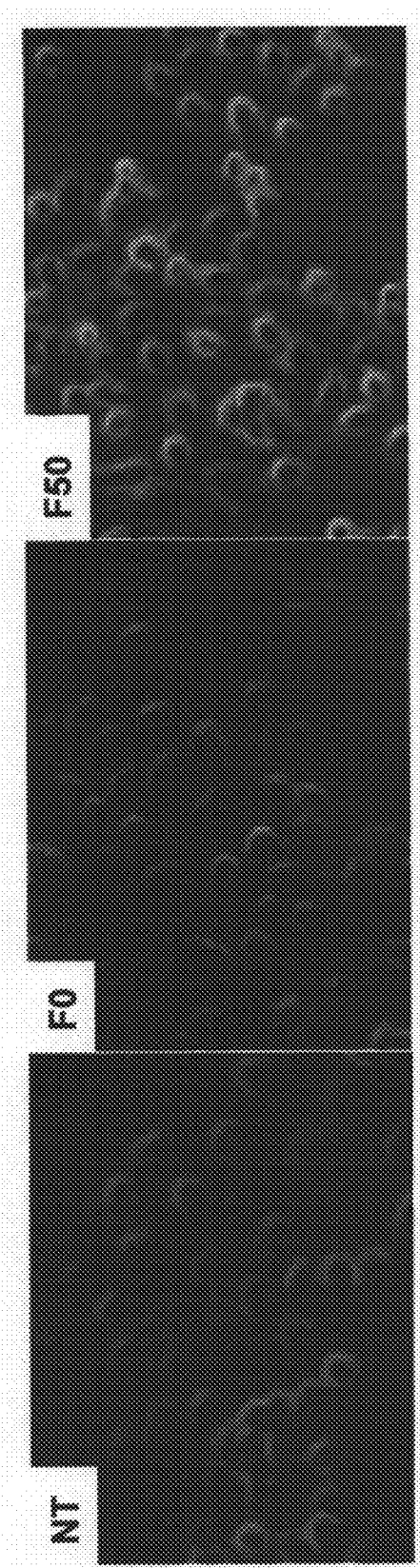
[Fig. 14]

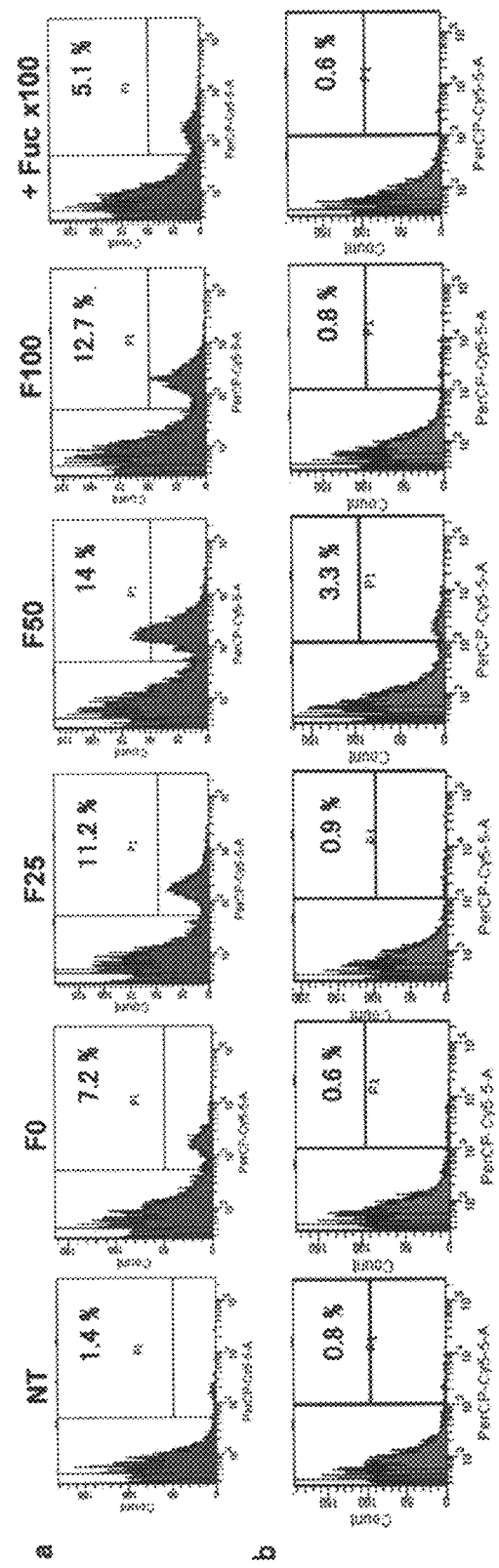
[Fig. 15]

[Fig. 16]
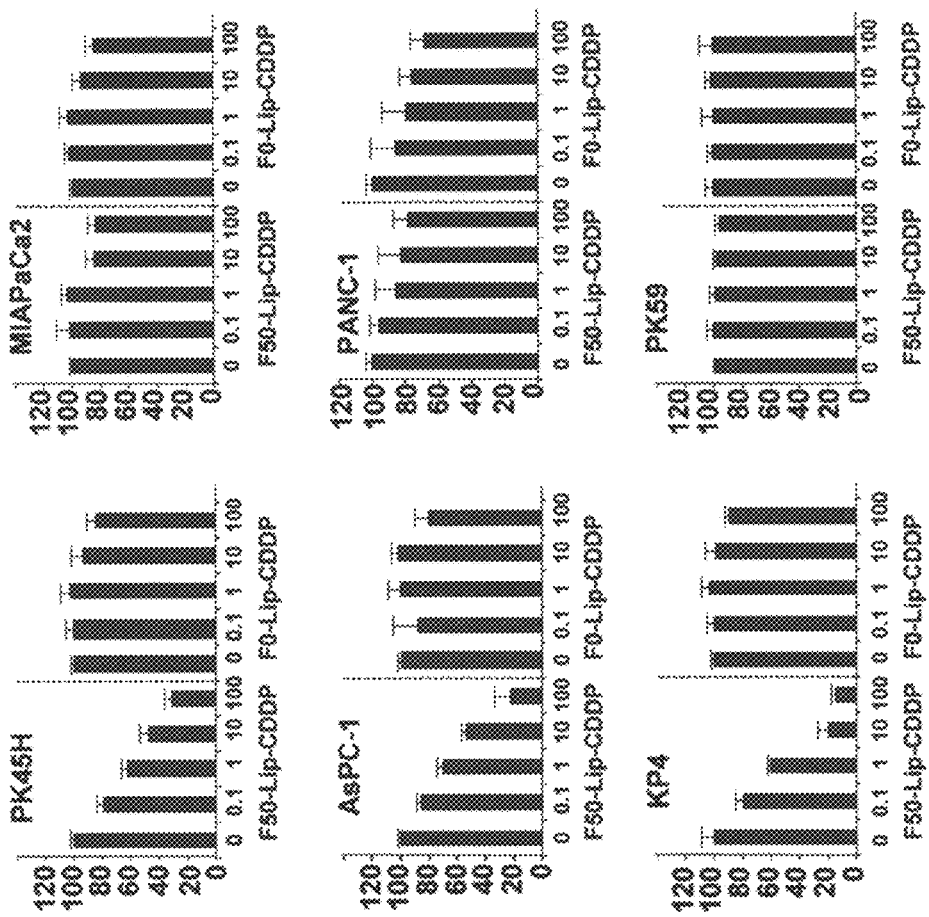
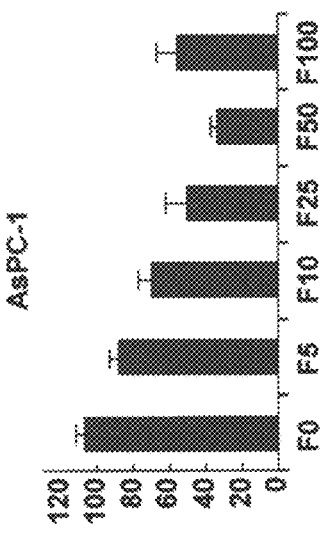
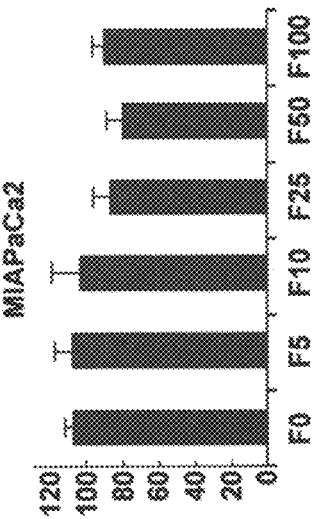

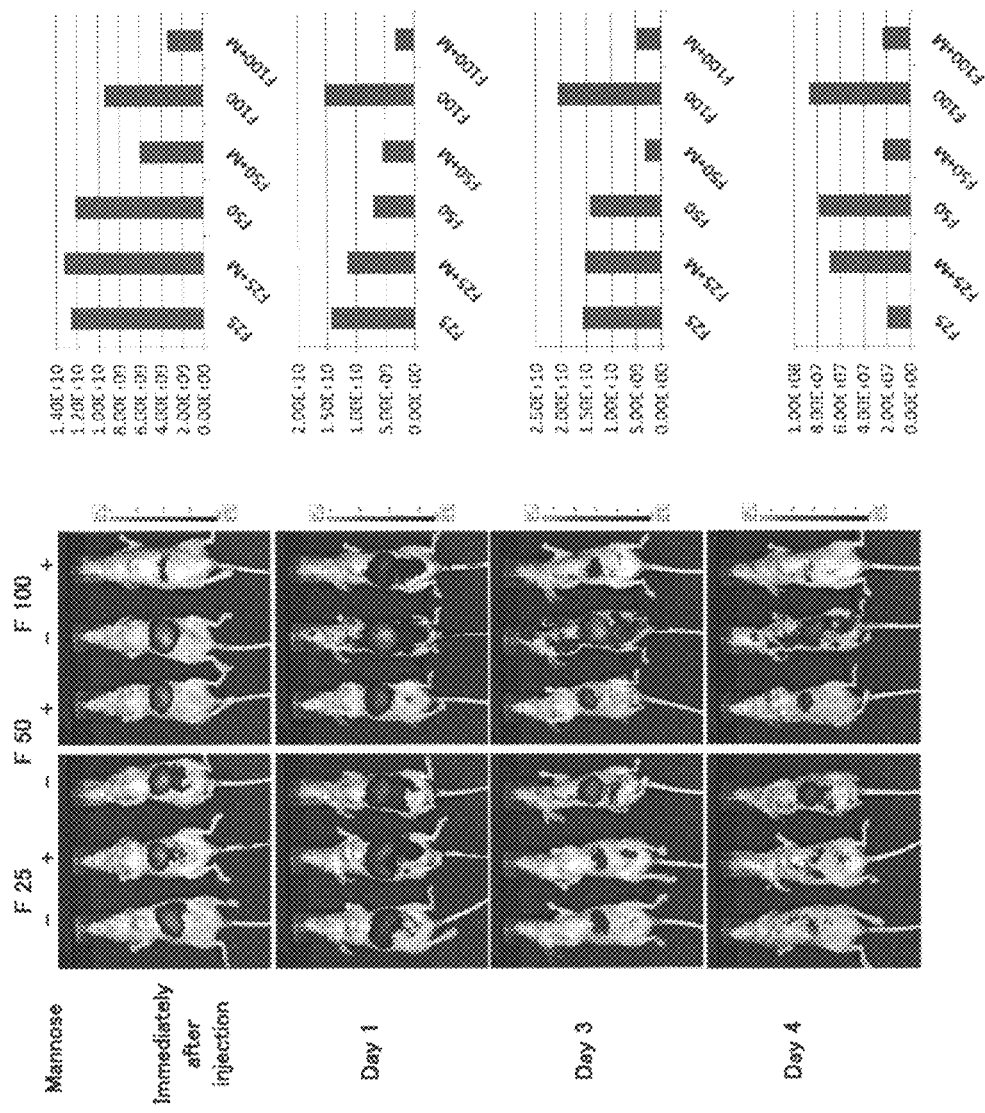
[Fig. 17]

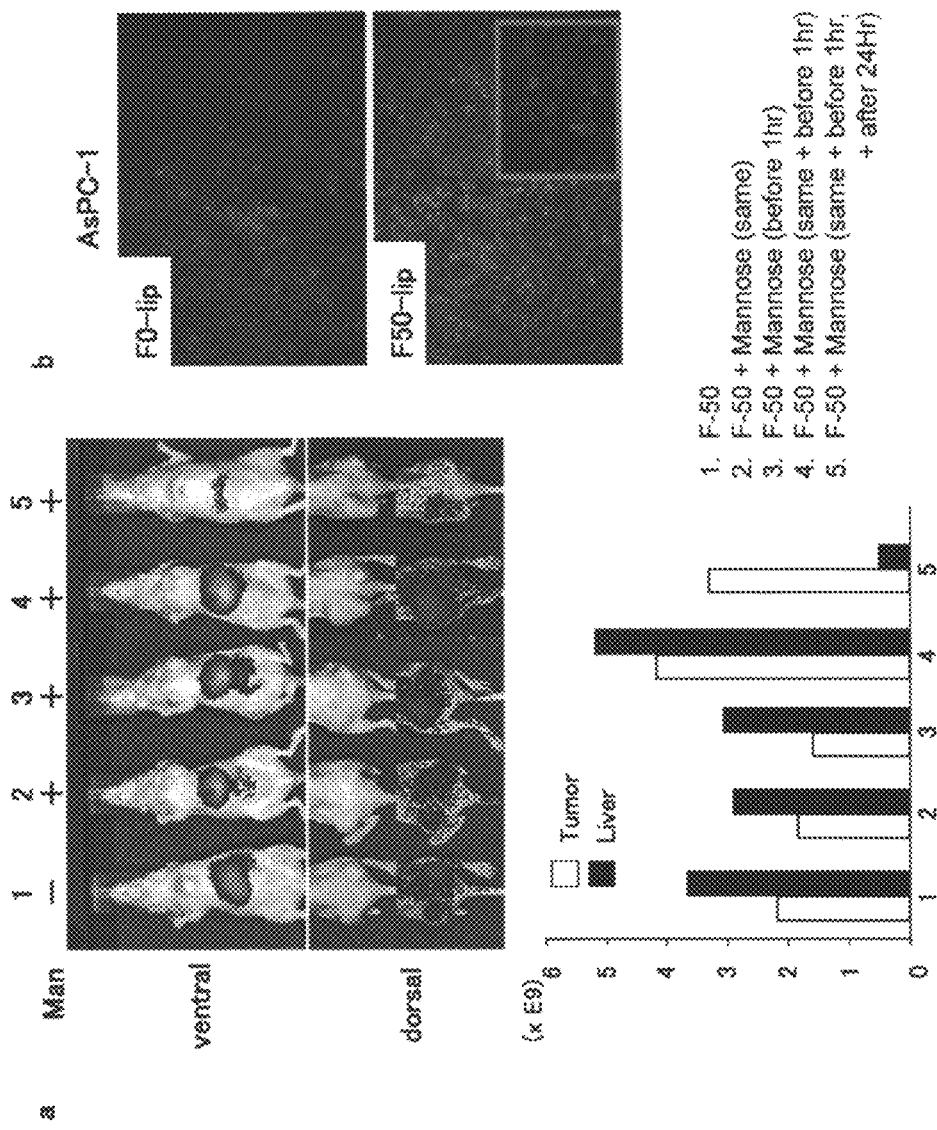
[Fig. 18]

[Fig. 19]
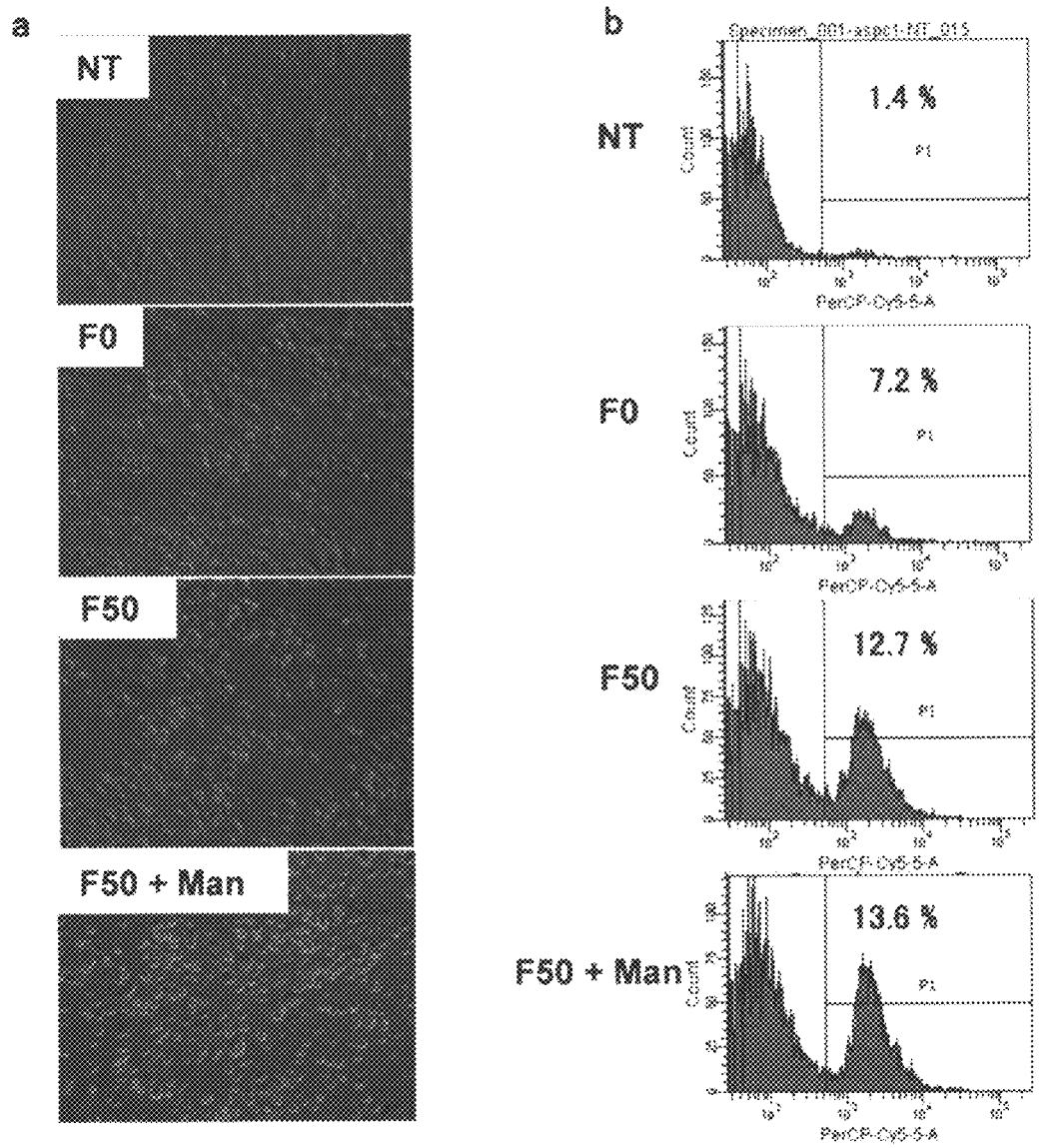

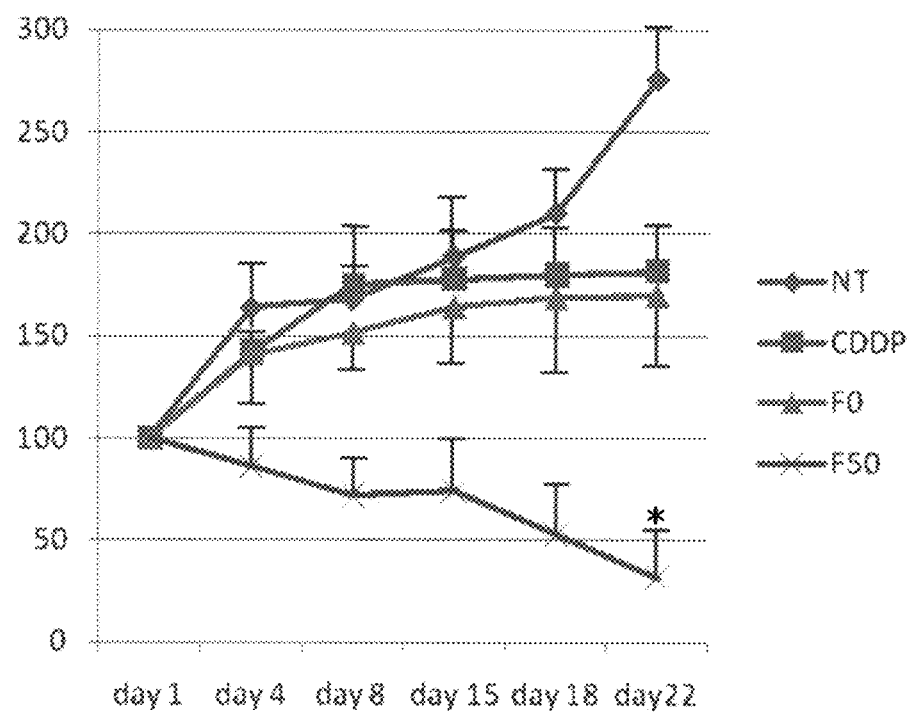
[Fig. 20]

[Fig. 21]
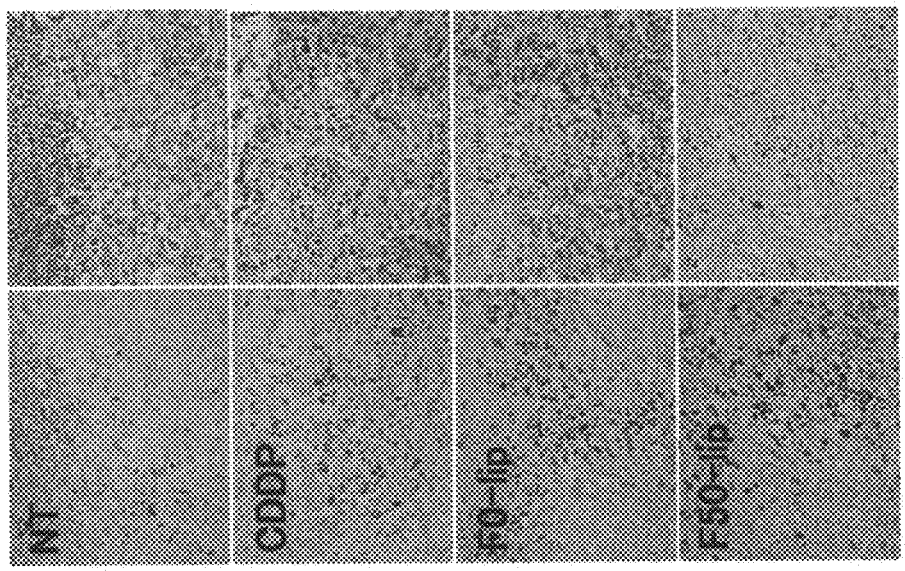
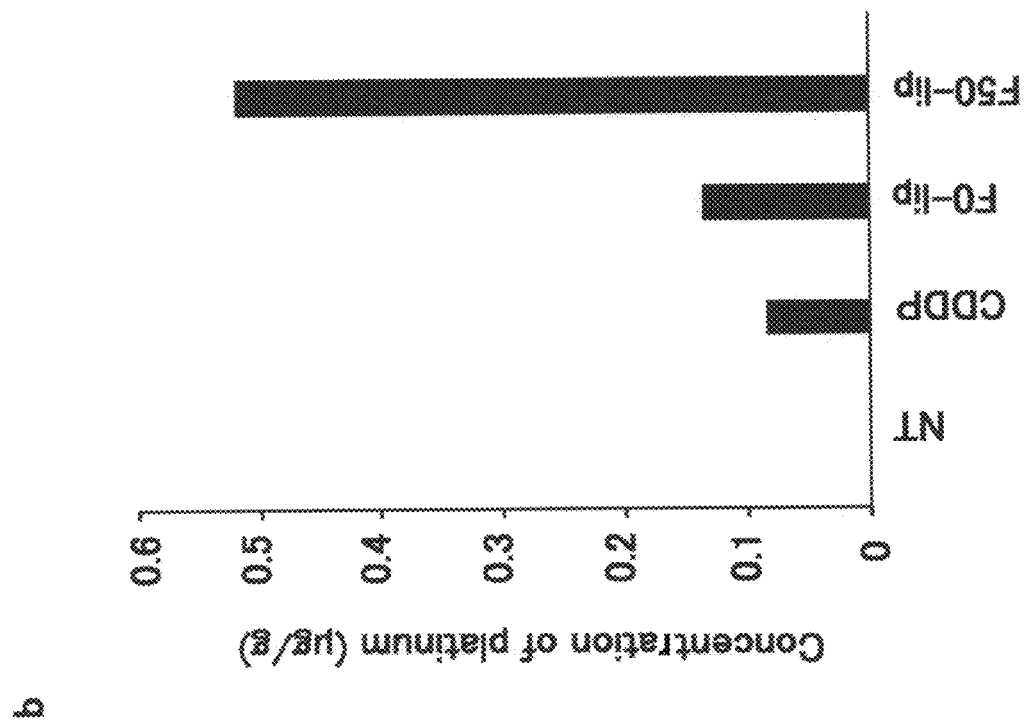

[Fig. 22]
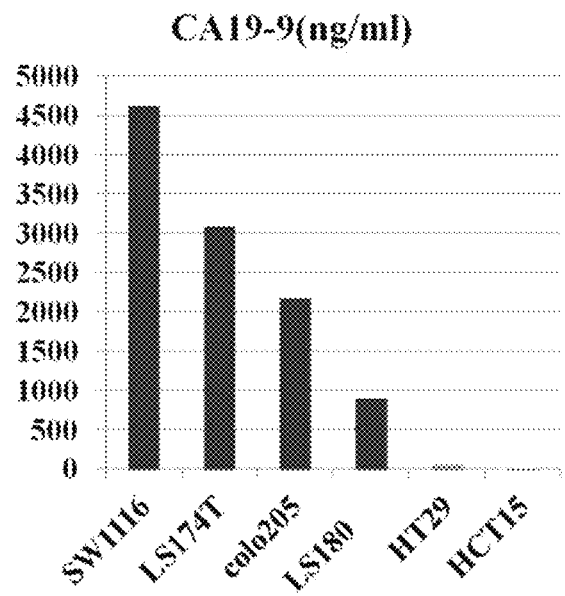
[Fig. 23]
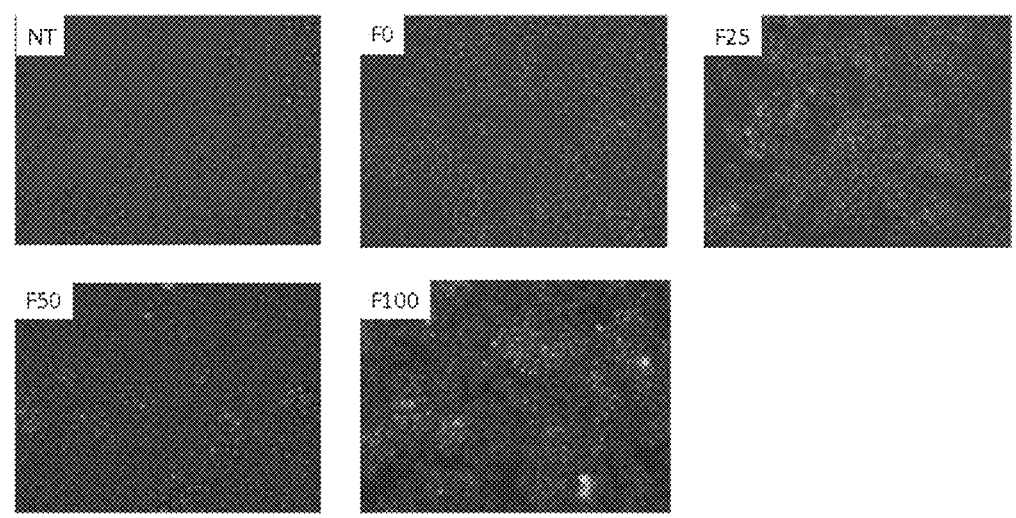

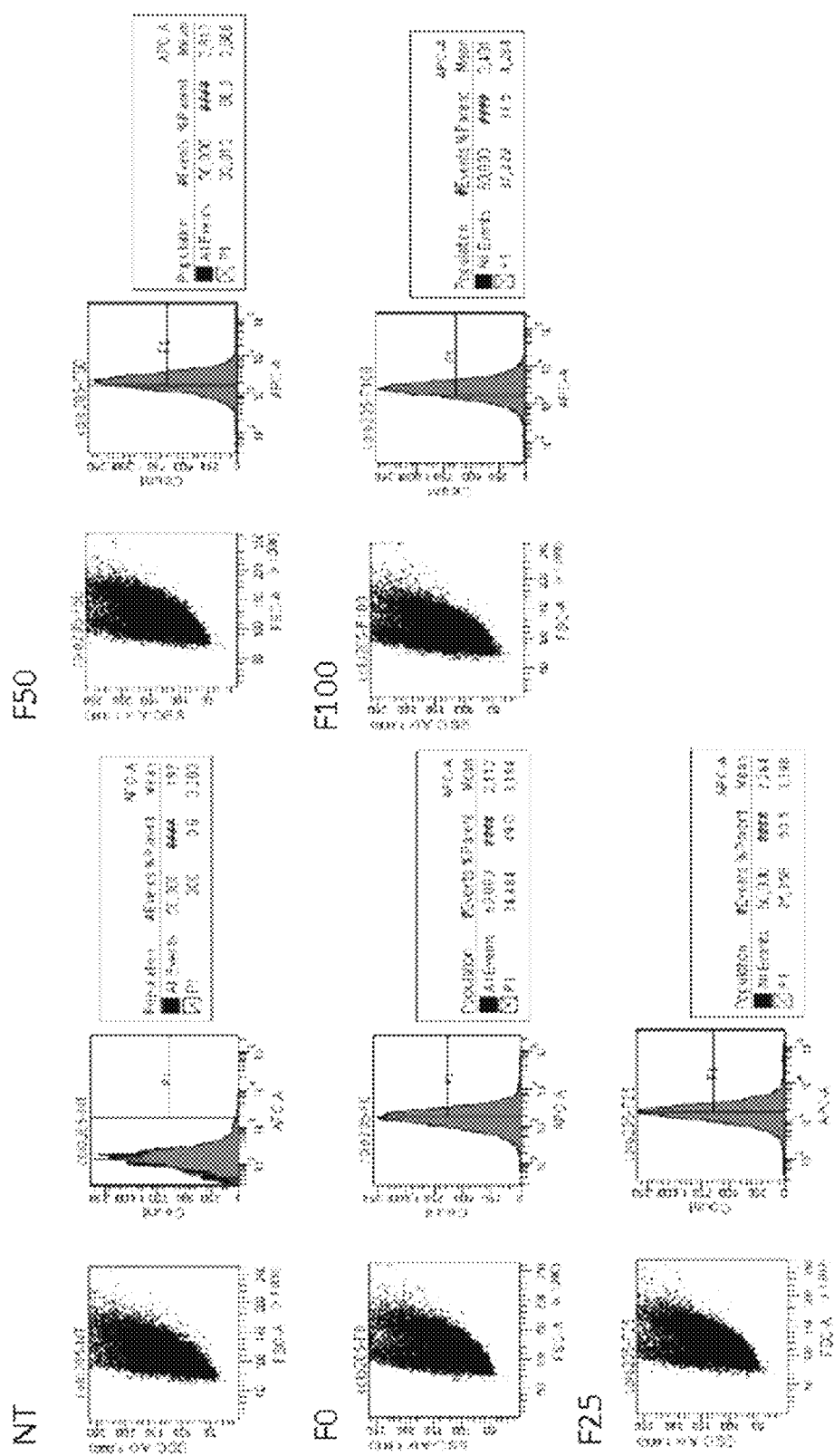
[Fig. 24]

[Fig. 25]
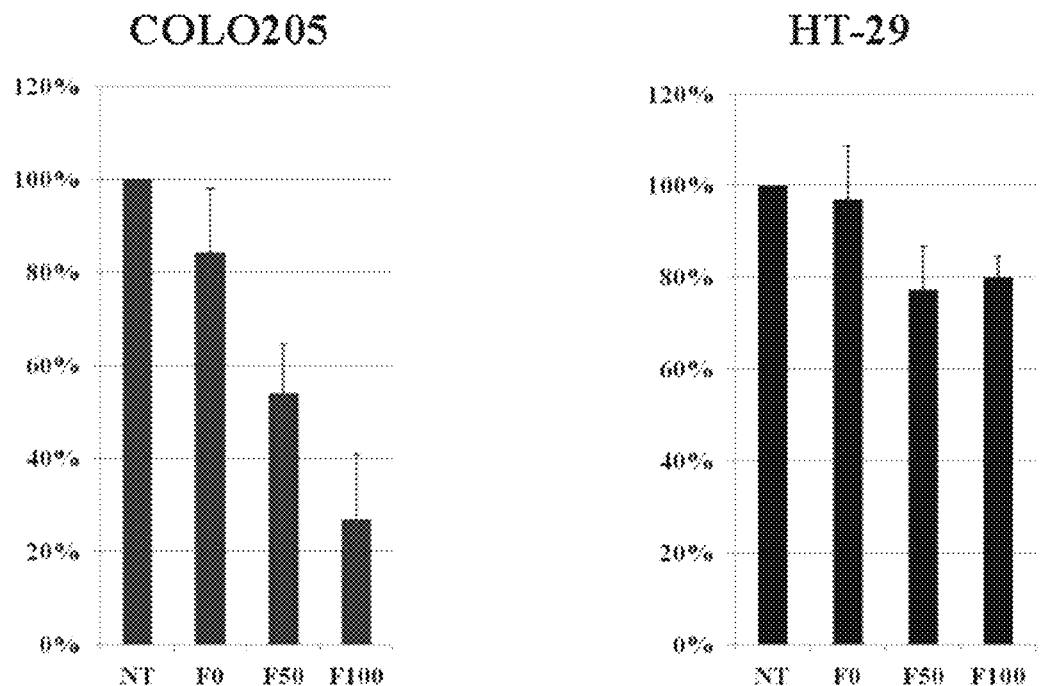

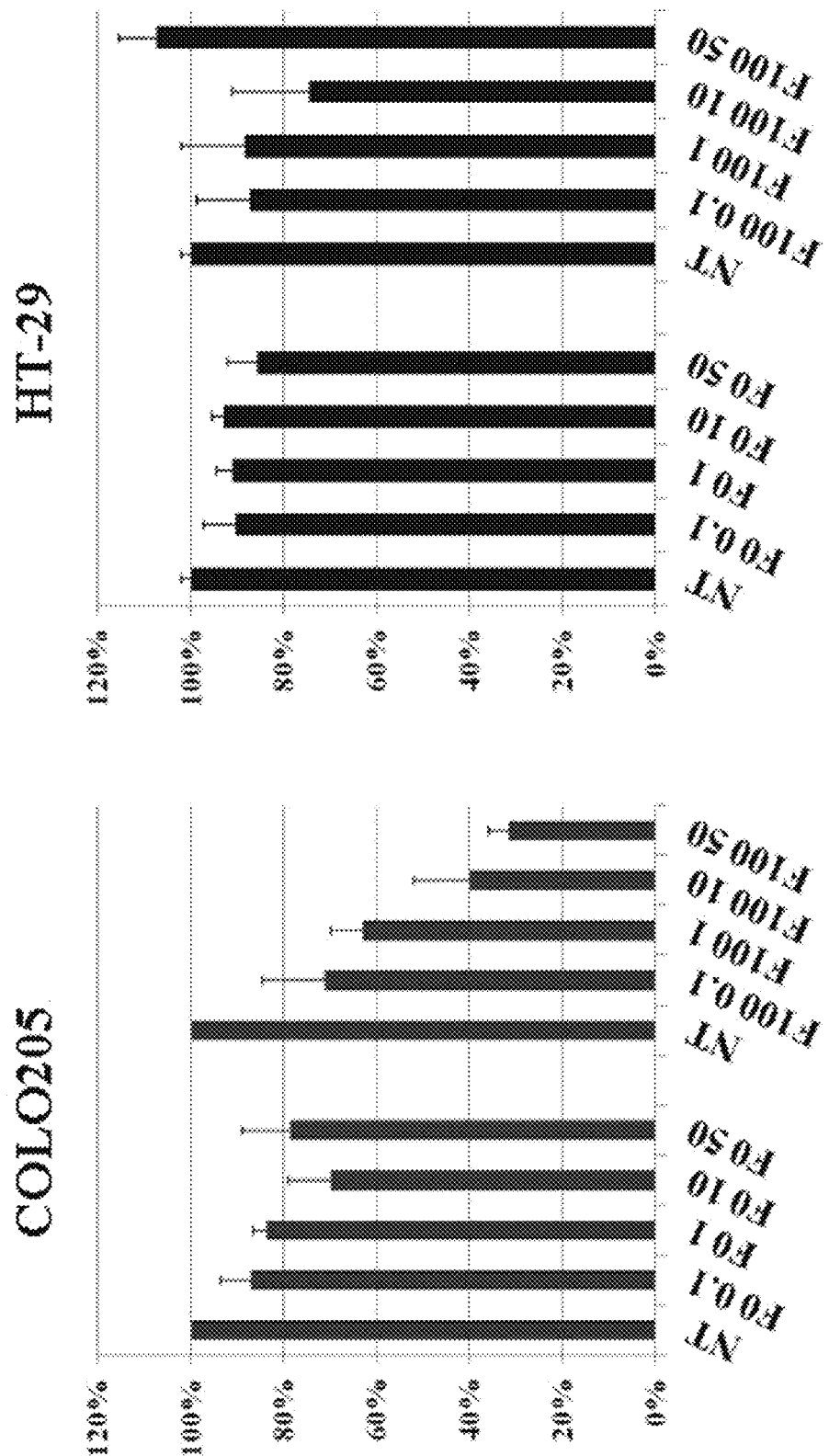
[Fig. 26]

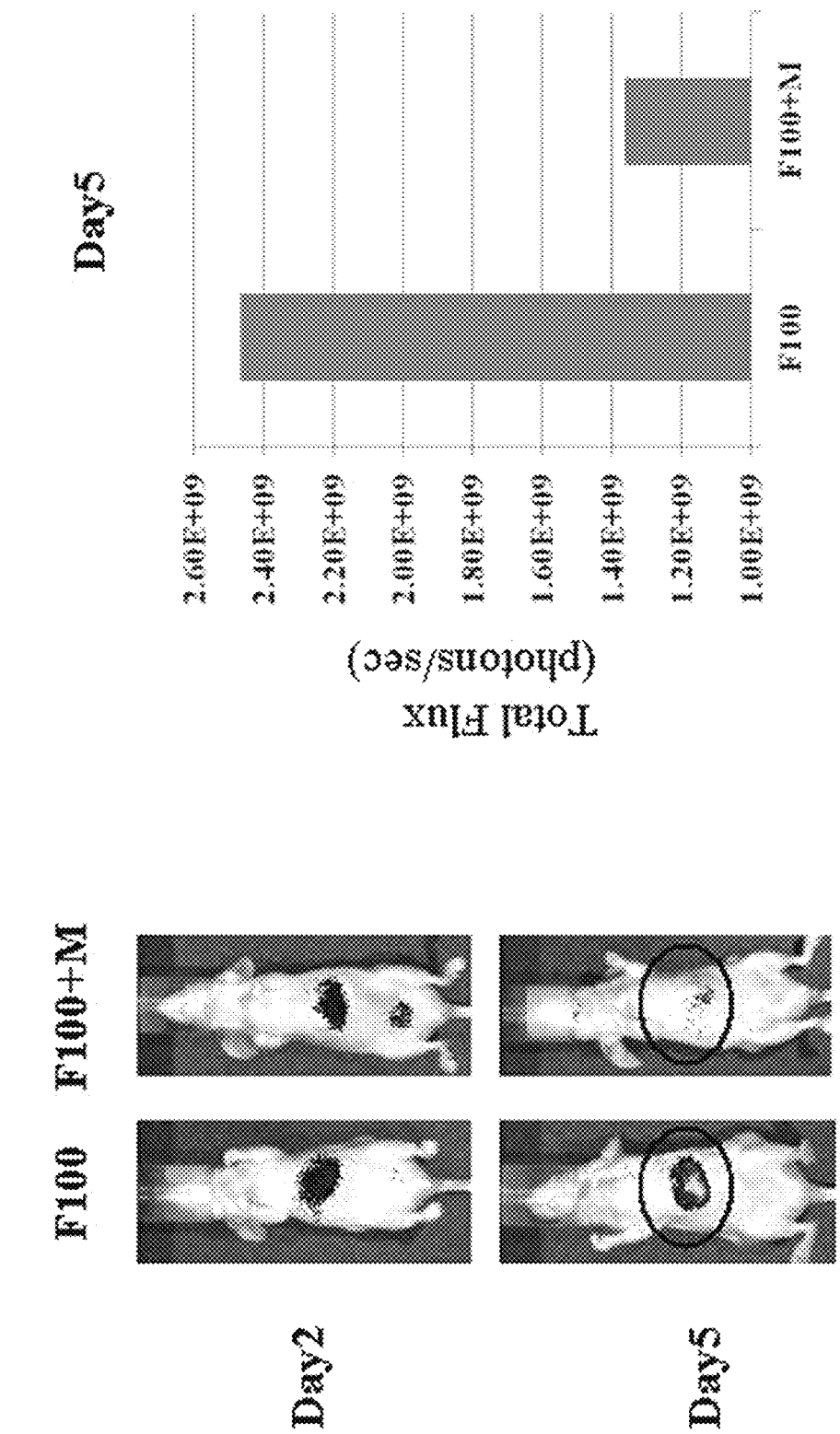
[Fig. 27]

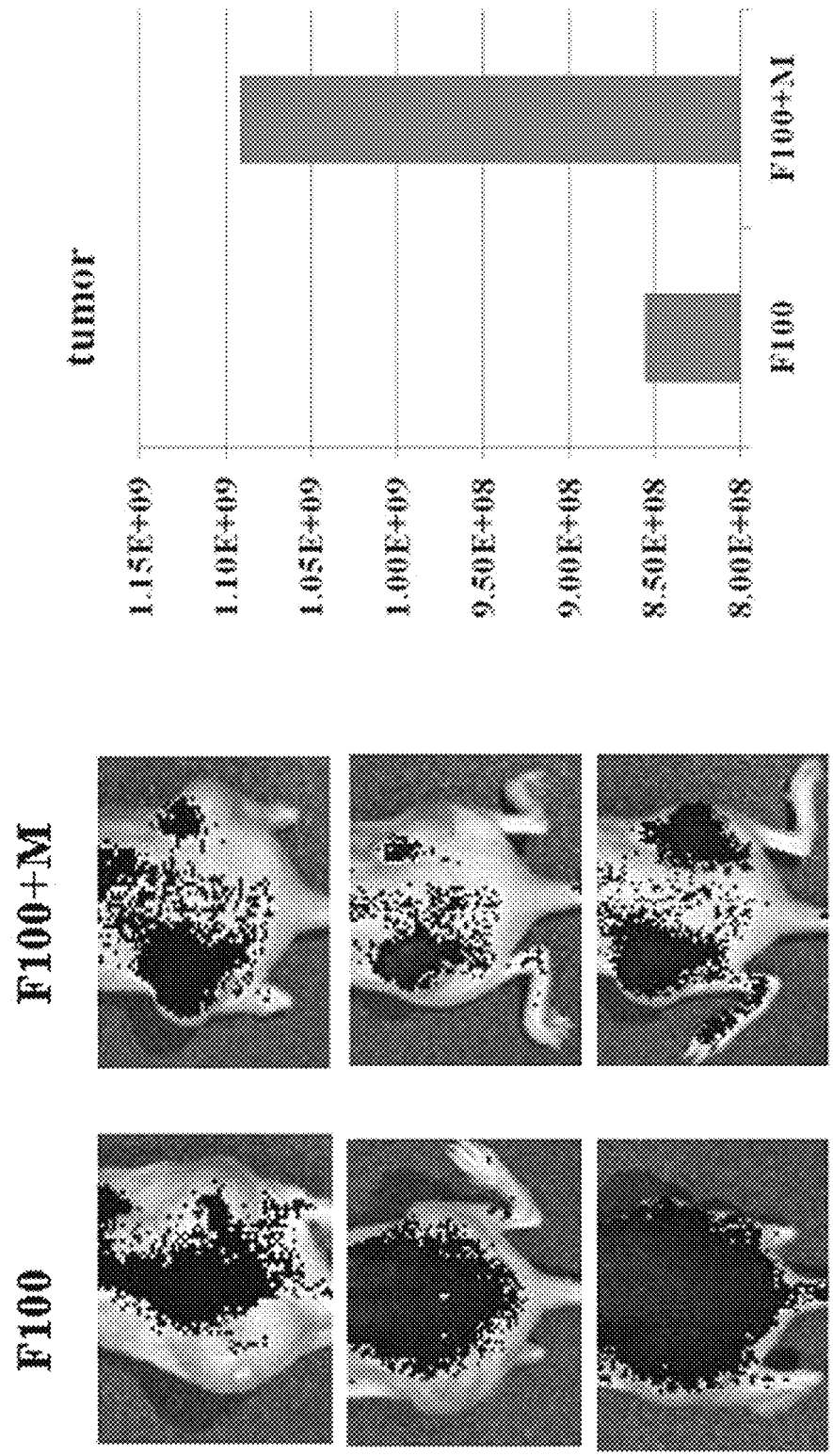
[Fig. 28]

[Fig. 29]
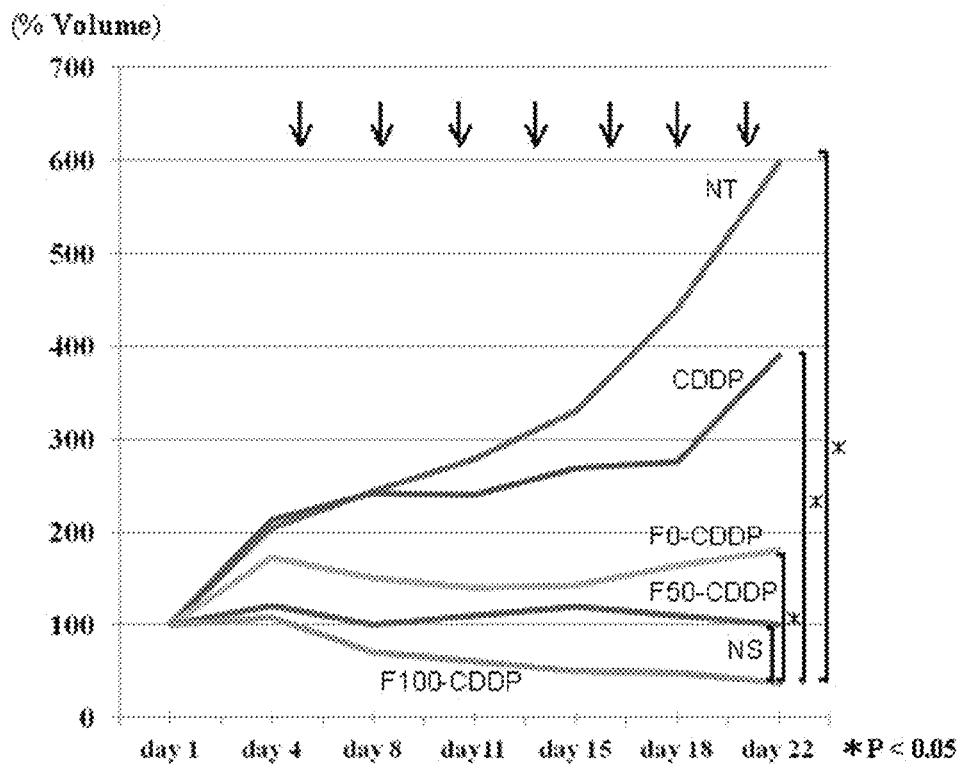
[Fig. 30]
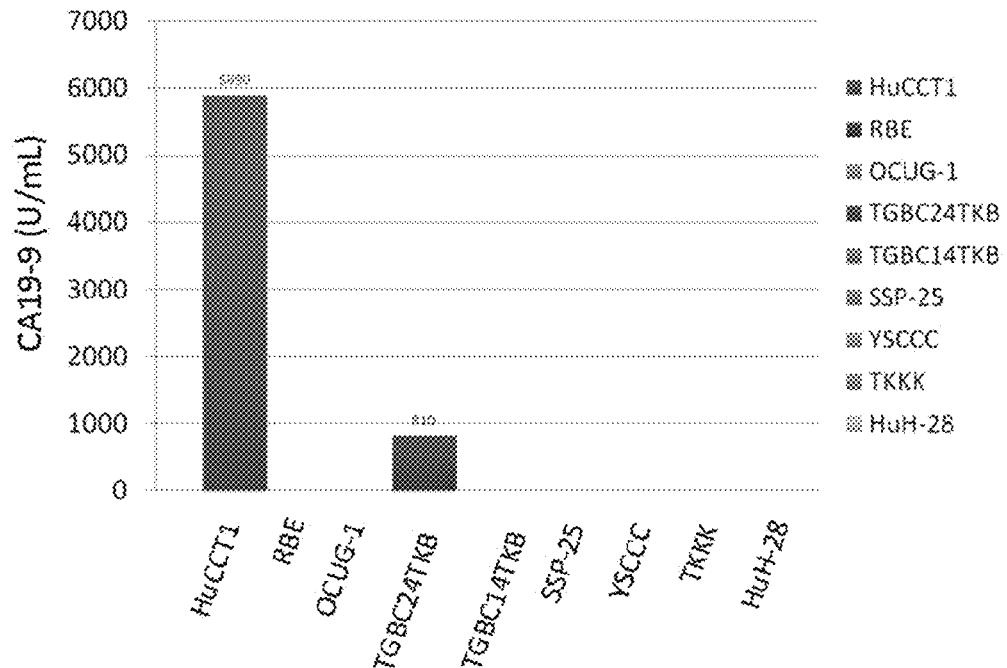

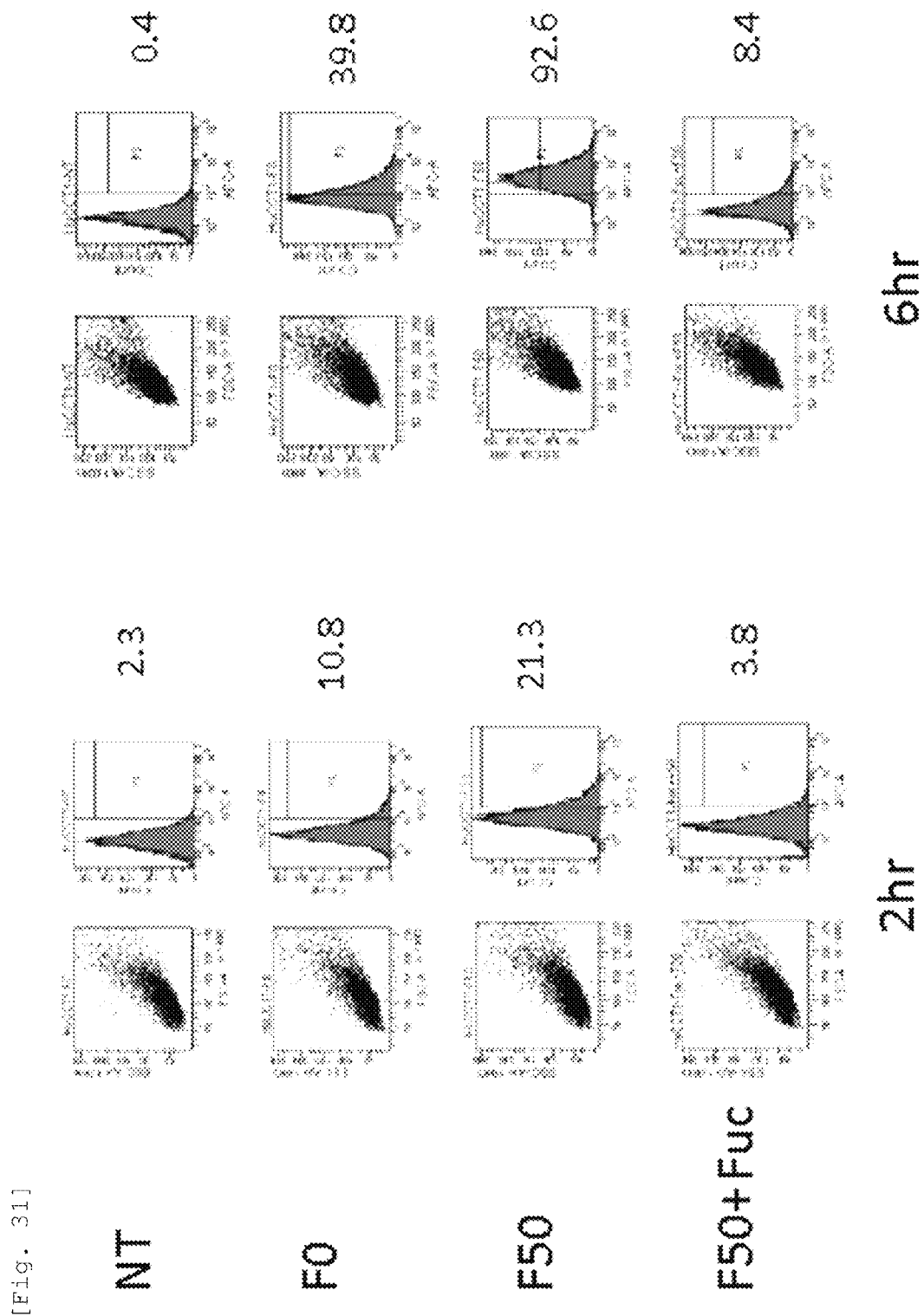
[Fig. 31]

[Fig. 32]
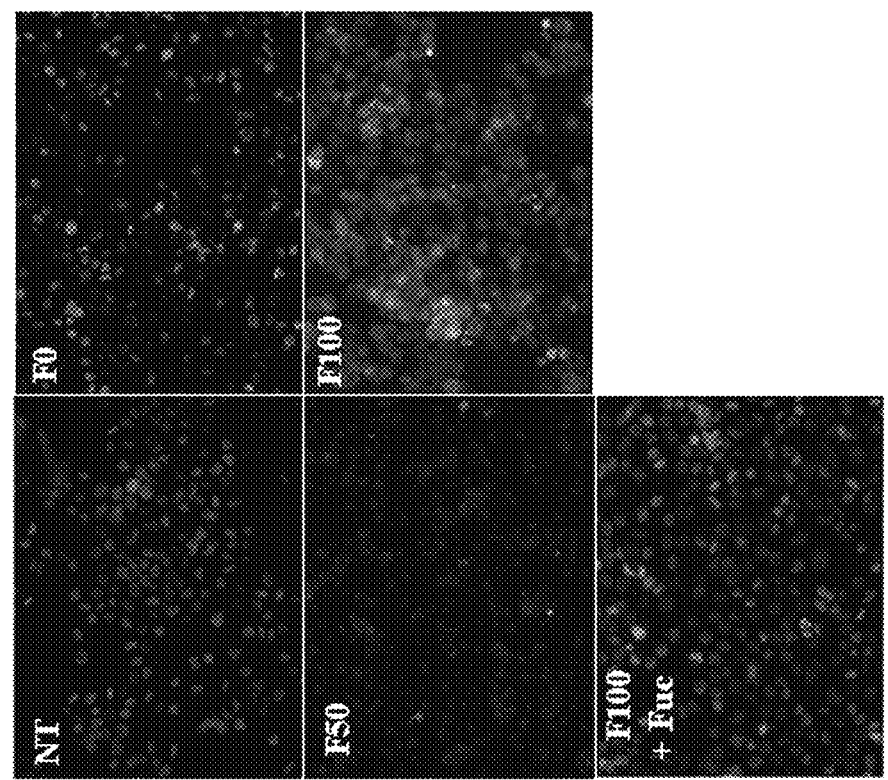
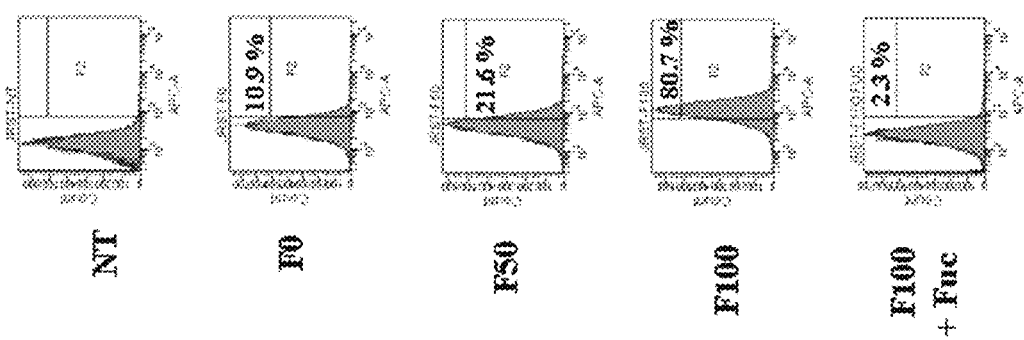

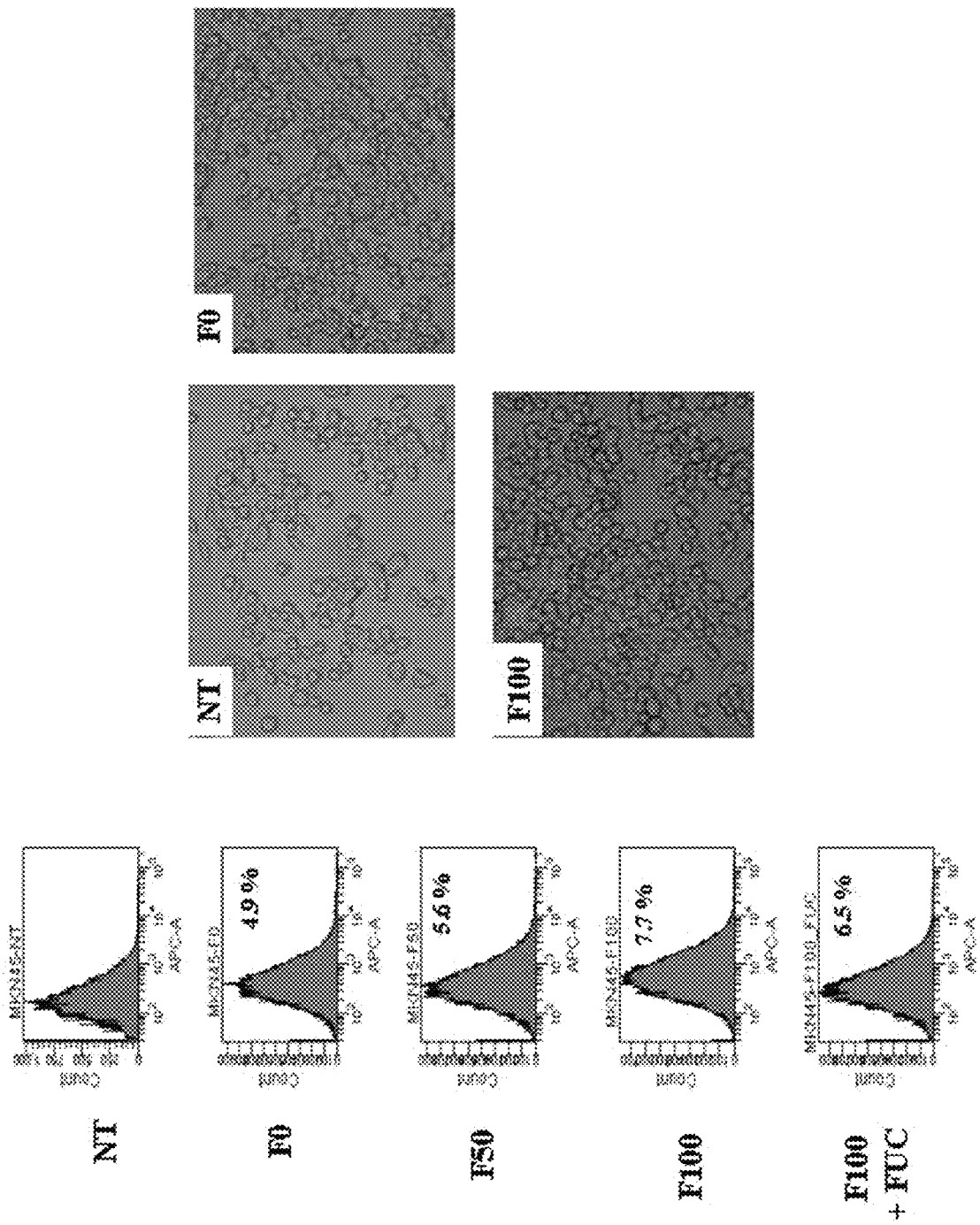
[Fig. 33]

[Fig. 34]
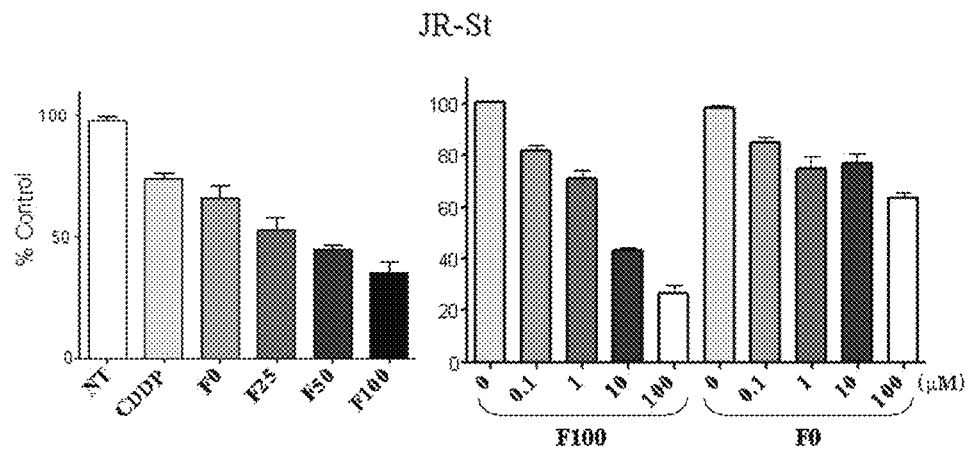
[Fig. 35]
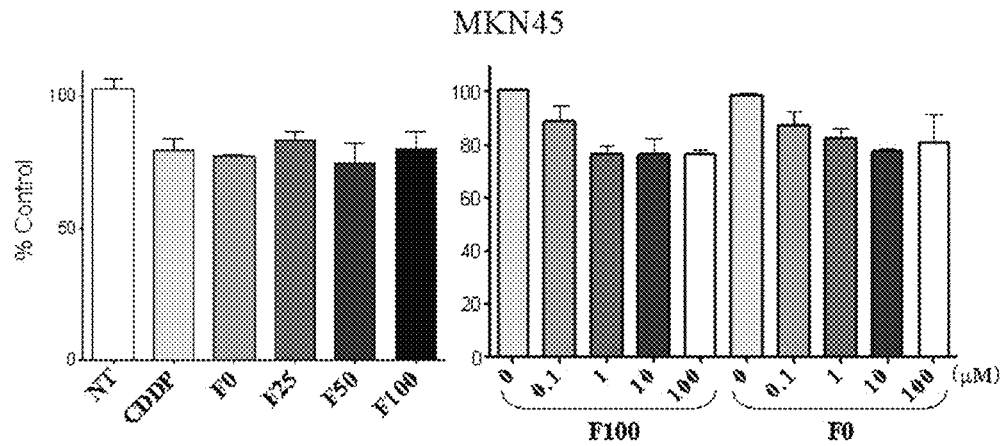

[Fig. 36]
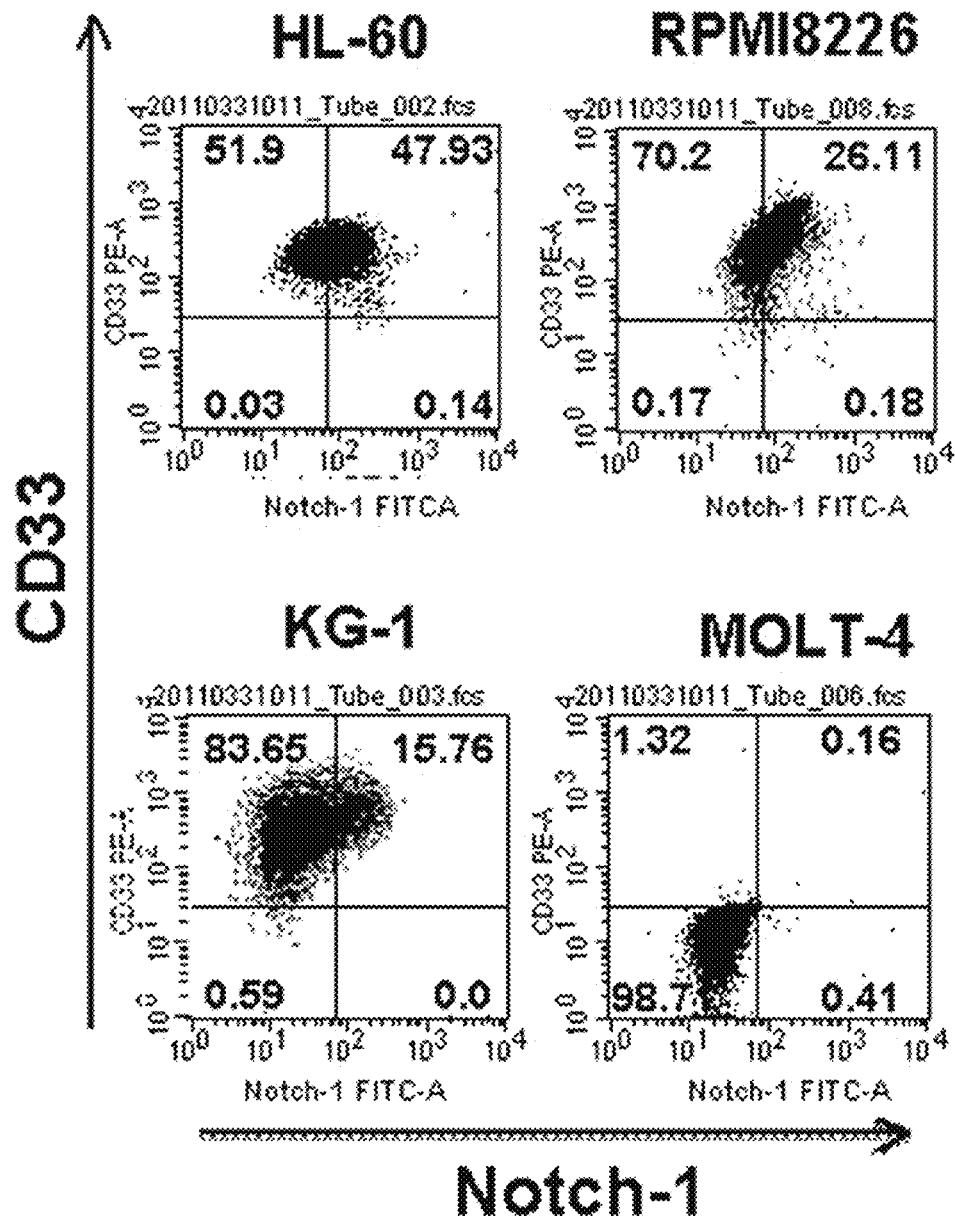

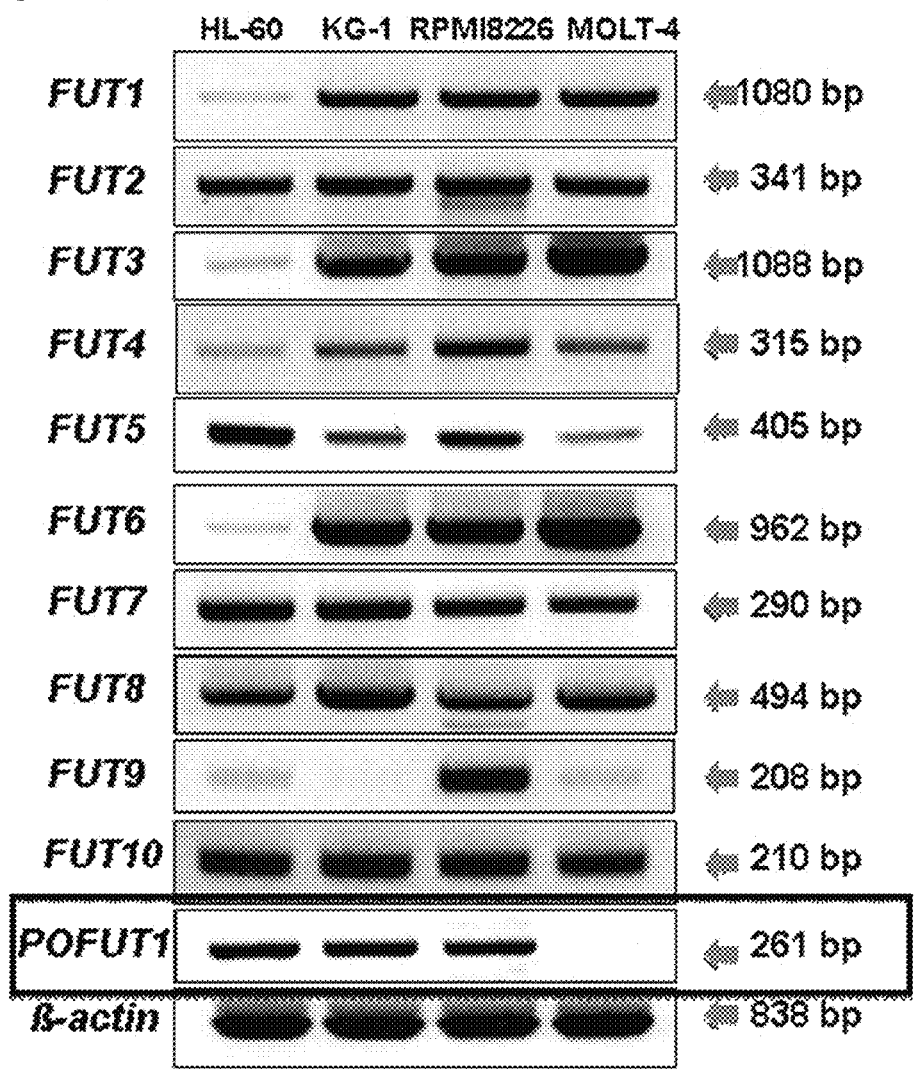
[Fig. 37]

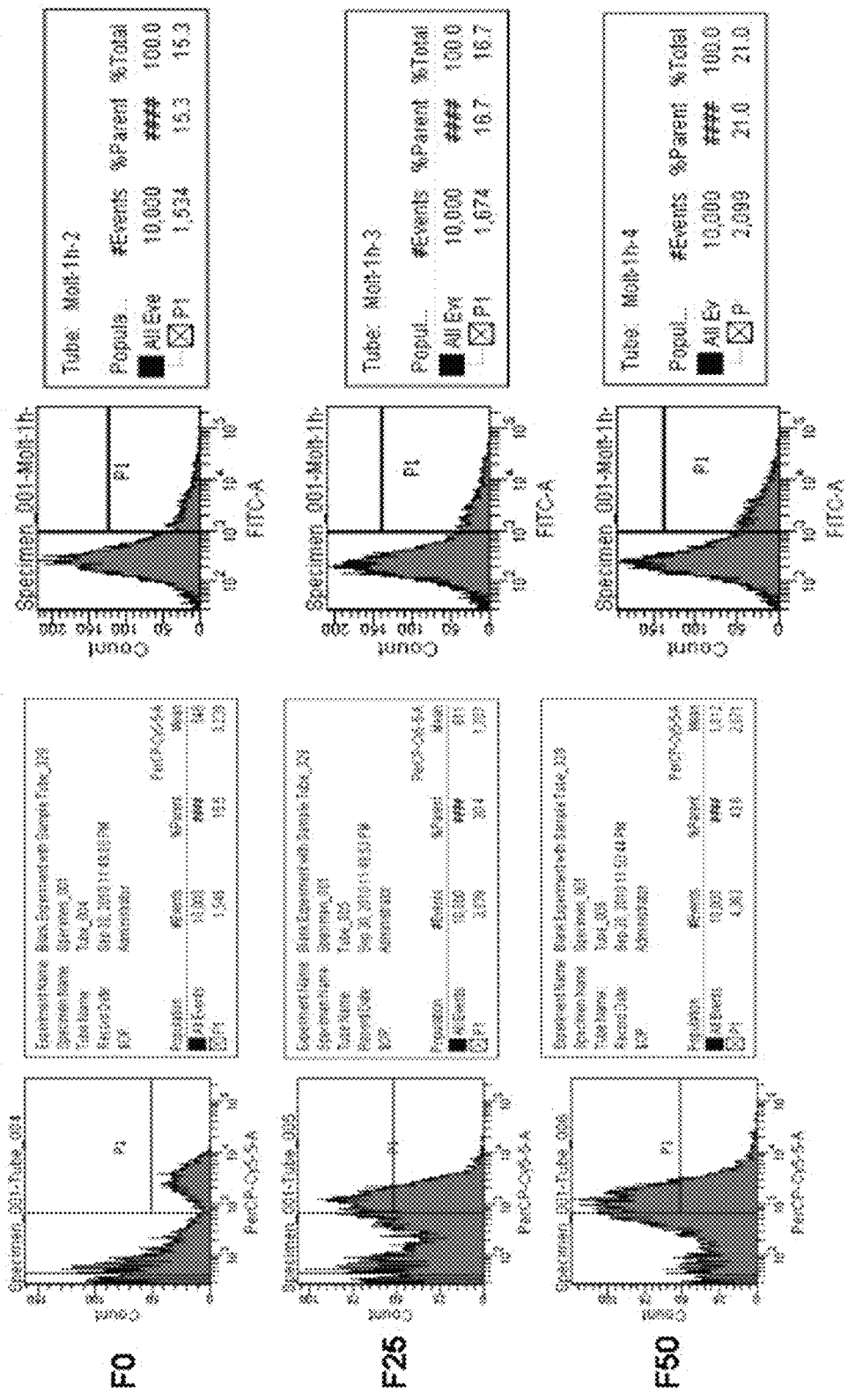
[Fig. 38]

[Fig. 39]
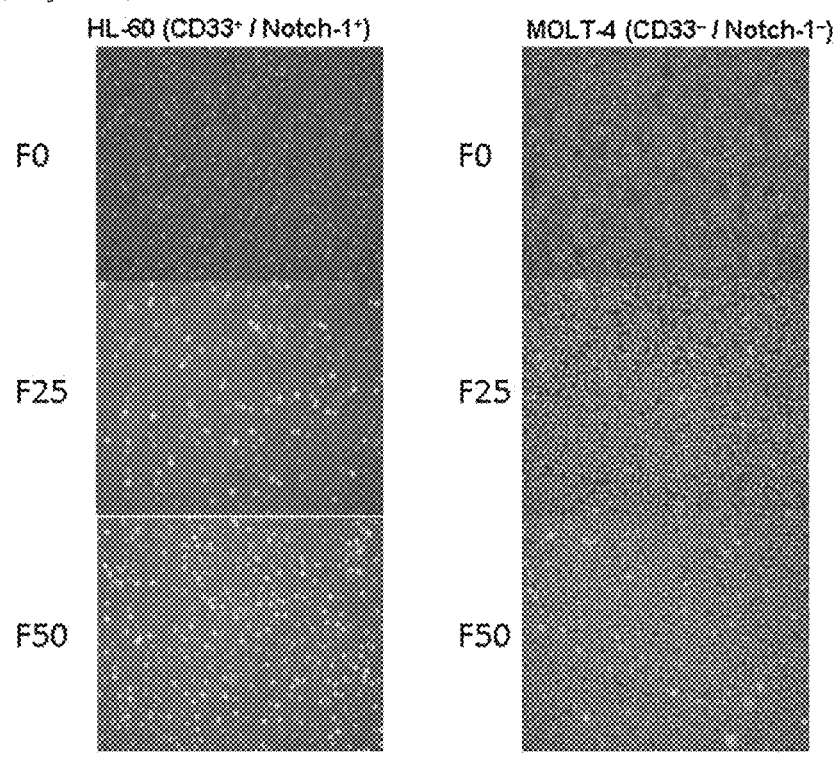
[Fig. 40]
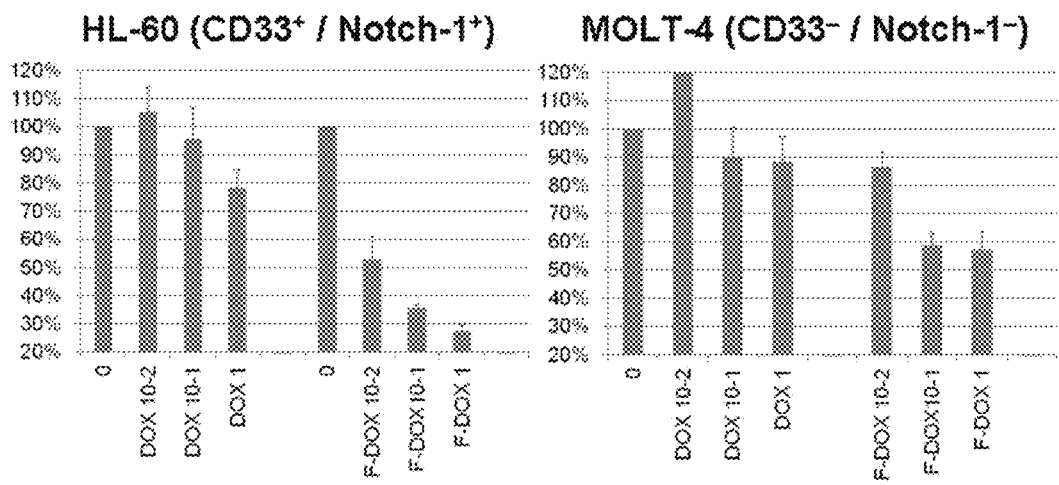

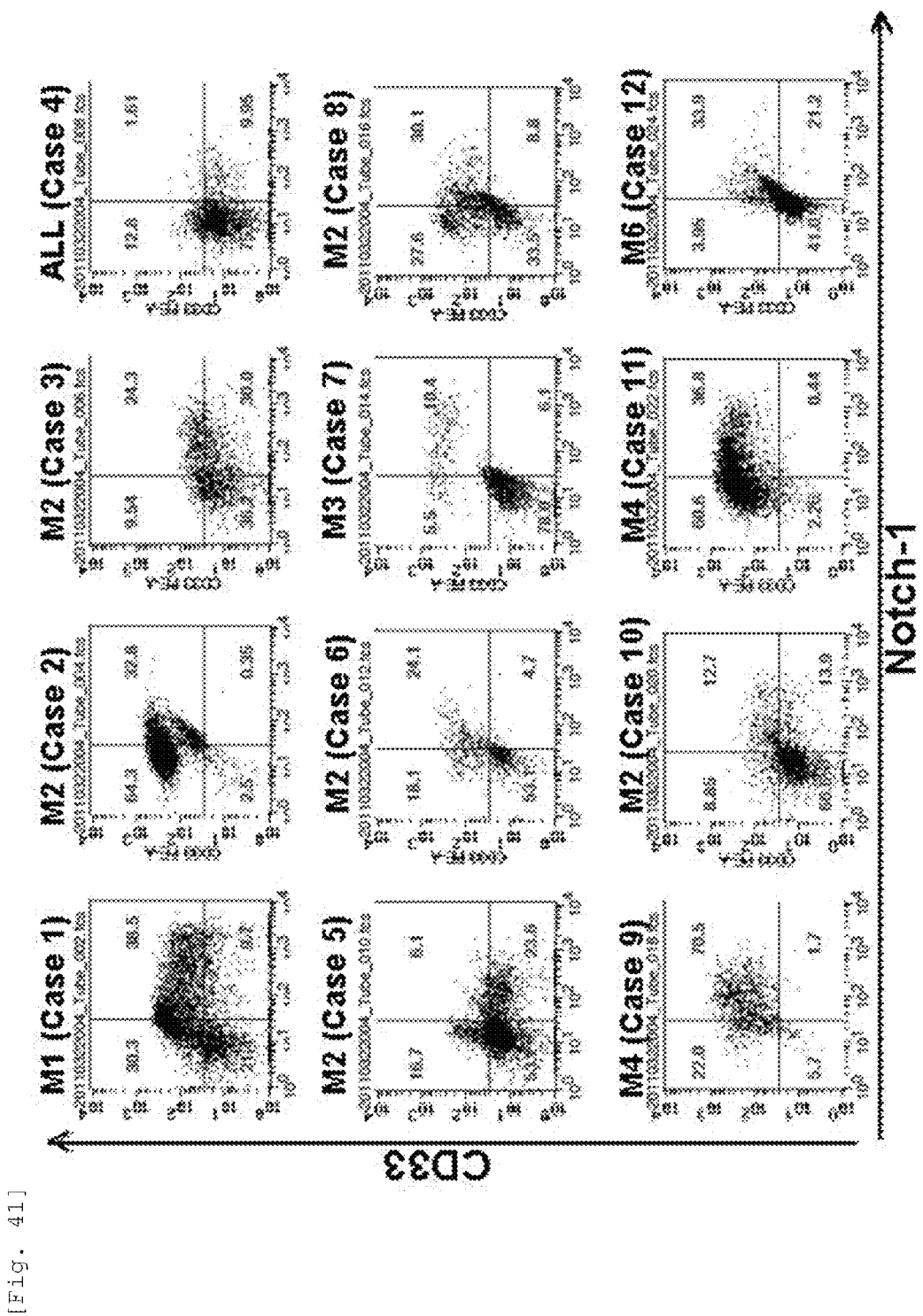
[Fig. 41]

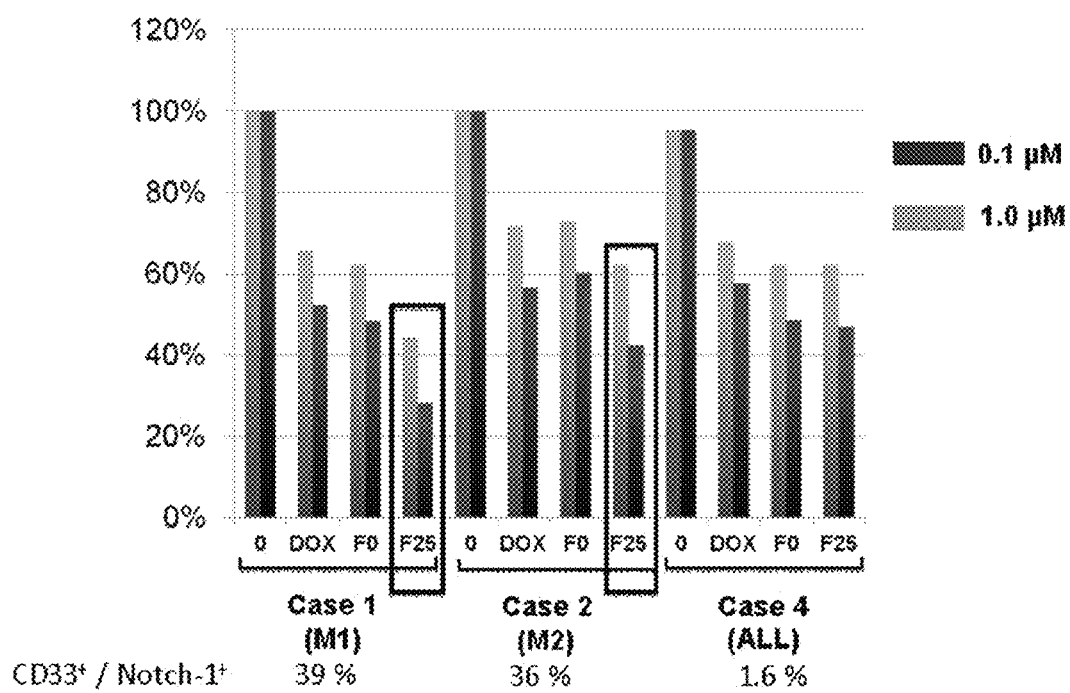

SEQUENCE LISTING

<160> NUMBER OF SEQ ID NOS: 60

<210> SEQ ID NO 1
<211> LENGTH: 24
<212> TYPE: DNA
<213> ORGANISM: artificial sequence
<220> FEATURE:
<223> OTHER INFORMATION: FUT1 RT-PCR primer U

<400> SEQUENCE: 1
atgtggctcc ggagccatcg tcag                                24

<210> SEQ ID NO 2
<211> LENGTH: 24
<212> TYPE: DNA
<213> ORGANISM: artificial sequence
<220> FEATURE:
<223> OTHER INFORMATION: FUT1 RT-PCR primer L

<400> SEQUENCE: 2
aggatctctc aagtccgcgt actc                                24

<210> SEQ ID NO 3
<211> LENGTH: 24
<212> TYPE: DNA
<213> ORGANISM: artificial sequence
<220> FEATURE:
<223> OTHER INFORMATION: FUT2 RT-PCR primer U

<400> SEQUENCE: 3
ctagcgaaga ttcaagccat gtgg                                24

<210> SEQ ID NO 4
<211> LENGTH: 21
<212> TYPE: DNA
<213> ORGANISM: artificial sequence
<220> FEATURE:
<223> OTHER INFORMATION: FUT2 RT-PCR primer L

<400> SEQUENCE: 4
gacgtactcc cccgggatgt g                                   21

<210> SEQ ID NO 5
<211> LENGTH: 24
<212> TYPE: DNA
<213> ORGANISM: artificial sequence
<220> FEATURE:
<223> OTHER INFORMATION: FUT3 RT-PCR primer U

<400> SEQUENCE: 5
atggatcccc tgggtgcagc caag                                24

<210> SEQ ID NO 6
<211> LENGTH: 24
<212> TYPE: DNA
<213> ORGANISM: artificial sequence
<220> FEATURE:
<223> OTHER INFORMATION: FUT3 RT-PCR primer L

<400> SEQUENCE: 6
tcaggtgaac caagccgcta tgct                                24

<210> SEQ ID NO 7
<211> LENGTH: 24
<212> TYPE: DNA
<213> ORGANISM: artificial sequence

```
<220> FEATURE:
<223> OTHER INFORMATION: FUT4 RT-PCR primer U

<400> SEQUENCE: 7
gtgcccgaaa ttgggctcct gcac                                         24

<210> SEQ ID NO 8
<211> LENGTH: 24
<212> TYPE: DNA
<213> ORGANISM: artificial sequence
<220> FEATURE:
<223> OTHER INFORMATION: FUT4 RT-PCR primer L

<400> SEQUENCE: 8
gaaggaggtg atgtggacag cgta                                         24

<210> SEQ ID NO 9
<211> LENGTH: 24
<212> TYPE: DNA
<213> ORGANISM: artificial sequence
<220> FEATURE:
<223> OTHER INFORMATION: FUT5 RT-PCR primer U

<400> SEQUENCE: 9
cttatggcag tggaacctgt cacc                                         24

<210> SEQ ID NO 10
<211> LENGTH: 24
<212> TYPE: DNA
<213> ORGANISM: artificial sequence
<220> FEATURE:
<223> OTHER INFORMATION: FUT5 RT-PCR primer L

<400> SEQUENCE: 10
ccagccgtag ggcgtgaaga tgtc                                         24

<210> SEQ ID NO 11
<211> LENGTH: 24
<212> TYPE: DNA
<213> ORGANISM: artificial sequence
<220> FEATURE:
<223> OTHER INFORMATION: FUT6 RT-PCR primer U

<400> SEQUENCE: 11
cccactgtgt accctaatgg gtcc                                         24

<210> SEQ ID NO 12
<211> LENGTH: 24
<212> TYPE: DNA
<213> ORGANISM: artificial sequence
<220> FEATURE:
<223> OTHER INFORMATION: FUT6 RT-PCR primer L

<400> SEQUENCE: 12
ctctcaggtg aaccaagccg ctat                                         24

<210> SEQ ID NO 13
<211> LENGTH: 22
<212> TYPE: DNA
<213> ORGANISM: artificial sequence
<220> FEATURE:
<223> OTHER INFORMATION: FUT7 RT-PCR primer U

<400> SEQUENCE: 13
tcggacatct ttgtgcccta tg                                           22
```

<210> SEQ ID NO 14
<211> LENGTH: 23
<212> TYPE: DNA
<213> ORGANISM: artificial sequence
<220> FEATURE:
<223> OTHER INFORMATION: FUT7 RT-PCR primer L

<400> SEQUENCE: 14
cgccagaatt tctccgtaat gta                                        23

<210> SEQ ID NO 15
<211> LENGTH: 20
<212> TYPE: DNA
<213> ORGANISM: artificial sequence
<220> FEATURE:
<223> OTHER INFORMATION: FUT8 RT-PCR primer U

<400> SEQUENCE: 15
tgcctggggg accttgctgt                                            20

<210> SEQ ID NO 16
<211> LENGTH: 20
<212> TYPE: DNA
<213> ORGANISM: artificial sequence
<220> FEATURE:
<223> OTHER INFORMATION: FUT8 RT-PCR primer L

<400> SEQUENCE: 16
cccgccaatc acctgctcca                                            20

<210> SEQ ID NO 17
<211> LENGTH: 32
<212> TYPE: DNA
<213> ORGANISM: artificial sequence
<220> FEATURE:
<223> OTHER INFORMATION: beta-actin RT-PCR primer U

<400> SEQUENCE: 17
atctggcacc acaccttcta caatgagctg cg                              32

<210> SEQ ID NO 18
<211> LENGTH: 32
<212> TYPE: DNA
<213> ORGANISM: artificial sequence
<220> FEATURE:
<223> OTHER INFORMATION: beta-actin RT-PCR primer L

<400> SEQUENCE: 18
cgtcatactc ctgcttgctg atccacatct gc                              32

<210> SEQ ID NO 19
<211> LENGTH: 27
<212> TYPE: RNA
<213> ORGANISM: artificial sequence
<220> FEATURE:
<223> OTHER INFORMATION: FAM siRNA sense

<400> SEQUENCE: 19
cgauucgcua gaccggcuuc auugcag                                    27

<210> SEQ ID NO 20
<211> LENGTH: 27
<212> TYPE: RNA
<213> ORGANISM: artificial sequence
<220> FEATURE:
<223> OTHER INFORMATION: FAM siRNA antisense

```
<400> SEQUENCE: 20
gcaaugaagc cggucuagcg aaucgau                                          27

<210> SEQ ID NO 21
<211> LENGTH: 25
<212> TYPE: RNA
<213> ORGANISM: artificial sequence
<220> FEATURE:
<223> OTHER INFORMATION: siRNA random sense

<400> SEQUENCE: 21
ccuuauaccu aacgacagac ccuuu                                            25

<210> SEQ ID NO 22
<211> LENGTH: 25
<212> TYPE: RNA
<213> ORGANISM: artificial sequence
<220> FEATURE:
<223> OTHER INFORMATION: siRNA random antisense

<400> SEQUENCE: 22
aaagggucug ucguuaggua uaagg                                            25

<210> SEQ ID NO 23
<211> LENGTH: 25
<212> TYPE: RNA
<213> ORGANISM: artificial sequence
<220> FEATURE:
<223> OTHER INFORMATION: siRNA FT1-1 sense

<400> SEQUENCE: 23
ccuccauauc caucaagaca gcuuu                                            25

<210> SEQ ID NO 24
<211> LENGTH: 25
<212> TYPE: RNA
<213> ORGANISM: artificial sequence
<220> FEATURE:
<223> OTHER INFORMATION: siRNA FT1-1 antisense

<400> SEQUENCE: 24
aaagcugucu ugauggauau ggagg                                            25

<210> SEQ ID NO 25
<211> LENGTH: 25
<212> TYPE: RNA
<213> ORGANISM: artificial sequence
<220> FEATURE:
<223> OTHER INFORMATION: siRNA FT1-2 sense

<400> SEQUENCE: 25
cggacuugag agauccuuuc cugaa                                            25

<210> SEQ ID NO 26
<211> LENGTH: 25
<212> TYPE: RNA
<213> ORGANISM: artificial sequence
<220> FEATURE:
<223> OTHER INFORMATION: siRNA FT1-2 antisense

<400> SEQUENCE: 26
uucaggaaag gaucucucaa guccg                                            25

<210> SEQ ID NO 27
```

```
<211> LENGTH: 25
<212> TYPE: RNA
<213> ORGANISM: artificial sequence
<220> FEATURE:
<223> OTHER INFORMATION: siRNA FT2-1 sense

<400> SEQUENCE: 27
cacucugucc cgguuuccuu cagca                                              25

<210> SEQ ID NO 28
<211> LENGTH: 25
<212> TYPE: RNA
<213> ORGANISM: artificial sequence
<220> FEATURE:
<223> OTHER INFORMATION: siRNA FT2-1 antisense

<400> SEQUENCE: 28
ugcugaagga aaccgggaca gagug                                              25

<210> SEQ ID NO 29
<211> LENGTH: 25
<212> TYPE: RNA
<213> ORGANISM: artificial sequence
<220> FEATURE:
<223> OTHER INFORMATION: siRNA FT2-2 sense

<400> SEQUENCE: 29
caucucucuu cugugaagau gcguu                                              25

<210> SEQ ID NO 30
<211> LENGTH: 25
<212> TYPE: RNA
<213> ORGANISM: artificial sequence
<220> FEATURE:
<223> OTHER INFORMATION: siRNA FT2-2 antisense

<400> SEQUENCE: 30
aacgcaucuu cacagaagag agaug                                              25

<210> SEQ ID NO 31
<211> LENGTH: 25
<212> TYPE: RNA
<213> ORGANISM: artificial sequence
<220> FEATURE:
<223> OTHER INFORMATION: siRNA FT3-1 sense

<400> SEQUENCE: 31
ccgcacugcu auuucagcug cuggu                                              25

<210> SEQ ID NO 32
<211> LENGTH: 25
<212> TYPE: RNA
<213> ORGANISM: artificial sequence
<220> FEATURE:
<223> OTHER INFORMATION: siRNA FT3-1 antisense

<400> SEQUENCE: 32
accagcagcu gaaauagcag ugcgg                                              25

<210> SEQ ID NO 33
<211> LENGTH: 25
<212> TYPE: RNA
<213> ORGANISM: artificial sequence
<220> FEATURE:
<223> OTHER INFORMATION: siRNA FT3-2 sense

<400> SEQUENCE: 33
```
cagacacggu caucgugcac cacug                                              25

<210> SEQ ID NO 34
<211> LENGTH: 25
<212> TYPE: RNA
<213> ORGANISM: artificial sequence
<220> FEATURE:
<223> OTHER INFORMATION: siRNA FT3-2 antisense

<400> SEQUENCE: 34
caguggugca cgaugaccgu gucug                                              25

<210> SEQ ID NO 35
<211> LENGTH: 25
<212> TYPE: RNA
<213> ORGANISM: artificial sequence
<220> FEATURE:
<223> OTHER INFORMATION: siRNA FT4-1 sense

<400> SEQUENCE: 35
cgaagccugg caaguaaccu cuuca                                              25

<210> SEQ ID NO 36
<211> LENGTH: 25
<212> TYPE: RNA
<213> ORGANISM: artificial sequence
<220> FEATURE:
<223> OTHER INFORMATION: siRNA FT4-1 antisense

<400> SEQUENCE: 36
ugaagagguu acuugccagg cuucg                                              25

<210> SEQ ID NO 37
<211> LENGTH: 25
<212> TYPE: RNA
<213> ORGANISM: artificial sequence
<220> FEATURE:
<223> OTHER INFORMATION: siRNA FT4-2 sense

<400> SEQUENCE: 37
gcuacaaguu cuaccuggcu uucga                                              25

<210> SEQ ID NO 38
<211> LENGTH: 25
<212> TYPE: RNA
<213> ORGANISM: artificial sequence
<220> FEATURE:
<223> OTHER INFORMATION: siRNA FT4-2 antisense

<400> SEQUENCE: 38
ucgaaagcca gguagaacuu guagc                                              25

<210> SEQ ID NO 39
<211> LENGTH: 25
<212> TYPE: RNA
<213> ORGANISM: artificial sequence
<220> FEATURE:
<223> OTHER INFORMATION: siRNA FT5-1 sense

<400> SEQUENCE: 39
uaggccaggg cuuauggcag uggaa                                              25

<210> SEQ ID NO 40
<211> LENGTH: 25
<212> TYPE: RNA

```
<213> ORGANISM: artificial sequence
<220> FEATURE:
<223> OTHER INFORMATION: siRNA FT5-1 antisense

<400> SEQUENCE: 40
uuccacugcc auaagcccug gccua                                          25

<210> SEQ ID NO 41
<211> LENGTH: 25
<212> TYPE: RNA
<213> ORGANISM: artificial sequence
<220> FEATURE:
<223> OTHER INFORMATION: siRNA FT5-2 sense

<400> SEQUENCE: 41
caucgugcac cacugggaua ucaug                                          25

<210> SEQ ID NO 42
<211> LENGTH: 25
<212> TYPE: RNA
<213> ORGANISM: artificial sequence
<220> FEATURE:
<223> OTHER INFORMATION: siRNA FT5-2 antisense

<400> SEQUENCE: 42
caugauaucc caguggugca cgaug                                          25

<210> SEQ ID NO 43
<211> LENGTH: 25
<212> TYPE: RNA
<213> ORGANISM: artificial sequence
<220> FEATURE:
<223> OTHER INFORMATION: siRNA FT6-1 sense

<400> SEQUENCE: 43
gcugucugac cacgcugcug uuuca                                          25

<210> SEQ ID NO 44
<211> LENGTH: 25
<212> TYPE: RNA
<213> ORGANISM: artificial sequence
<220> FEATURE:
<223> OTHER INFORMATION: siRNA FT6-1 antisense

<400> SEQUENCE: 44
ugaaacagca gcguggucag acagc                                          25

<210> SEQ ID NO 45
<211> LENGTH: 25
<212> TYPE: RNA
<213> ORGANISM: artificial sequence
<220> FEATURE:
<223> OTHER INFORMATION: siRNA FT6-2 sense

<400> SEQUENCE: 45
acacgcggca uagcggcuug guuca                                          25

<210> SEQ ID NO 46
<211> LENGTH: 25
<212> TYPE: RNA
<213> ORGANISM: artificial sequence
<220> FEATURE:
<223> OTHER INFORMATION: siRNA FT6-2 antisense

<400> SEQUENCE: 46
ugaaccaagc cgcuaugccg cgugu                                          25
```

<210> SEQ ID NO 47
<211> LENGTH: 25
<212> TYPE: RNA
<213> ORGANISM: artificial sequence
<220> FEATURE:
<223> OTHER INFORMATION: siRNA FT7-1 sense

<400> SEQUENCE: 47
cgccucaucu gcggguggau gucuu                                              25

<210> SEQ ID NO 48
<211> LENGTH: 25
<212> TYPE: RNA
<213> ORGANISM: artificial sequence
<220> FEATURE:
<223> OTHER INFORMATION: siRNA FT7-1 antisense

<400> SEQUENCE: 48
aagacaucca cccgcagaug aggcg                                              25

<210> SEQ ID NO 49
<211> LENGTH: 25
<212> TYPE: RNA
<213> ORGANISM: artificial sequence
<220> FEATURE:
<223> OTHER INFORMATION: siRNA FT7-2 sense

<400> SEQUENCE: 49
gcgggaacgu uucugugcca ucugu                                              25

<210> SEQ ID NO 50
<211> LENGTH: 25
<212> TYPE: RNA
<213> ORGANISM: artificial sequence
<220> FEATURE:
<223> OTHER INFORMATION: siRNA FT7-2 antisense

<400> SEQUENCE: 50
acagauggca cagaaacguu cccgc                                              25

<210> SEQ ID NO 51
<211> LENGTH: 25
<212> TYPE: RNA
<213> ORGANISM: artificial sequence
<220> FEATURE:
<223> OTHER INFORMATION: siRNA FT8-1 sense

<400> SEQUENCE: 51
caucccaggu cugucgaguu gcuua                                              25

<210> SEQ ID NO 52
<211> LENGTH: 25
<212> TYPE: RNA
<213> ORGANISM: artificial sequence
<220> FEATURE:
<223> OTHER INFORMATION: siRNA FT8-1 antisense

<400> SEQUENCE: 52
uaagcaacuc gacagaccug ggaug                                              25

<210> SEQ ID NO 53
<211> LENGTH: 25
<212> TYPE: RNA
<213> ORGANISM: artificial sequence
<220> FEATURE:

```
<223> OTHER INFORMATION: siRNA FT8-2 sense

<400> SEQUENCE: 53
gagauaucau ugguguggcu ggaaa                                         25

<210> SEQ ID NO 54
<211> LENGTH: 25
<212> TYPE: RNA
<213> ORGANISM: artificial sequence
<220> FEATURE:
<223> OTHER INFORMATION: siRNA FT8-2 antisense

<400> SEQUENCE: 54
uuuccagcca caccaaugau aucuc                                         25

<210> SEQ ID NO 55
<211> LENGTH: 20
<212> TYPE: DNA
<213> ORGANISM: artificial sequence
<220> FEATURE:
<223> OTHER INFORMATION: FUT9 RT-PCR primer U

<400> SEQUENCE: 55
cttaccgccg tgattcagat                                               20

<210> SEQ ID NO 56
<211> LENGTH: 20
<212> TYPE: DNA
<213> ORGANISM: artificial sequence
<220> FEATURE:
<223> OTHER INFORMATION: FUT9 RT-PCR primer L

<400> SEQUENCE: 56
aatgcttgcc cgtaggtatg                                               20

<210> SEQ ID NO 57
<211> LENGTH: 22
<212> TYPE: DNA
<213> ORGANISM: artificial sequence
<220> FEATURE:
<223> OTHER INFORMATION: FUT10 RT-PCR primer U

<400> SEQUENCE: 57
tcggacatct tgtgcccta tg                                             22

<210> SEQ ID NO 58
<211> LENGTH: 20
<212> TYPE: DNA
<213> ORGANISM: artificial sequence
<220> FEATURE:
<223> OTHER INFORMATION: FUT10 RT-PCR primer L

<400> SEQUENCE: 58
tttcagtggc ctccagaact                                               20

<210> SEQ ID NO 59
<211> LENGTH: 20
<212> TYPE: DNA
<213> ORGANISM: artificial sequence
<220> FEATURE:
<223> OTHER INFORMATION: POFUT1 RT-PCR primer U

<400> SEQUENCE: 59
gaaggaagga aacccctttg                                               20
```

```
<210> SEQ ID NO 60
<211> LENGTH: 20
<212> TYPE: DNA
<213> ORGANISM: artificial sequence
<220> FEATURE:
<223> OTHER INFORMATION: POFUT1 RT-PCR primer L

<400> SEQUENCE: 60
tctcccgtct tcaccatttc                                                    20
```

COMBINED PHARMACEUTICAL PREPARATION

RELATED APPLICATION

This application is a national stage filing under 35 U.S.C. §371 of international application PCT/JP2011/074221, filed Oct. 20, 2011, the disclosure of which is incorporated by reference herein in its entirety.

TECHNICAL FIELD

The present invention relates to a combined pharmaceutical preparation with enhanced targeting ability to target cells, a method for treating a disease related to a target cell utilizing the same, and an agent that enhances the target specificity of a targeted medicament and carrier, etc.

BACKGROUND ART

In eucaryote, it has been known that fucosylated sugar chains are involved in various physiological and pathological processes including angiogenesis, reproduction, cell adhesion, inflammation and tumor metastasis (see Non-patent Literature 1). In addition, a number of glycoprotein tumor markers including CA19-9 and SLX are known to be generated by fucosylation of sugar chains (see Non-patent Literature 2). Thus, because fucosylated sugar chains have a significant implication in organisms, if a substance such as a drug can be specifically delivered to cells producing fucosylated sugar chains, then the above-mentioned various phenomena can be controlled. However, to date there has been no report indicating the success of such an attempt.

Furthermore, since fucosylation is catalyzed by a kind of glycosyltransferase, i.e., fucosyltransferase (FUT), one may imagine targeting a fucosyltransferase of fucosylated sugar chain-producing cells as a target molecule; however, this enzyme is a membrane-bound protein localized at regions from the endoplasmic reticulum to the Golgi apparatus, and is not present on the cell surface; accordingly, fucosyltransferases cannot be used as a direct target molecule. Consequently, a technology to deliver a substance such as a drug specifically to fucosylated sugar chain-producing cells has not been developed to date.

CITATION LIST

Patent Literature

Patent Literature 1: JP A 2009-46441
Patent Literature 2: JP A 2004-522722

Non-Patent Literature

Non-patent Literature 1: Ma et al., Glycobiology. 2006; 16(12): 158R-184R.
Non-patent Literature 2: Ma et al., Glycobiology. 1998; 8(6): 605-13.
Non-patent Literature 3: Kawakami et al., Biochem Biophys Acta. 2000; 1524(2-3): 258-65.

SUMMARY OF INVENTION

Problem to be Solved by the Invention

An object of the present invention is to provide a targeted carrier and a targeted medicament with enhanced target specificity, and a method for treating a disease related to target cells utilizing the same, etc.

Means for Solving the Problems

The present inventors have devoted themselves to the research to solve the above problem, and found that there exists in fucosylated molecule-producing cells a mechanism to specifically bind a fucose, and that a carrier comprising fucose as a targeting molecule specifically facilitates the delivery of a substance to fucosylated molecule-producing cells. After performing further research based on this finding, the inventors have found that, by means of concomitant use of mannose that is a ligand for mannose receptor and/or fucose receptor, it is possible to avoid the capture of said carrier in the liver, etc., and to enhance the target specificity; and the inventors have accomplished this invention.

The presence of a mechanism to specifically bind a fucose in fucosylated molecule-producing cells has not at all been known to date. Moreover, although a carrier comprising fucose has been described in Patent Literatures 1 and 2 and Non-patent Literature 3, there has been no teaching that this carrier specifically facilitates the delivery of a substance to fucosylated molecule-producing cells.

Namely, the present invention relates to the following.
(1) A combined pharmaceutical preparation for treating a disease related to a target cell, comprising a first component containing a first ligand for a polyspecific lectin in a reticuloendothelial cell and a second component containing a medicament for treating the disease related to the target cell, wherein the medicament is targeted by a second ligand for a polyspecific lectin in a reticuloendothelial cell, which is different from the first ligand.
(2) The pharmaceutical preparation according to (1), wherein the first component and the second component are administered simultaneously or sequentially.
(3) The pharmaceutical preparation according to (1) or (2), wherein the first ligand is mannose or a compound having terminal mannose, the second ligand is fucose or a molecule having terminal fucose, and the target cell is a fucosylated molecule-producing cell.
(4) The pharmaceutical preparation according to (3), wherein the disease is selected from the group consisting of a neoplastic disease and an inflammatory disease.
(5) The pharmaceutical preparation according to (4), wherein the neoplastic disease is selected from the group consisting of a solid tumor and leukemia.
(6) A combined pharmaceutical composition for specifically delivering a substance to a target cell, comprising a first component containing a first ligand for a polyspecific lectin in a reticuloendothelial cell, and a second component containing a carrier targeted by a second ligand for a polyspecific lectin in a reticuloendothelial cell which is different from the first ligand.
(7) The pharmaceutical composition according to (6), wherein the substance is a label or a drug for treating a disease related to a target cell.
(8) The pharmaceutical composition according to (7), wherein the label is selected from the group consisting of a gas or a substance that generates a gas under physiological conditions, a radioisotope, a magnetic substance, a nuclear magnetic resonance element, a substance that affects the relaxation time of a nuclear magnetic resonance element, a substance that binds to a labeling substance, a fluorescent substance, fluorophore, a chemiluminescent substance, an enzyme, biotin or its derivative, avidin or its derivative, or a substance comprising one or more thereof.

(9) A combined pharmaceutical composition for labeling a target cell or a tissue containing thereof, comprising a first component containing a first ligand for a polyspecific lectin in a reticuloendothelial cell, and a second component containing a labeling agent targeted by a second ligand for a polyspecific lectin in a reticuloendothelial cell which is different from the first ligand.

(10) A kit for treating a disease related to a target cell, comprising one or more containers comprising, singly or in combination, a first component containing a first ligand for a polyspecific lectin in a reticuloendothelial cell and a medicament for treating the disease related to the target cell, wherein the medicament is targeted by a second ligand for a polyspecific lectin in a reticuloendothelial cell which is different from the first ligand.

(11) A target specificity enhancing agent comprising a first ligand for a polyspecific lectin in a reticuloendothelial cell, wherein the agent is for a carrier, a medicament, or a labeling agent, each of which is targeted by a second ligand for a polyspecific lectin in a reticuloendothelial cell which is different from the first ligand.

The present invention also relates to the following.

(i) A carrier targeting fucosylated molecule-producing cells, which comprises an effective amount of fucose for targeting said cells.
(ii) The carrier according to the above (i), wherein the fucose is L-fucose.
(iii) The carrier according to the above (i) or (ii), wherein the fucosylated molecule comprises a type I sugar chain.
(iv) The carrier according to the above (i) or (ii), wherein the fucosylated molecule comprises O-linked fucose.
(v) The carrier according to any one of the above (i)-(iv), wherein the fucosylated molecule-producing cell expresses a fucosyltransferase.
(vi) The carrier according to the above (v), wherein the fucosyltransferase is selected from the group consisting of FUT1, FUT2, FUT3, FUT4, FUT5, FUT6, FUT7, FUT8, FUT9, FUT10, FUT11, POFUT1, and POFUT2.
(vii) The carrier according to any one of the above (i)-(vi), wherein the carrier has a form selected from polymer micelle, liposome, emulsion, microsphere, and nanosphere.
(viii) The carrier according to any one of the above (i)-(vii), wherein the carrier has a form of liposome, and the molar ratio of the fucose to the lipid contained in the liposome is 8:1-1:8.
(ix) A composition comprising the carrier according to any one of the above (i)-(viii) and a drug that controls the activity or growth of fucosylated molecule-producing cells.
(x) The composition according to the above (ix), wherein the drug that controls the activity or growth of fucosylated molecule-producing cells is selected from the group consisting of anti-inflammatory agents and antitumor agents.
(xi) The composition according to the above (ix) or (x), wherein the composition is prepared by mixing the drug and the carrier at a site of clinical practice or its vicinity.
(xii) A composition comprising the carrier according to any one of the above (i)-(viii) and a label.
(xiii) The composition according to the above (xii), wherein the label is selected from the group consisting of a gas or a substance that generates a gas under physiological conditions, a radioisotope, a magnetic substance, a nuclear magnetic resonance atom, a substance that affects the relaxation time of a nuclear magnetic resonance atom, a substance that binds to a labeling substance, a fluorescent substance, a fluorophore, a chemiluminescent substance, an enzyme, biotin or its derivative, avidin or its derivative, or a substance comprising one or more thereof.
(xiv) A preparation kit for the composition according to any one of the above (ix)-(xi), containing one or more containers that contain a drug that controls the activity or growth of fucosylated molecule-producing cells, a fucose donor, and as necessary, a carrier-constitutive substance other than fucose, singly or in a combination thereof.
(xv) A method for treating a disease related to fucosylated molecule-producing cells, comprising administering to a subject in need thereof the composition according to any one of the above (ix)-(xi) in an amount effective for treating said disease.
(xvi) The method according to the above (xv), wherein the disease is selected from the group consisting of neoplastic diseases and inflammatory diseases.
(xvii) The method according to the above (xvi), wherein the neoplastic disease is selected from the group consisting of solid tumors and leukemia.
(xviii) A method for detecting fucosylated molecule-producing cells in a subject, comprising administering to the subject in need thereof the composition according to the above (xii) or (xiii) in an amount effective for the detection.
(xix) The method according to the above (xviii), wherein the cell is detected by imaging.
(xx) The method according to the above (xviii) or (xix), wherein the cell is selected from the group consisting of neoplastic cells and inflammatory cells.
(xxi) A method for diagnosing a disease related to fucosylated molecule-producing cells, comprising administering to a subject in need thereof the composition according to the above (xii) or (xiii) in an amount effective for detection.
(xxii) A method for delivering a substance to fucosylated molecule-producing cells, utilizing the carrier according to any one of the above (i) to (viii).

Advantageous Effects of the Invention

The pharmaceutical preparations and pharmaceutical compositions of the present invention can be specifically delivered to a desired target site more efficiently, since the capture by a reticuloendothelial cell via a polyspecific lectin in the reticuloendothelial cell can be avoided. Furthermore, by blocking polyspecific lectin in the reticuloendothelial cell, the target specificity enhancing agent of the present invention can significantly enhance the ability of a ligand for these receptors in targeting a target other than these lectins, and accordingly, the agent can markedly increase the target specificity of a medicament targeted by such ligand.

Therefore, in the pharmaceutical preparations and pharmaceutical compositions of the present invention, for example, when fucose is used as a targeting ligand, it is possible to achieve desired effects including, for example, suppression of activity and growth of fucosylated molecule-producing cells, and to cure, to inhibit the progression of, or to prevent the onset or recurrence of a disease related to fucosylated molecule-producing cells, with maximum effects and minimum side effects, by means of efficiently transporting desired substances and matters, such as a label or a drug for treating diseases related to fucosylated molecule-producing cells, to fucosylated molecule-producing cells. In addition, when fucose is used as a targeting ligand in the pharmaceutical composition of the present invention, because specific delivery of a substance to fucosylated molecule-producing cells is possible, the present composition can be used for fucosylated molecule-producing cell-specific labeling and gene introduction.

BRIEF DESCRIPTION OF DRAWINGS

FIG. 1 shows secretion of tumor markers and expression of FUT in various pancreatic cancer cell lines. (a) is a graph showing concentrations of CA 19-9, SPAN-1 and DU-PAN-2 in a supernatant of various pancreatic cancer cell line cultures. (b) shows expression states of various fucosyltransferases (FUTs) in various pancreatic cancer cell lines.

FIG. 2 is a graph showing the relationship between the amount of fucose binding and the concentration of free fucose in fucosylated sugar chain high-producing cell line AsPC-1 (upper graph) and in fucosylated sugar chain low-producing cell line PANC-1 (lower graph)

FIG. 3 is a graph showing calculation results of the binding constants Kd and Bmax for fucose of the fucosylated sugar chain high-producing cell line AsPC-1 (upper graph) and of the fucosylated sugar chain low-producing cell line PANC-1 (lower graph), based on the results shown in FIG. 2.

FIG. 4 is a graph showing binding of $^{14}C$ fucose in the fucosylated sugar chain high-producing cell line AsPC-1, and its inhibition by the competition with an excessive amount of non-labeled fucose.

FIG. 5 shows photographs showing introduction of siRNA by fucosylated liposomes with various molar ratios (fucose/liposome).

FIG. 6 shows photographs showing introduction of siRNA by fucosylated liposomes with various molar ratios (fucose/liposome).

FIG. 7 shows photographs showing effects of addition of fucose on the introduction of siRNA by fucosylated liposomes. The photographs indicate the results for non-treatment group, non-fucosylated liposome treatment group, fucosylated liposome treatment group, fucosylated liposome treatment group with addition of an excessive amount of fucose, from the left, respectively.

FIG. 8 shows photographs indicating the comparison of siRNA-introduction efficiency in various pancreatic cancer cell lines. The photographs indicate the results for non-treatment group (upper photos), non-fucosylated liposome treatment group (middle photos), and fucosylated liposome treatment group (lower photos), respectively.

FIG. 9 shows photographs indicating the comparison of siRNA-introduction efficiency in various pancreatic cancer cell lines. The photographs indicate the results for non-treatment group (upper photos), non-fucosylated liposome treatment group (middle photos), and fucosylated liposome treatment group (lower photos), respectively.

FIG. 10 is a graph showing fucosyltransferase-dependent production of CA19-9 in a pancreatic cancer cell line (AsPC-1). (a) shows inhibition of expression of FUT genes by siRNA. (b) shows secretion of CA19-9 in a cell transfected with FUT-siRNA.

FIG. 11 shows a scheme of CDDP encapsulation (inclusion) using CDDP3. (a) and (b) indicate chemical structures of CDDP and CDDP3, respectively. (c) shows CDDP3 in TAPS buffer (pH 8.4) that does not comprise NaCl. (d) indicates CDDP3 in a reversible equilibrium state with coordination of $H_2O$ molecules due to high solubility in water. In the step of (e), CDDP3 is taken up by a liposome, and shows various molecular forms in the liposome. In (f), by changing to TAPS buffer (pH 8.4) that comprises 150 mM of NaCl, chlorine ions flow into the liposome and preferentially form a coordination bond to produce CDDP.

FIG. 12 is a diagram showing preparation of fucosylated liposomes. (a) is a scheme for the preparation of fucosylated liposomes. (b) is an electron micrograph of fucosylated liposomes (the bar represents 100 nm).

FIG. 13 shows graphs representing physiological properties of Cy5.5-included fucosylated liposomes. The average particle size (a) and zeta potential (b) of the liposomes prepared in water were measured by a dynamic light scattering photometer.

FIG. 14 shows photographs showing introduction of Cy5.5 encapsulated in fucosylated liposomes (magnification: 200×).

FIG. 15 shows graphs representing results of flow cytometry of cells treated with Cy5.5-included fucosylated liposomes. AsPC-1 cells (CA19-9 producing cells) (a) and PANC-1 cells (CA19-9 non-producing cells) (b) were treated with Cy5.5-included fucosylated liposomes for 2 hr under the presence (in the figure, +Fuc×100) or absence of excess fucose, and analyzed by flow cytometry.

FIG. 16 shows graphs representing effects of CDDP-encapsulated fucosylated liposomes on various types of pancreatic cancer cell lines. The cells were treated with CDDP-encapsulated fucosylated liposomes for 2 hr, washed, and incubated for 72 hr. Viable cells were measured by WST assay. In (a) and (b), the vertical axis represents "% of control," and the horizontal axis represents μM.

FIG. 17 shows suppression of Cy5.5 accumulation in the liver by mannose treatment. Photographs on the left show distribution of Cy5.5 with mannose treatment (+) and no-treatment (−). Graphs on the right show total flux in the liver calculated using Living images in accordance with manufacturer's instruction.

FIG. 18 shows effects of suppression of Cy5.5 accumulation in the liver by mannose treatment (+). In (a), mannose with an amount 1000 times that of fucose was injected before, after, and simultaneously with the injection of fucosylated liposomes. The vertical axis of the graph represents total flux (photon/sec). (b) is a photograph showing Cy5.5 accumulation in the liver or in the tumor tissue (magnification: 100×).

FIG. 19 shows introduction of Cy5.5 encapsulated by fucosylated liposomes. (a) shows photographs showing introduction of Cy5.5 by fucosylated liposomes (magnification: 100×). AsPC-1 cells were incubated with Cy5.5-encapsulated fucosylated liposomes for 2 hr under the presence (+Man) or absence of mannose, then washed twice with phosphate buffered saline and visualized by a fluorescent microscope. (b) shows results of flow cytometry of cells treated with Cy5.5-encapsulated fucosylated liposomes.

FIG. 20 is a graph showing inhibition of tumor growth by CDDP-encapsulated fucosylated liposomes in a xenograft model. Results are represented by mean±standard deviation (n=6). * indicates a significant difference with p<0.01 compared to NT, CDDP and F0. NT represents no treatment.

FIG. 21 shows apoptotic cells and platinum concentration in tumor cells. (a) shows HE staining (left) and TUNEL staining (right) (magnification: 200×). Tumor tissue was extracted 22 days after treatment. (b) shows platinum concentration in tumor cells treated with CDDP-encapsulated fucosylated liposomes.

FIG. 22 is a graph showing CA19-9 concentrations in a supernatant of various types of colorectal cancer cell line cultures.

FIG. 23 shows photographs showing introduction of Cy5.5 encapsulated in fucosylated liposomes (magnification: 200×).

FIG. 24 shows graphs representing results of flow cytometry of cells treated with Cy5.5-included fucosylated liposomes.

FIG. 25 shows graphs representing effects of fucosylated liposomes that encapsulate CDDP on various types of colorectal cancer cell lines. The cells were treated with CDDP-encapsulated fucosylated liposomes for 2 hr, washed, and incubated for 72 hr. Viable cells were measured by WST assay. The vertical axis of the graphs represents "% of control."

FIG. 26 shows graphs representing effects of fucosylated liposomes that encapsulate CDDP on various types of colorectal cancer cell lines. The cells were treated with CDDP-encapsulated fucosylated liposomes for 2 hr, washed, and incubated for 72 hr. Viable cells were measured by WST assay. The vertical axis of the graphs represents "% of control."

FIG. 27 shows suppression of accumulation of Cy5.5-encapsulated fucosylated liposomes in the liver of LS180 tumor-bearing mice by mannose treatment. Photographs on the left show distribution of Cy5.5 in the mice with mannose treatment (F100+M) or without treatment (F100) on days 2 and 5 after administration of Cy5.5-encapsulated fucosylated liposomes. The graph on the right shows total flux in the liver on day 5 after administration of Cy5.5-encapsulated fucosylated liposomes.

FIG. 28 shows suppression of Cy5.5 accumulation in the liver and promotion of Cy5.5 accumulation in tumor of LS180 tumor-bearing mice by mannose treatment. Photographs on the left show accumulation of Cy5.5 in the liver or tumor tissue of the mannose treatment group (F100+M) or the no-treatment group (F100) (3 mice in each group) on day 14 after treatment. The graph on the right shows total flux (photon/sec) at the tumor site of the mice of the mannose treatment group (F100+M) or the no-treatment group (F100) on day 14 after treatment.

FIG. 29 is a graph showing inhibition of tumor growth in LS180 tumor-bearing mice by CDDP-encapsulated fucosylated liposomes. * indicates that there is a significant difference with $p<0.05$ in the tumor volume between F100-CDDP group and NT/CDDP/F0 groups. There was no significant difference between F100-CDDP and F50-CDDP groups (NS: not significant). NT represents no treatment.

FIG. 30 is a graph showing CA19-9 concentrations in a supernatant of various types of biliary tract cancer cell line cultures.

FIG. 31 shows graphs representing results of flow cytometry of cells treated with Cy5.5-included fucosylated liposomes.

FIG. 32 shows results of flow cytometry of COLO205 cells, i.e., CA19-9 high-producing stomach cancer cell line, treated with Cy5.5-included fucosylated liposomes, as well as fluorescence microscopic images.

FIG. 33 shows results of flow cytometry of MKN45 cells, i.e., CA19-9 non-producing stomach cancer cell line, treated with Cy5.5-included fucosylated liposomes, as well as fluorescence microscopic images.

FIG. 34 shows graphs representing effects of CDDP-encapsulated fucosylated liposomes on CA19-9 high-producing stomach cancer cell line COLO205 cells. The cells were treated with CDDP-encapsulated fucosylated liposomes for 1 hr, washed, and incubated for 72 hr. Viable cells were measured by WST assay.

FIG. 35 shows graphs representing effects of CDDP-encapsulated fucosylated liposomes on CA19-9 non-producing stomach cancer cell line MKN45 cells. The cells were treated with CDDP-encapsulated fucosylated liposomes for 1 hr, washed, and incubated for 72 hr. Viable cells were measured by WST-1 assay.

FIG. 36 is a diagram showing expression of CD33 and Notch-1 in various types of leukemic cell lines.

FIG. 37 is a diagram showing expression of fucosyltransferase in various types of leukemic cell lines.

FIG. 38 shows graphs representing results of flow cytometry of cells of Notch-1 expressing leukemic cell line (HL-60) and Notch-1 non-expressing leukemic cell line (MOLT-4), both treated with fluorescent label-included fucosylated liposomes.

FIG. 39 shows fluorescence microscopic images of Notch-1 expressing leukemic cell line (HL-60) and Notch-1 non-expressing leukemic cell line (MOLT-4), both treated with FAM-included fucosylated liposomes.

FIG. 40 shows graphs representing effects of doxorubicin-encapsulated fucosylated liposomes on cells of Notch-1 expressing leukemic cell line (HL-60) and Notch-1 non-expressing leukemic cell line (MOLT-4). The cells were treated with doxorubicin-encapsulated fucosylated liposomes for 2 hr, washed, and incubated for 72 hr. Viable cells were measured by WST-1 assay.

FIG. 41 is a diagram showing states of expression of CD33 and Notch-1 in samples from leukemia patients.

FIG. 42 is a graph showing effects of doxorubicin-encapsulated fucosylated liposomes on Notch-1 expressing leukemic cells and Notch-1 non-expressing leukemic cells derived from samples of leukemia patients. The cells were treated with doxorubicin-encapsulated fucosylated liposomes for 2 hr, washed, and incubated for 72 hr. Viable cells were measured by WST-1 assay.

DESCRIPTION OF EMBODIMENTS

One aspect of the present invention relates to a combined pharmaceutical preparation for treating a disease related to a target cell, comprising a first component containing a first ligand (may be referred herein to as inhibition ligand, blocking ligand or blockade ligand) for a polyspecific lectin in a reticuloendothelial cell, and a second component containing a drug for treating a disease related to target cells, wherein the drug is targeted by a second ligand (may be referred herein to as ligand for targeting or targeting ligand) for a polyspecific lectin in a reticuloendothelial cell, which is different from the first ligand.

In the present invention, the polyspecific lectin in reticuloendothelial cells includes any polyspecific lectin that is express in reticuloendothelial cells such as splenic sinus endothelial cells, splenic cord reticular cells, lymphoreticular cells, lymphatic endothelial cells, Kupffer cells, liver sinusoidal endothelial cells, bone marrow capillary endothelial cells, monocytes, histiocytes, alveolar macrophages, microglias, macrophages, etc., namely, a lectin having the ability to bins to multiple sugars. Examples of such lectin include, but are not limited to, mannose receptors and fucose receptors.

The mannose receptor refers to a type I transmembrane protein known also as CD206. This receptor is expressed in Kupffer cells, liver sinusoidal endothelial cells, macrophages, Langerhans cells, lymphatic endothelial cells, etc., and is considered to be involved in phagocytosis of pathogens such as bacteria (Kerrigan A M et al, Immunobiology 2009; 214 (7): 562-75, Takahashi et al, Cell Tissue Res 1998; 292 (2): 311-23). This receptor has a C-type lectin-like domain and binds to mannose (Man), fucose (Fuc), N-acetyl glucosamine (GlcNAc) and glucose (Glc), but does not bind to galactose (Gal) (Taylor M E at al, J Biol. Chem 1992; 267 (3) 1719-26). Accordingly, examples of the ligand for mannose receptors include, but are not limited to, mannose, fucose, N-acetyl glucosamine, glucose, any compounds terminated with these sugars, for example, sugar chains terminated with these sugars (such as mannan, dextran, etc.), glycosides of these sugars (such as mannoside, fucoside, glucoside, etc.), derivatives of these sugars (for example, alkylated sugars such as methylated sugars, amino sugars, sugar alcohols, sugar phosphates, glycopetides, glycoproteins, etc.), mannosylated oligolysine (Biessen E A at al, J Biol Chem 1996; 271 (45): 28024-30) anti-mannose receptor antibody (PAM-1 (Am. J. Pathol 1997; 150(3): 929-138), MR5D3 (Serotec, Oxford, UK), etc.), fucosylated. BSA, mannosylated. BSA (Higuchi Y et al, Int J. Pharm 2004; 287 (1-2): 147-54), etc.

Fucose receptors are expressed in Kupffer cells of the liver, etc., and similar to mannose receptors, they are considered to be involved in the phagocytosis of pathogens such as bacteria; a fucose receptor binds to fucose and galactose, but does not bind to mannose (Higuchi at al., supra). Furthermore, it is knows; that binding of fucose to fucose receptors is inhibited by the following various types of sugars: N-acetylgalactosamine, fucose, methyl galactoside, arabinose, galactose, mannose, talose, galactosamine, mannosamine, methyl glucoside, methyl arabinoside, glucose, glucosamine, ribose, methyl mannoside, xylose, altrose, N-acetylmannosamine, allose, methyl glucose, lyxose, glucuronic acid, mannose-6-phosphate, deoxyglucose (Lehrman M A et al., J Biol Chem 1986; 261(16): 7426-32).

Accordingly, examples of a ligand for fucose receptors include, but are not limited to, N-acetylgalactosamine, fucose, methyl galactoside, arabinose, galactose, mannose, talose, galactosamine, mannosamine, methyl glucoside, methyl arabinoside, glucose, glucosamine, ribose, methyl mannoside, xylose, altrose, N-acetyl mannosamine, allose, methyl glucose, xylose, glucuronic acid, mannose-6-phosphate, deoxyglucose, compounds terminated with these sugars, for example, sugar chains terminated with these sugars (such as mannan, dextran, etc glycosides of these sugars (such as fucoside, galactoside, mannoside, glucoside, etc.), derivatives of these sugars (for example, alkylated sugars such as methylated sugars, amino sugars, sugar alcohols, sugar phosphates, glycopeptides, glycoproteins, etc.), various glycosylated BSAs, anti-fucose receptor antibodies and the like.

Whether or not a certain compound is a Ligand for polyspecific lectin in reticuloendothelial cells can be determined by evaluating the binding property of said lectin, for example a mannose receptor or fucose receptor, with said compound. As the evaluation method of such binding property, for example, methods described in the above references (Taylor et al., Biessen at al., Higuchi et al., Lehrman at al., etc.) may be suitably used. Therefore, a compound other than those exemplified above, which has been recognized by such a method to bind to polyspecific lection in reticuloendothelial cells may be included in the ligand of the present invention.

Sugars that can be used as a ligand of the present invention (including those in the form of being bound to other compounds) encompass both L- and D-isomers, as long as they have desired properties (i.e., for the first ligand, binding ability to polyspecific lectin in reticuloendothelial cells, and for the second ligand, binding ability to polyspecific lectin in reticuloendothelial cells and targeting ability). Thus, without limitation, L- and D-mannose, L- and D-fucose, L- and D-N-acetyl glucosamine, L- and D-glucose, and L- and D-galactose, etc. may be included in the ligand of the present invention. In the present invention, one or both of these forms may be used.

Sugars such as mannose, fucose, N-acetyl glucosamine, glucose, galactose, etc. are commercially available or they can be obtained by a known method from various natural sources. Furthermore, methods to modify compounds with mannose, fucose, N-acetyl glucosamine, glucose, galactose, etc. are known in the art (for example, amidination reactions a described in Lee Y C et al, Biochemistry. 1976; 15 (18): 3956-6, and reductive amination as described in Lee R T et al, Biochemistry. 1980; 19 (1): 156-63), and various sugar-modified compounds are commercially available (e.g., various monosaccharide-bound. BSAs commercially available from Dextra Ltd., Reading, UK). Accordingly, those skilled in the art can obtain, purify or synthesize a desired ligand from any of these sources.

The first ligand in the present invention may comprise one or more ligands described above. A ligand or a combination of ligands comprised in the first ligand may bind to any one type, or two or more types, or all types of polyspecific lectins in the reticuloendothelial cells. Of these ligands, the ligand that binds to at least one of mannose receptor or fucose receptor, preferably that binds to both of these receptors is preferred. Examples of the preferable first ligand include, but are not limited to, mannose, fucose, glucose, compounds terminated therewith, combination of N-acetyl glucosamine and galactose, compounds terminated with both of N-acetyl a glucosamine and galactose, combination of a compound terminated with N-acetyl glucosamine and a compound terminated with galactose, etc.

The second ligand of the present invention refers to the above ligands that are different from the first ligand, and that can target at a given target cell. Examples of the second ligand include, but are not limited to, fucose, mannose, galactose, molecules comprising then, such as sugar chains (for example, sugar chains comprising them at the side-chain terminal or at the non-reducing terminal), glycoproteins, glycolipids, etc. Fucose or molecules comprising thereof can target at cells selected from the group consisting of fucosylated molecule-producing cells, cells containing a fucose binding mechanism, and fucosyltransferase-expressing cells. Mannose or molecules comprising thereof can target at cells expressing mannose-binding lectin such as DC-SIGN (Kerrigan et al., supra), for example, dendritic cells, etc. Galactose or molecules comprising thereof can target at cells expressing asialoglycoprotein receptors (Zelensky et al., supra), for example, hepatocytes, etc. (JP B 2007-112768)

When fucose or a molecule comprising thereof is used as the second ligand, one or more substances other than fucose, for example, those selected from the group consisting of the following may be used as the first ligand: mannose, N-acetyl glucosamine, glucose, galactose, N-acetylgalactosamine, methyl galactoside, arabinose, galactose, mannose, talose, galactosamine, mannosamine, methyl glucoside, methyl arabinoside, glucose, glucosamine, ribose, methyl mannoside, xylose, altrose, N-acetyl mannosamine, allose, methyl glucose, lyxose, glucuronic acid, mannose-6-phosphate, deoxyglucose, compounds terminated with these sugars, for example sugar chains terminated with these sugars (such as mannan, dextran, etc.), glycosides of these sugars (such as galactoside, mannoside, glucoside, etc.) derivatives of these sugars (for example, alkylated sugars such as methylated sugars, amino sugars, sugar alcohols, sugar phosphates, glycopeptides and glycoproteins, etc.), various glycosylated BSAs, mannosylated oligolysine, anti-fucose receptor antibodies and anti-mannose receptor antibodies.

Of these, a ligand or a combination of ligands that can bind to both mannose receptor and fucose receptor is preferable, and the examples include, but are not limited to, mannose, glucose, compounds terminated therewith, combination of N-acetylglucosamine and galactose, compounds terminated with both N-acetylglucosamine and galactose, combination of a compound terminated with N-acetylglucosamine and a compound terminated with galactose, combination of ah anti-fucose receptor antibody and an anti-mannose receptor antibody, etc. A particularly preferred first ligand in this embodiment is mannose and/or a compound terminated with mannose.

When mannose or a molecule comprising thereof is used as the second ligand, one or more substances other than mannose, for example, those selected from the group consisting of the following may be used as the first ligand: fucose, N-acetyl glucosamine, glucose, galactose, N-acetylgalactosamine, methyl galactoside, arabinose, galactose, mannose, talose, galactosamine, mannosamine, methyl glucoside, methyl arabinoside, glucose, glucosamine, ribose, methyl mannoside, xylose, altrose, N-acetyl mannosamine, allose, methyl glucose, lyxose, glucuronic acid, mannose-6-phosphate, deoxyglucose, compounds terminated with these sugars, for example sugar chains terminated with these sugars (such as dextran, etc.), glycosides of these sugars (such as galactoside, fucoside, glucoside, etc.), derivatives of these sugars (for example, alkylated sugars such as methylated sugars, amino sugars, sugar alcohols, sugar phosphates, glycopeptides and glycoproteins, etc.), various glycosylated BSAs, anti-fucose receptor antibodies and anti-mannose receptor antibodies.

Of these, a ligand or a combination of ligands that can bind to both mannose receptor and fucose receptor is preferable, and the examples include, but are not limited to, fucose, glucose, compounds terminated therewith, combination of N-acetylglucosamine and galactose, compounds terminated with both N-acetylglucosamine and galactose, combination of a compound terminated with N-acetylglucosamine and a compound terminated with galactose, combination of ah anti-fucose receptor antibody and an anti mannose receptor antibody, etc.

When galactose or a molecule comprising thereof is used as the second ligand, one or more substances other than galactose, for example, those selected from the group consisting of the following may be used as the first ligand: fucose, mannose, N-acetyl glucosamine, glucose, N-acetylgalactosamine, methyl galactoside, arabinose, galactose, mannose, talose, galactosamine, mannosamine, methyl glucoside, methyl arabinoside, glucose, glucosamine, ribose, methyl mannoside, xylose, altrose, N-acetyl mannosamine, allose, methyl glucose, lyxose, glucuronic acid, mannose-6-phosphate, deoxyglucose, compounds terminated with these sugars, for example sugar chains terminated with these sugars (such as mannan, dextran, etc.), glycosides of these sugars (such as mannoside, fucoside, glucoside, etc.), derivatives of these sugars (for example, alkylated sugars such as methylated sugars, amino sugars, sugar alcohols, sugar phosphates, glycopeptides and glycoproteins, etc.), various glycosylated BSAs, mannosylated oligolysine, anti-fucose receptor antibodies and anti-mannose receptor antibodies. Of these, a ligand or a combination of ligands that can bind to both mannose receptor and fucose receptor is preferable, and the examples include, but are not limited to, mannose, fucose, glucose, compounds terminated therewith, combination of an anti-fucose receptor antibody and an anti-mannose receptor antibody, etc.

A cell component targeted by the second ligand, for example a cell surface receptor, may specifically recognize only the second ligand, or may have an affinity to the second ligand higher than that to the first ligand. In the latter case, the cell component targeted by the second ligand has an affinity to the second ligand that is 2-fold or more, 3-fold or more, 4-fold or more, 5-fold or more, 6-fold or more, 7-fold or more, 8-fold or more, 9-fold or more, or 10-fold or more than that to the first ligand. The larger the affinity to the second ligand is, compared to the first ligand, the higher the target specificity of a medicament targeted by the second ligand becomes. The affinity of a ligand to cell components is either known in literatures (for example, Taylor et al., Biessen et al., Higuchi et al., Lehrman et al., Kerrigan et al., etc., supra), or can be experimentally determined by appropriately using a method described in these literatures.

As used herein, "targeting" means to enable a substance such as a medicament, label or carrier to be delivered to a specific target, such as specific cells or tissues (in the present invention, cells having a cell component that recognizes the second ligand or tissues containing such cells) more rapidly, more efficiently and/or in a larger amount than to non-target cells or tissues, compared to the substance which is not targeted, namely, to enable such a substance to be specifically delivered to the target; a targeting agent means a substance that, when it is bound to or reacted with another substance, can make this another substance to be targeted in such a manner. Therefore, the second ligand in the present invention functions as a targeting agent. In addition, target specificity means a degree of rapidness, efficiency, and/or an amount at which a targeted substance such as a medicament, label or carrier is delivered to target cells compared to non-target cells; when target specificity is high, then the targeted substance is delivered to target cells more efficiently, while its delivery to non-target cells is suppressed.

In the present invention, fucosylated molecule-producing cells are not particularly limited as long as they are the cells that produce fucosylated molecules; they may be those comprising fucosylated molecules on their cell surface, or interior of the cells, or they may be those releasing fucosylated molecules outside the cells. Therefore, examples of the fucosylated molecule-producing cells of the present invention include, but are not limited to, cells in tumors, for example, pancreatic tumor, biliary system tumor, liver tumor, digestive tract tumor, brain tumor, lung tumor, bone and soft tissue tumor, hematopoietic organ tumor, more specifically, pancreatic cancer, biliary system cancer, liver cancer, stomach cancer, esophageal cancer, colorectal cancer, and further, breast cancer, lung cancer, endometrial cancer, prostate cancer, leukemia, lymphoma, etc., as well as cells at the site of inflammation in inflammatory diseases such as pancreatitis, cirrhosis, hepatitis, etc., and cells in the immune system such as lymphocytes. Examples of the cells at the site of inflammation include, but are not limited to, cells that are originally present at the site of inflammation and are affected by inflammation. Namely, cells at the site of inflammation refer to, in the case of pancreatitis, constitutive cells of the pancreas affected by the inflammation (ductal cells, exocrine cells, endocrine cells, etc.), and in the case of hepatitis, constitutive cells of the liver affected by the inflammation (hepatocytes, bile duct cells, stellate cells, etc.). Examples of the influence of inflammation include exposure to inflammatory cytokines and contact with inflammatory cells. Examples of leukemia include, but are not limited to, acute myeloid leukemia (AML), acute lymphatic leukemia (ALL), chronic myeloid leukemia (CML), chronic lymphatic leukemia (CLL), etc.

In one embodiment of the present invention, the fucosylated molecule-producing cell is preferably a cell other than normal cells. Examples of such a cell include the above tumor cells and the cells at the site of inflammation.

In the present invention, fucosylated molecules refer to any molecules to which fucose is added, and examples include, but are not limited to, fucosylated sugar chains, fucosylated glycoproteins, fucosylated glycolipids, etc. The number of fucose added is not particularly limited, and it may be 1, or 2 or more. Accordingly, fucosylated glycoproteins and fucosylated glycolipids may, as a sugar moiety, comprise only fucose, or comprise a sugar chain that comprises fucose as a constituent sugar, i.e., a fucosylated sugar chain.

In the present invention, the fucosylated sugar chain may be produced as a single sugar chain, or in a form wherein a sugar chain is bound to other substances. Therefore, the fucosylated sugar chain may be produced in a form of glycoprotein wherein a sugar chain is bound to a protein, or produced in a form of glycolipid wherein a sugar chain is bound to a lipid. Moreover, the fucosylated sugar chain in the present invention may be a sugar chain with any structure as long as it contains fucose; however, those wherein fucose is contained at a non-reducing terminal are preferred. Fucose contained may be L-fucose or D-fucose, and L-fucose is preferable. In addition, the fucosylated sugar chain may comprise a type I carbohydrate antigen (such as CA19-9, SPAN-1, DU-PAN-2, CA50, KMO-1, etc.), or comprise a type II carbohydrate antigen (such as SLX, CSLEX, etc.), or comprise a mother nucleus carbohydrate antigen (such as CA72-4, CA546, STN, etc.). In one embodiment of the present invention, a sugar chain comprising a type I carbohydrate antigen is preferred. In addition, fucosylation may be carried out with various binding modes, for example, α1,2 linkage, α1,3 linkage, α1,4 linkage, and α1,6 linkage, etc. Of these, α1,4 linkage is preferred in the present invention. The sugar chain that is particularly preferred in the present invention includes a carbohydrate antigen selected from the group consisting of CA19-9, SPAN-1, and DU-PAN-2.

The fucosylated glycoprotein in the present invention includes any glycoprotein that comprises fucose in its sugar moiety, and examples include, but are not limited to, Notch receptors (Notch-1, Notch-2, Notch-3, Notch-4, etc.), Notch ligands (Delta-1, Delta-3, Delta-4, Jagged-1, Jagged-2, etc.), haptoglobin, AFP (α fetoprotein)-L3. Fucose may be added to the sugar chain of a glycoprotein, or directly to the protein moiety. The sugar chain of a glycoprotein may have various structures including type I sugar chain, type II sugar chain, mother nucleus sugar chain, and may be O-linked type and N-linked type.

The fucosylated glycolipid in the present invention includes any glycolipid comprising fucose in its sugar moiety, and examples include, but are not limited to, fucosyl GM1. The sugar chain of a glycolipid may have various structures including type I sugar chain, type II sugar chain, and mother nucleus sugar chain.

In one embodiment of the present invention, the fucosylated molecule-producing cell exhibits increased production of fucosylated molecules, compared to normal cells. Here, normal cells refer to, for example, when the subject cell is a tumor cell, the cells of the same type which have not been subjected to tumorigenic transformation; when the subject cell is a cell at a site of inflammation, then refer to the cells of the same type before occurrence of the inflammation or at a site without inflammation. The amount of production of fucosylated molecules can be appropriately measured using, for example, without limitation, an antibody or lectin that recognizes the above carbohydrate antigen. In one embodiment of the present invention, the amount of fucosylated molecules produced by the fucosylated molecule-producing cell is 2 times or more, preferably 5 times or more, more preferably 10 times or more, furthermore preferably 20 times or more, and particularly preferably 50 times or more than that by a normal cell. In another embodiment, the amount of fucosylated molecules produced by the fucosylated molecule-producing cell is larger than that by the cell lines MIAPaCa, PANC-1, KP4, PK45H, HT-29, HCT-15, RBE, OCUG-1, TGBC14TKB, SSP-25, YSCCC, TKKK, HuH-28, MKN45, MKN74, NUGC-4 and/or MOLT-4, and it is equal to or larger than that by the cell lines PK59, ASPC1, SW1116, LS174T, COLO205, LS180, HuCCT1, JR-St, HSC-39, NCI-N87 and/or HL-60.

In another embodiment of the present invention, the fucosylated molecule-producing cell has a fucose binding mechanism. The fucose binding mechanism refers to a mechanism possessed by the cell, with which the cell selectively binds to and/or takes up fucose, and its examples includes, without limitation, cell components such as receptors and transporters. Presence/absence of a fucose binding mechanism can be determined by investigating the binding amount of the fucose detectably labeled with radiolabels, etc., to cells to be examined, as well as its binding constants (see Example 3). For instance, the cell having a fucose binding mechanism exhibits, when measured using the method of Example 3 mentioned below, a binding constant Kd of 25 nM or more, preferably 28 nM or more, more preferably 30 nM or more, and yet more preferably 34 nM or more; and bmax of 5 pmol/$10^6$ cells or more, preferably 7.5 pmol/$10^6$ cells or more, more preferably 10 pmol/$10^6$ cells or more, and yet more preferably 11 pmol/$10^6$ cells or more.

In another embodiment of the present invention, the fucosylated molecule-producing cell expresses a fucosyltransferase. The fucosyltransferase is not particularly limited as long as it transfers fucose from a fucose donor to a fucose acceptor (e.g., sugar chain, polypeptide, lipid, etc.), and it includes, for example, FUT1, FUT2, FUT3, FUT4, FUT5, FUT6 and FUT7, FUT8, FUT9, FUT10 and FUT11 known in the art. In one embodiment of the present invention, the fucosyltransferase is selected from the group consisting of FUT1, FUT2, FUT3, and FUT4. In another embodiment of the present invention, the fucosyltransferase is selected from the group consisting of FUT1, FUT2, FUT4, FUT5, FUT6 and FUT8. In yet another embodiment of the present invention, the fucosyltransferase is selected from the group consisting of FUT1, FUT2, FUT3, FUT4, FUT5, FUT6 and FUT8. In addition, in one embodiment of the present invention, the fucosyltransferase is preferably the one that can transfer fucose via α1,4 linkage, and examples of such fucosyltransferase include FUT3, etc. In one embodiment of the present invention, preferable fucosyltransferase is FUT3 and/or FUT6 that have a strong association with production of CA19-9. In one embodiment of the present invention, the fucosyltransferase is preferably the one that can bind fucose to polypeptide, and examples of such fucosyltransferase include POFUT1, POFUT2, etc. In addition, in one embodiment of the present invention, preferable fucosyltransferase is POFUT1 that has a strong association with fucosylation of Notch-1.

The fucosyltransferase may be expressed during a series of protein expression processes from transcription of genes to maturation of proteins; its expression can be detected at a genetic level and/or protein level. Specifically, at the genetic level, expression can be detected by any known gene expression analysis method including northern blotting, southern blotting, DNA microarray analysis, RNase protection assay, PCR method such as RT-PCR and real-time PCR, etc., in situ hybridization method, and in vitro transcription method, etc.; at the protein level, it can be detected by any known protein detection method including immunoprecipitation, electrophoresis, western blotting, mass spectrometry, EIA, ELISA, RIA, immunohistochemical method and immunocytochemical method, etc. In one embodiment of the present invention, the amount of expression of fucosyltransferase by the fucosylated molecule-producing cell is 2 times or more, preferably 5 times or more, more preferably 10 times or more, yet more preferably 20 times or more, and particularly preferably 50 times or more than that by a normal cell. In addition, in one embodiment of the present invention, the amount of expression of fucosyltransferase by the fucosylated molecule-producing cell is larger than that by the cell lines MIAPaCa, PANC-1, KP4, PK45H, HT-29, HCT-15, RBE, OCUG-1, TGBC14TKB, SSP-25, YSCCC, TKKK, HuH-28, MKN45, MKN74, NUGC-4 and/or MOLT-4, and it is equal to or larger than that by PK59, ASPC1, SW1116, LS174T, COLO205, LS180, HuCCT1, JR-St, HSC-39, NCI-N87 and/or HL-60.

In the present invention, the cell having a fucose binding mechanism refers to cells having the above-described fucose binding mechanism. Details regarding the fucose binding mechanism are as described above. Furthermore, since the fucose binding mechanism is associated with the amount of production of fucosylated molecule and the amount of expression of fucosyltransferase, these can be used as an index of having a fucose binding mechanism. Therefore, in one embodiment of the present invention, the cell having a fucose binding mechanism produces a fucosylated molecule. In addition, in another embodiment of the present invention, the cell having a fucose binding mechanism expresses a fucosyltransferase. Details regarding the production of fucosylated molecule and expression of fucosyltransferase are as described above.

In the present invention, the fucosyltransferase-expressing cell refers to cells expressing the above-described fucosyltransferase. Details regarding the expression of fucosyltransferase are as described above. Since the expression of fucosyltransferase is associated with the production of fucosylated molecule and the presence of fucose binding mechanism, these can be used as an index of fucosyltransferase expression. Accordingly, in one embodiment of the present invention, the fucosyltransferase-expressing cell produces a fucosylated molecule. Also, in another embodiment of the present invention, the fucosyltransferase-expressing cell has a fucose binding mechanism. Details regarding the production of fucosylated molecule and the presence of fucose binding mechanism are as described above.

The medicament in the present invention is a drug for treating a disease related to a target cell (hereinafter, it may be referred to as a pharmaceutical compound), that may be targeted by the second ligand (hereinafter, it may be referred to as a targeted drug or a targeted pharmaceutical compound), or that may be a drug, contained in a carrier targeted by the second ligand (targeted carrier), for treating a disease related to a target cell (hereinafter, it may be referred to as a drug-containing targeted carrier), or that may be a targeted drug contained in a targeted carrier (hereinafter, it may be referred to as a targeted drug-containing targeted carrier).

The targeted drug is not particularly limited as long as the second ligand forms a complex with the drug in such a manner that the second ligand can function as a targeting agent, and it includes those wherein the second ligand binds to the drug directly, or via an intervening chemical element such as a linker or a spacer, in a manner that the second ligand can be in contact with a target cell element. The second ligand can also be designed in the following manner: after the ligand is taken up by a target cell together with the drug, or at the time that the drug is taken up by a target cell, the ligand is separated from the drug and the drug exerts a desired effect. A method to bind sugar or sugar chain to desired compounds is well known. A technique to bind sugar to amino acid, peptide and protein is particularly well known, and these molecules can be used as a linker or spacer (Negre E et al., Antimicrob Agents Chemother. 1992; 36(10): 2228-32).

The targeted carrier is not particularly limited as long as the second ligand forms a complex with the carrier in such a manner that the second ligand can function as a targeting agent, and it includes those wherein the second ligand binds to the carrier directly, or via an intervening chemical element such as a linker or a spacer, in a manner that the second ligand can be in contact with a target cell element. Constituents of the carrier are not particularly limited, and any constituent known in the art of medicine and pharmaceutical may be used; those that can encapsulate or bind to the second ligand are preferable. Examples of such constituent include lipids, for example, phospholipid such as glycerophospholipid, sphingolipid such as sphingomyelin, sterol such as cholesterol, vegetable oil such as soybean oil and poppy seed oil, mineral oil, lecithins such as egg yolk lecithin, polyethylene glycol, PEG:polymer carrier, etc., but they are not limited thereto. Of these, those which can constitute a liposome, for example, natural phospholipid such as lecithin, semi-synthetic phospholipid such as dimyristoyl phosphatidylcholine (DMPC), dipalmitoylphosphatidylcholine (DPPC) and distearoylphosphatidylcholine (DSPC), as well as dioleyl phosphatidylethanolamine (DOPE), dilauroyl phosphatidylcholine (DLPC), and cholesterol are preferable.

Particularly preferable constituents include those which can avoid being trapped by the reticuloendothelial system, for example, cationic lipids such as N-(α-trimethylammonioacetyl)-didodecyl-D-glutamate chloride (TMAG), N,N',N'',N'''-tetramethyl-N,N',N'',N'''-tetrapalmityl spermine (TMTPS), 2,3-dioleyloxy-N-[2(sperminecarboxamide)ethyl]-N,N-dimethyl-1-propanaminium trifluoroacetate (DOSPA), N-[1-(2,3-dioleyloxy)propyl]-N,N,N-trimethyl-ammonium chloride (DOTMA), dioctadecyl dimethyl ammonium chloride (DODAC), didodecyl ammonium bromide (DDAB), 1,2-dioleyloxy-3-trimethylammoniopropane (DOTAP), 3β-[N—(N',N'-dimethylaminoethane)carbamoyl]cholesterol (DC-Chol), 1,2-dimyristoyloxypropyl-3-dimethylhydroxyethyl ammonium bromide (DMRIE), O,O'-ditetradecanoyl-N-(α-trimethylammonioacetyl) diethanolamine chloride (DC-6-14), etc.

Binding or inclusion of a second ligand in the carrier of the invention is also possible by binding or inclusion of the second ligand to other constituents of the carrier by means of chemical and/or physical method. Examples of the method to bind second ligand to carrier include, but are not limited to: a method wherein a liposome is treated to have a hydrophilic property using tris(hydroxyalkyl)aminoalkane, to which a linker protein, for example a protein derived from living organisms such as human serum albumin (HSA) and bovine serum albumin (BSA), is bound, and a sugar chain is bound to the linker protein (WO2007/091661, Hirai et al., Biochem Biophys Res Commun. 2007; 353(3): 553-8, Hirai et al., Int J. Pharm. 2010; 391(1-2): 274-83), a method to prepare liposomes using a sugar-added cholesterol derivative (Patent Literature 1), a method wherein a sugar is added to poly-L-lysine (Negre et al., Supra), a method wherein a liposome is prepared using a glycolipid, or a method wherein p-aminophenyl-D-glycoside is covalently bound to phosphatidylethanolamine liposome using glutaraldehyde (Ghosh P et al., Biochim Biophys Acta. 1980; 632(4): 562-72), a method wherein a liposome is prepared using cholesten-5-yloxy-N-(4-((1-imino-2-β-D-thioglycosylethyl)amino)butyl)formamide (Non-patent Literature 1), and the like. Alternatively, binding or inclusion of a second ligand to the carrier of the invention is possible by mixing the second ligand with other constituents of the carrier at the time of preparing the carrier.

The amount of the second ligand to be bound to or included in the carrier of the invention may be, without limitation, expressed by the weight ratio in the constituents of the carrier, 0.01%-100%, preferably 0.2%-20%, and more preferably 1-5%. Binding or inclusion of the second ligand to/in the carrier of the invention may be carried out before a drug, etc. is supported by the carrier, or by simultaneously mixing the carrier, second ligand, and a drug, or by mixing the carrier which has already supported a drug with the second ligand. Accordingly, the present invention also relates to a process for preparing a drug-containing targeted carrier, which includes a step of binding the second ligand to any existing drug-bound carrier or drug-encapsulated carrier, for example liposomal formulations such as DaunoXome®, Doxil, Caelyx®, Myocet®, etc.

The form of the carrier may be any form, as long as it can deliver a desired substance or matter to target cells, and examples include, but are not limited to, polymer micelle, liposome, emulsion, microsphere, nanosphere, polymer matrix, and lipoplex. In the present invention, from the viewpoints of level of delivery efficiency, range of substances being delivered, easiness of formulation and the like, a liposomal form or lipoplex form is preferable, and a cationic liposome comprising a cationic lipid is particularly preferable. When the carrier is in a liposomal form, the molar ratio of the second ligand to the liposome-constitutive lipid is preferably from 8:1 to 1:8, more preferably from 4:1 to 1:4, yet more preferably from 2:1 to 1:2, and in particular, it is 1:1. In another embodiment, the concentration of the second ligand in the carrier suspension is 5-500 µg/ml, preferably 10-250 µg/ml, more preferably 20-200 µg/ml, and furthermore preferably 25-100 µg/ml.

In the carrier of the present invention, as long as the second ligand contained therein is present in a manner that it can function as a targeting molecule, the carrier may comprise a drug in its interior, or the carrier may be attached to the external of a drug, or the carrier may be mixed with a drug. Here, "function as a targeting molecule" means that the carrier comprising the second ligand reaches and/or is taken up by the target cell more rapidly and/or in an amount larger than that in the carrier without the second ligand; this can be easily confirmed, e.g., by adding to a cell culture a carrier to which a label is attached or that comprises a label, and by analyzing the site of the label after a certain period of time. Structurally, when the second ligand is at least partially exposed external of the formulation comprising the carrier, or the second ligand is present in a form that it can be recognized by a target cell element, at the latest before reaching a target cell, then, the above requirements can be satisfied.

Depending on the route of administration and the manner of drug release, the above medicament may be covered with an appropriate material, such as enteric coating or a material with timed disintegration, or the medicament may be incorporated in an appropriate drug release system.

In the present invention, a drug for treating a disease related to a target cell encompasses any drug that can treat the disease related to the target cell.

When the target cell is a fucosylated molecule-producing cell, the drug for treating a disease related to a target cell includes, without limitation, for example, a drug that controls the activity or growth of fucosylated molecule-producing cells. Here, the activity of fucosylated molecule-producing cells refers to various activities such as secretion, uptake and migration exhibited by said cells; in the case of tumor cells for example, it refers to activities involved in the onset, progression, recurrence and/or metastasis of tumors, and appearance and worsening of symptoms such as cachexia. Such activities include, but are not limited to, production and secretion of parathyroid hormone-related protein (PTHrP) and immunosuppressive acidic protein (IAP).

Therefore, the drug that controls activity or growth of fucosylated molecule-producing cells may be any drug that directly or indirectly suppresses physical, chemical and/or physiological actions, etc. of fucosylated molecule-producing cells related to the onset, progression and/or recurrence of diseases related to fucosylated molecule-producing cells. For example, in the case of tumor cells, such drugs include, without limitation, drugs that inhibit activity or production of the above physiologically active substance, for example an antibody and an antibody fragment that neutralizes the physiologically active substance, a substance that suppresses expression of the physiologically active substance, such as RNAi molecules (for example, siRNA, shRNA, ddRNA, miRNA, piRNA, rasiRNA, etc.), ribozyme, and antisense nucleic acids (including RNA, DNA, PNA and a complex thereof), or a substance that has a dominant negative effect such as a dominant negative mutant, etc., or a vector expressing them, a cell activation inhibitor such as sodium channel inhibitor, cell growth inhibitors, such as an alkylating agent (e.g., ifosfamide, nimustine, cyclophosphamide, dacarbazine, melphalan, ranimustine etc.), an antitumor antibiotic (e.g., idarubicin, epirubicin, daunorubicin, doxorubicin, pirarubicin, bleomycin, peplomycin, mitoxantrone, mitomycin C, etc.), and an antimetabolite (e.g., gemcitabine, enocitabine, cytarabine, tegafur uracil, tegafur gimeracil oteracil potassium formulation, doxifluridine, hydroxycarbamide, fluorouracil, methotrexate, mercaptopurine, etc.); as well as apoptosis-inducing agents, such as compound 861 and gliotoxin. Furthermore, "the drug that controls activity or growth of fucosylated molecule-producing cells" in the present invention may be any drug that directly or indirectly accelerates physical, chemical and/or physiological actions, etc. of fucosylated molecule-producing cells directly or indirectly related to the suppression of the onset, progression, and/or recurrence of diseases related to fucosylated molecule-producing cells.

Examples of the drug that controls activity or growth of fucosylated molecule-producing cells also include substances that suppress production of fucosylated molecules, for example, an antibody and an antibody fragment that inhibit functions of fucosyltransferase, a substance that suppresses expression of fucosyltransferase such as RNAi molecules (e.g., siRNA, shRNA, ddRNA, miRNA, piRNA, rasiRNA, etc.), ribozyme and antisense nucleic acids (including RNA, DNA, PNA, and a complex thereof), or a substance that has a dominant negative effect such as a dominant negative mutant, etc., or a vector expressing them. Examples of fucosyltransferase include FUT1, FUT2, FUT3, FUT4, FUT5, FUT6, FUT7, and FUT8, etc., and examples of siRNA sequences corresponding thereof include those listed in Table 2 below. Other examples of fucosyltransferase include FUT9, FUT10, FUT11, POFUT1 and POFUT2, etc.

In one embodiment of the present invention, fucosyltransferase to be inhibited is selected from the group consisting of FUT1, FUT2, FUT3 and FUT4. In another embodiment of the present invention, fucosyltransferase is selected from the group consisting of FUT1, FUT2, FUT4, FUT5, FUT6 and FUT8. In yet another embodiment of the present invention, fucosyltransferase is selected from the group consisting of Fuli, FUT2, FUT3, FUT4, FUT5, FUT6 and FUT8. In addition, in one embodiment of the present invention, fucosyltransferase to be inhibited is preferably the one that can transfer fucose via al, 4 linkage, and examples of such fucosyltransferase include FUT3, etc. In one embodiment of the present invention, fucosyltransferase to be inhibited is FUT3 and/or FUT6 that have a strong association with production of CA19-9. In another embodiment of the present invention, fucosyltransferase to be inhibited is preferably the one that can bind fucose to polypeptide, and examples of such fucosyltransferase include POFUT1, POFUT2, etc. In addition, in one embodiment of the present invention, fucosyltransferase to be inhibited is POFUT1 that has a strong association with fucosylation of Notch-1.

The disease related to fucosylated molecule-producing cells includes not only a disease caused by fucosylated molecule-producing cells, but also a disease affecting said cells, and examples include, without limitation, neoplastic diseases including tumors such as pancreatic tumor, biliary system tumor, liver tumor, digestive tract tumor, brain tumor, lung tumor, bone and soft tissue tumor, hematopoietic organ tumor, more specifically, for example, pancreatic cancer, biliary system cancer, liver cancer, stomach cancer, esophageal cancer, colorectal cancer, and further, breast cancer, lung cancer, endometrial cancer, prostate cancer, leukemia, lymphoma, etc., as well as inflammatory diseases such as pancreatitis, cirrhosis, hepatitis, etc. In addition, because Notch is activated in endothelial cells, fibroblast cells and keratinocytes which are involved in wound healing (Chigurupati et al., PLoS One. 2007 Nov. 14; 2(11): e1167), the disease related to fucosylated molecule-producing cells also includes wound.

Accordingly, the drug for treating diseases related to fucosylated molecule-producing cells include for example, but are not limited to, antitumor agents that suppress the onset, progression and/or recurrence of neoplastic diseases, for example, without limitation, alkylating agents such as ifosfamide, nimustine (e.g., nimustine hydrochloride), cyclophosphamide, dacarbazine, melphalan, ranimustine, etc., antimetabolites such as gemcitabine (e.g., gemcitabine hydrochloride), enocitabine, cytarabine ocfosfate, cytarabine preparation, tegafur uracil, tegafur gimeracil oteracil potassium formulation (e.g., TS-1), doxifluridine, hydroxycarbamide, fluorouracil, methotrexate, mercaptopurine, etc., antitumor antibiotics such as idarubicin (e.g., idarubicin hydrochloride), epirubicin (e.g., epirubicin hydrochloride), daunorubicin (e.g., daunorubicin hydrochloride, daunorubicin citrate), doxorubicin (e.g., doxorubicin hydrochloride), pirarubicin (e.g., pirarubicin hydrochloride), bleomycin (e.g., bleomycin hydrochloride), peplomycin (e.g., peplomycin sulfate), mitoxantrone (e.g., mitoxantrone hydrochloride), mitomycin C, etc., alkaloids such as etoposide, irinotecan (e.g., irinotecan hydrochloride), vinorelbine (e.g., vinorelbine tartrate), docetaxel (e.g., docetaxel hydrate), paclitaxel, vincristine (e.g., vincristine sulfate), vindesine (e.g., vindesine sulfate), vinblastine (e.g., vinblastine sulfate), etc., hormone therapy agents such as anastrozole, tamoxifen (e.g., tamoxifen citrate), toremifene (e.g., toremifene citrate), bicalutamide, flutamide, estramustine (e.g., estramustine phosphate), etc., platinum complexes such as carboplatin, cisplatin (CDDP), nedaplatin, etc., angiogenesis inhibitors such as thalidomide, Neovastat, bevacizumab, etc., and L-asparaginase and the like.

Examples of the drug for treating diseases related to fucosylated molecule-producing cells may further include, but are not limited to, anti-inflammatory agents that suppress the onset, progression and/or recurrence of inflammatory diseases, for example, steroidal anti-inflammatory agents (prednisolone, beclomethasone, betamethasone, fluticasone, dexamethasone, hydrocortisone, etc.) and non-steroidal anti-inflammatory agents (acetylsalicylic acid, loxoprofen, acetaminophen, ketoprofen, tiaprofenic acid, suprofen, tolmetin, carprofen, benoxaprofen, piroxicam, benzydamine, naproxen, diclofenac, ibuprofen, diflunisal, azapropazone, etc.), substances that suppress expression of inflammatory cytokines such as RNAi molecules (e.g., siRNA, shRNA, ddRNA, miRNA, piRNA, rasiRNA, etc.) and antisense nucleic acids, and/or drugs that suppress action of inflammatory cytokines, such as antibodies against inflammatory cytokines, receptor antagonists of inflammatory cytokines, etc.

When the target cell is a dendritic cell, examples of a disease related to a target cell include, but are not limited to, various immunological diseases, for example, allergies, immunodeficiency, infectious diseases, tumors, cancers, etc. Accordingly, examples of the drug for treating a disease related to a target cell includes, but are not limited to immunosuppressants such as steroids, azathiopine, mercaptopurine and cyclosporine, antigens, nucleic acid vaccines such as DNA vaccines, etc., and NFκB decoy.

When the target cell is a hepatocyte, examples of a disease related to a target cell include, but are not limited to, liver cancer, infectious diseases, e.g., viral hepatitis such as infection and HCV infection, hepatocytes dysfunctions, such as hyperlipidemia and enzyme deficiencies, as well as diseases that can be cured by the introduction and expression of genes in hepatocytes, for exam diabetes, ADA deficiency and hemophilia, etc. Accordingly, a drug for treating a disease related to a target, cell varies depending on the disease, but the examples include, without limitation, anti-cancer agents, RNAi molecules that suppress the express ion of viral genes (such as siRNA, shRNA, ddRNA, miRNA, piRNA rasiRNA, etc.), ribozymes, antisense nucleic acids (including RNA, DNA, PNA, or complexes thereof), apolipoprotein B gene, HMG-CoA reductase gene, insulin gene, adenosine deaminase gene, factor III gene, factor IX gene, and vectors to express such nucleic acid molecules.

Preferably, the drug for treating a disease related to a target cell is delivered to the interior of a target cell; however, depending on the situation, in some cases delivery to the periphery of a target cell may be preferred. For example, when the target cell is a fucosylated molecule-producing cell, substances that suppress expression of inflammatory cytokines such as siRNA molecules and antisense nucleic acids can also be delivered to inflammatory cytokine-producing cells that do not produce fucosylated molecules, thereby enabling more effective treatment of diseases related to fucosylated molecule-producing cells such as pancreatitis and hepatitis.

The drug for treating a disease related to a target cell may be or may not be labeled. By means of labeling, success/failure of delivery and increase/decrease of target cells can be monitored, and it is particularly useful at investigation and research levels.

In the present specification, a label refers to any substance, wherein, the substance itself or a matter to which the substance is attached can be detected directly or indirectly. A label may be selected from substances known by those skilled in the art, for example, gas or substances that generate gas under physiological conditions, any radioisotopes, magnetic materials, nuclear magnetic resonance elements (e.g., hydrogen, phosphorus, sodium, fluorine, etc.), substances that affect relaxation time of nuclear magnetic resonance elements (e.g. metal atom or compound comprising thereof), substances that binds to a labeling substance (e.g., antibody), fluorescent materials, fluorophores, chemiluminescent substances, enzymes, biotin or its derivatives, avidin or its derivatives.

In the present specification, a label may be a detectable label, which includes any labels that can be detected by any existing detection means. Examples of detection method include, but are not limited to, naked eye, optical examination apparatus (e.g., optical microscope, fluorescence microscope, phase contrast microscope, in vivo imaging apparatus, etc.), X-ray apparatus (e.g., plain X-ray apparatus, computed tomography (CT) apparatus, etc.), magnetic resonance imaging (MRI) apparatus, nuclear medicine apparatus (e.g., scintigraphic apparatus, positron emission tomography (PET) apparatus, single photon emission computed tomography (SPECT) apparatus, etc.), ultrasonographic apparatus and thermographic apparatus, etc. Labels suitable for each detection means are known to a person skilled in the art, and described, for example, in Lecchi et al., Q J Nucl Med Mol. Imaging. 2007; 51(2): 111-26.

Examples of labels suitable for detection by naked eye and optical examination apparatus include various fluorescent labels and luminescent labels.

Specific fluorescent labels which may be used include, but are not limited to, Cy™ series (e.g., Cy™ 2, 3, 5, 5.5, 7, etc.), DyLight™ series (e.g., DyLight™ 405, 488, 549, 594, 633, 649, 680, 750, 800, etc.), Alexa Fluor® series (e.g., Alexa Fluor® 405, 488, 549, 594, 633, 647, 680, 750, etc.), HiLyte Fluor™ series (e.g., HiLyte Fluor™ 488, 555, 647, 680, 750, etc.), ATTO series (e.g., ATTO 488, 550, 633, 647N, 655, 740, etc.), FAM, FITC, Texas-Red, GFP, RFP, and Qdot. Fluorescent labels suitable for in vivo imaging are, for example, those emit a fluorescence of wavelength that is highly transmissive through living body and less susceptible to autonomous fluorescence, such as a fluorescence of near-infrared wavelength, or those exhibit strong fluorescent intensity. Such fluorescent labels include, but are not limited to, Cy™ series, DyLight™ series, Alexa Fluor® series, HiLyte Fluor™ series, ATTO series, Texas-Red, GFP, RFP, Qdot and derivatives thereof.

Specific luminescent labels which may be used include, but are not limited to, for example, luminol, luciferin, lucigenin and aequorin, etc.

Suitable labels for detection by X-ray apparatus include, for example, various contrast agents. Specific contrast agents which may be used include, but are not limited to, iodine atoms, iodine ions and iodine-containing compounds, etc.

Suitable labels for detection by MRI apparatus include, for example, nuclear magnetic resonance elements and substances that affect relaxation time of nuclear magnetic resonance elements. Examples of the nuclear magnetic resonance elements include hydrogen, phosphorus, sodium, fluorine, etc. Examples of the substances that affect relaxation time of nuclear magnetic resonance elements include, but are not limited to, various metal atoms, or a compound comprising said metal atom(s), for example, complexes of said metal atom(s). Specific examples that may be used include, but are not limited to, gadolinium(III) (Gd(III)), yttrium-88 ($^{88}$Y), indium-111 ($^{111}$In), complexes of such metal atom(s) and a ligand such as diethylenetriaminepentaacetic acid (DTPA), tetraazacyclododecane-1,4,7,10-tetraacetic acid (DOTA), (1,2-ethanediyldinitrilo)tetraacetic acid (EDTA), ethylenediamine, 2,2'-bipyridine (bipy), 1,10-phenanthroline (phen), 1,2-bis(diphenylphosphino)ethane (DPPE), 2,4-pentanedione (acac), and oxalate (ox), as well as super-paramagnetic iron oxide (SPIO) and manganese oxide (MnO).

Suitable labels for detection by nuclear medicine apparatus include, for example, various radioisotopes, and compounds comprising said radioisotope(s), such as complexes of said radioisotope(s). Radioisotopes which may be used include, but are not limited to, e.g., technetium-99m ($^{99m}$Tc), indium-111 ($^{111}$In), iodine-123 ($^{123}$I), iodine-124 ($^{124}$I), iodine-125 ($^{125}$I), iodine-131 ($^{131}$I), thallium-201 ($^{201}$Tl), carbon-11 ($^{11}$C), nitrogen-13 ($^{13}$N), oxygen-15 ($^{15}$O), fluorine-18 ($^{18}$F), copper-64 ($^{64}$Cu), gallium-67 ($^{67}$Ga), krypton-81m ($^{81m}$Kr), xenon-133 ($^{133}$Xe), strontium-89 ($^{89}$Sr) and yttrium-90 ($^{90}$Y). Compounds comprising a radioisotope include, but are not limited to, e.g., $^{123}$I-IMP, $^{99m}$Tc-HMPAO, $^{99m}$Tc-ECD, $^{99m}$Tc-MDP, $^{99m}$Tc-tetrofosmin, $^{99m}$Tc-MIBI, $^{99m}$TcO$_4$—, $^{99m}$Tc-MAA, $^{99m}$Tc-MAG3, $^{99m}$Tc-DTPA, $^{99m}$Tc-DMSA, $^{18}$F-FDG1, etc.

Suitable labels for detection by ultrasonographic apparatus which may be used include, but are not limited to, bio-acceptable gases or substances that generate gas under physiological conditions, fatty acids, or substances comprising thereof. Examples of the gas include, but are not limited to, air, noble gas, nitrogen, N$_2$O, oxygen, carbon dioxide, hydrogen, inert noble gas (e.g., helium, argon, xenon or krypton), sulfur fluoride (e.g., sulfur hexafluoride, disulfur decafluoride, trifluoromethyl sulfur pentafluoride), selenium hexafluoride, silane halides (e.g., tetramethylsilane), low-molecular-weight hydrocarbon (e.g., C$_{1-7}$ alkane (methane, ethane, propane, butane, pentane, etc.), cycloalkane (cyclobutane, cyclopentane, etc.), alkene (ethylene, propene, butene, etc.)), fluorine-containing gas, ammonia, etc.; examples of substances that generate gas under physiological conditions include, but are not limited to, dodecafluoropentane (DDFP), perfluorocarbon vaporized under physiological conditions (JP A 2010-138137); examples of substances comprising the above substances include nanoparticles and liposomes. Examples of fluorine-containing gas include, but are not limited to, halogenated hydrocarbon gas (e.g., bromochlorodifluoromethane, chlorodifluoromethane, dichlorodifluoromethane, bromotrifluoromethane, chlorotrifluoromethane, chloropentafluoroethane, dichlorotetrafluoroethane, perfluorocarbon), fluorinated ketone (e.g., perfluoroacetone), fluorinated ether (e.g., perfluoro-diethyl ether).

Examples of perfluorocarbon include, but are not limited to, perfluoroalkane (e.g., perfluoromethane, perfluoroethane, perfluoropropane, perfluorobutane, perfluoro-n-butane, perfluoropentane, perfluorohexane, perfluoroheptane), perfluoroalkene (e.g., perfluoropropene, perfluorobutene (e.g., perfluorobut-2-ene), perfluorobutadiene), perfluoroalkyne (e.g., perfluorobut-2-yne), perfluorocycloalkane (e.g., perfluorocyclobutane, perfluoromethylcyclobutane, perfluorodimethylcyclobutane, perfluorotrimethylcyclobutane, perfluorocyclopentane, perfluoromethylcyclopentane, perfluorodimethylcyclopentane, perfluorocyclohexane, perfluoromethylcyclohexane, perfluorocycloheptane), etc.

As suitable labels for detection by ultrasonographic apparatus, those already commercially available may also be used. Examples of commercially available labels for ultrasonographic detection include, but are not limited to, those of the first generation such as Albunex (Mallinckrodt), Echovist (SHU 454, Schering), Levovist (SHU 508, Schering), Myomap (Quadrant), Quantison (Quadrant), Sonavist (Schering), Sonazoid (GE Healthcare), etc., those of the second generation such as Definity/luminity (Bristol-Myers Squibb Medical Imaging), Imagent-imavist (Alliance), Optison (GE Healthcare), biSphere/cardiosphere (POINT Biomedical), SonoVue (BR1, Bracco), AI700/imagify (Acusphere), etc., those of the third generation such as Echogen (Sonus Pharmaceuticals), etc. (Reddy et al., World J. Gastroenterol. 2011 Jan. 7; 17(1):42-8). In addition, suitable labels for detection by ultrasonographic apparatus other than those mentioned above are described in JP A 5-194278, JPA 8-310971, JP A 8-151335, JP A 2002-308802, WO 2004/069284, WO 2005/120587, etc.

In the present invention, "for a target cell" means that the carrier or medicament can suitably be used to target the target cell; for example, the carrier or medicament is delivered to the target cell more rapidly, with higher efficiency and/or in a larger amount, compared to a non-target cell. For instance, the targeted drug or targeted carrier of the invention can be delivered to a target cell at a rate and/or efficiency of 1.1 times or more, 1.2 times or more, 1.3 times or more, 1.5 times or more, 2 times or more, and furthermore, 3 times or more, compared to a non-target cell.

The first component comprising a first ligand and the second component comprising a medicament targeted by a second ligand may be present in any ratio in the combined pharmaceutical preparation of the present invention, as long as the first component enhances the target specificity of the second component; those skilled in the art can appropriately determine the suitable ratio by the following method, for example: to a subject such as an experimental animal, either a predetermined amount of the labeled second component and a varying amount of the first component relative to the second component, or a predetermined amount of the first component and a varying amount of the labeled second component relative to the first component, are administered, then the amount of the label in the target tissue or cells is measured. For example, when mannose is used as the first ligand and fucose is used as the second ligand, the ratio of mannose to fucose is, for example when represented by a mass ratio, 20000:1-200:1, 10000:1-300:1, 5000:1-500:1, 3000:1-1000:1, 2500:1-1500:1; when represented by a molar ratio, 16000:1-160:1, 8000:1-240:1, 4000:1-400:1, 2400:1-500:1, 2000:1-1200:1, etc. In addition, when mannose is used as the first ligand, the dosage of the first component may be, in terms of mannose per 1 administration, 0.01-10000 mg/kg body weight, 0.1-1000 mg/kg body weight, 0.5-500 mg/kg body weight, 1-100 mg/kg body weight, 5-50 mg/kg body weight, or 0.05-50000 µmole/kg body weight, 0.5-5000 µmole/kg body weight, 2.5-2500 µmole/kg body weight, 5-500 µmole/kg body weight, 25-250 µmole/kg body weight, etc.

In the combined pharmaceutical preparation of the present invention, the first component and the second component can be administered simultaneously or sequentially. Accordingly, the first component may be administered simultaneously with the second component, administered before the second component, or administered after the second component. In the case of sequential administration of the first component and the second component, the second component may be administered sequentially and immediately after the first component, the first component may be administered sequentially and immediately after the second component, the second component may be administered with a certain time interval after administration of the first component, the first component may be administered with a certain time interval after administration of the second component, or a combination thereof may be adopted. Therefore, for example, following the administration of the first component, the first and second components may be simultaneously administered after a certain time interval, then the first component may be administered after a further time interval. The time interval may be within 48 hr, within 36 hr, within 24 hr, within 12 hr, within 6 hr, within 5 hr, within 4 hr, within 3 hr, within 2 hr, within 1 hr, within 30 min, within 15 min, or within 10 min, etc. Those skilled in the art can appropriately determine the time interval as follows, for example: first and second components are administered to a subject such as an experimental animal with various sequences and time intervals, then the amount of label in target tissue or cells is measured.

The combined pharmaceutical preparation of the present invention may be in a single dosage form when the first and second components are simultaneously administered, or the first component and the second component may be in separate dosage forms. When the first and second components are not administered simultaneously, needless to say, the first component and the second component should be in separate dosage forms. In the case where, in addition to simultaneous administration of the first and second components, the first component is further administered at different timing, then the first component and the second component may be in separate dosage forms, or in a combination of a single dosage form containing the first and second components and a separate dosage form containing the first component alone. In the case where the first component and the second component are in separate dosage forms, the first component may be supplied in the same package with the second component, or each component may supplied in a separate package. Furthermore, the combined pharmaceutical preparation of the present invention may further comprise instructions showing a method of combined use of first and second components, for example, an instruction leaflet, or a recording medium containing information on the method of use such as flexible disk, CD, DVD, blue ray disk, memory card, USB memory, etc.

Another aspect of the present invention relates to a combined pharmaceutical composition for specifically delivering a substance to a target cell, comprising a first component containing a first ligand for a polyspecific lectin in a reticuloendothelial cell and a second component containing a carrier targeted by a second ligand for a polyspecific lectin in a reticuloendothelial cell which is different from the first ligand.

In this aspect of the present invention, reticuloendothelial cell, polyspecific lectin, first ligand, second ligand, targeting, carrier, ratio of first component to second component, and administration sequence are as described above for the combined pharmaceutical preparation of the present invention. However, the substance to be delivered by the combined pharmaceutical composition of the invention is not limited to a drug for treating diseases related to target cells, and includes any substance having a size that can be physically transferred in the body of an organism from the administration site to the site of lesion where the target cell is present. Accordingly, the pharmaceutical composition of the present invention can transport not only substances such as atoms, molecules, compounds, proteins, nucleic acids, etc., but also vectors, viral particles, cells, drug release systems composed of one or more elements, micromachines, etc. The above substances preferably have a characteristic to influence target cells and/or their periphery, and they include, for example, those which can label target cells, or can control (for example, enhance or suppress) the activity or growth of target cells and/or cells present in their periphery.

In one embodiment of the present invention, the substance to be delivered is a label and/or a drug for treating a disease related to a target cell, described above regarding the combined pharmaceutical preparation of the present invention.

Another aspect of the present invention relates to a combined pharmaceutical composition comprising a first component containing a first ligand for a polyspecific lectin in a reticuloendothelial cell and a second component containing a labeling agent targeted by a second ligand for a polyspecific lectin in a reticuloendothelial cell which is different from the first ligand, for labeling a target cell or tissue containing thereof (hereinafter, this may be referred to as target tissue); for detecting the target cell or the tissue containing thereof; for imaging the target cell or the tissue containing thereof; for diagnosing, detecting and/or monitoring a disease related to the target cell; for detecting the possibility of a disease related to a target cell; and/or for evaluating effects of treatment for a disease related to a target cell (hereinafter, this may be referred to as a label-containing composition).

In this aspect of the present invention, reticuloendothelial cell, polyspecific lectin, first ligand, second ligand, targeting, ratio of first component to second component, and administration sequence are as described above for the combined pharmaceutical preparation of the present invention. Here, the labeling agent may be composed of only a label targeted by the second ligand, or may be a label supported by the carrier that is targeted by the second ligand, or may be a label targeted by the second ligand that is supported by the carrier targeted by the second ligand. The label is as described above for the combined preparation of the present invention.

Examples of the tissue containing target cells include the following without limitation: in cases where the target cell is a fucosylated molecule-producing cell, tumor tissues, for example, tissues of pancreatic tumor, biliary system tumor, liver tumor, digestive tract tumor, brain tumor, lung tumor, bone and soft tissue tumor, hematopoietic organ tumor, more specifically, pancreatic cancer, biliary system cancer, liver cancer, stomach cancer, esophageal cancer, colorectal cancer, and further, breast cancer, lung cancer, endometrial cancer, prostate cancer, lymphoma, etc., as well as bone-marrow tissues affected by leukemia, tissues at the site of inflammation in inflammatory diseases such as pancreatitis, cirrhosis, hepatitis, etc., and tissues in the immune system such as the lymphatic system, and dermal tissues affected by wound, etc.; in cases where the target cell is a dendritic cell, for example, skin, nasal cavity, lung, gastrointestinal tract, etc.; and in cases where the target cell is a hepatocyte, examples include liver, etc.

Labeling and detection (including imaging) of the target cell or the tissue containing the target cell may be carried out in vivo or in vitro. Furthermore, said composition may comprise the label in an effective amount for labeling the target cell or the tissue containing the target cell, for detecting the target cell or the tissue containing the target cell, for imaging in vivo or in vitro the target cell or the tissue containing the target cell, for diagnosing, detecting and/or monitoring a disease related to the target cell, for detecting the possibility of a disease related to the target cell, or for evaluating effects of a treatment for a disease related to the target cell. Said effective amount may be, e.g., an amount that is taken into the target cell to a degree that the label can be detected in vivo or in vitro. In addition, an amount that does not cause an adverse effect exceeding the benefit from the administration is preferred. Such an amount can be appropriately determined by in vitro tests using culture cells, or by tests using a model animal such as a mouse, rat, dog or pig, and such test methods are well known to those skilled in the art. Said composition may comprise, in addition to a labeling agent, any drug such as the above-described drug that controls the activity or growth of a target cell, and the drug that treats a disease related to a target cell, etc.

Another aspect of the present invention relates to a target specificity enhancing agent comprising a first ligand for a polyspecific lectin in a reticuloendothelial cell, wherein the agent is for a carrier, a medicament, or a labeling agent, each of which is targeted by a second ligand for a polyspecific lectin in a reticuloendothelial cell which is different from the first ligand (hereinafter, each of which may be abbreviated as a targeted carrier, etc.).

In this aspect of the present invention, reticuloendothelial cell, polyspecific lectin, first ligand, second ligand, targeting, carrier, medicament, labeling agent, target specificity are as described above for the combined pharmaceutical preparation and combined pharmaceutical composition of the present invention.

The target specificity enhancing agent of the present invention enhances the target specificity of the above-mentioned carrier etc. that is targeted by the second ligand. Namely, target specificity of the carrier etc. that is targeted by the second ligand is increased by the use of the target specificity enhancing agent of the invention, compared to the case wherein said agent is not used. A degree of target specificity can be evaluated as follows: the target specificity enhancing agent of the present invention and the carrier etc. that is targeted by the second ligand are administered to a subject, such as an experimental animal, then a difference in the distribution between the target cells and non-target cells, or therapeutic effect, etc. are compared with the difference in the distribution, or the therapeutic effect, etc. of the case wherein the carrier, etc. that is targeted by the second ligand is not used in combination with the target specificity enhancing agent of the invention. For example, without limitation, when the ratio of the distribution in target cells to that in non-target cells, wherein the carrier, etc. targeted by the second ligand is used in combination with the target specificity enhancing agent, is higher than the ratio wherein they are not used in combination, or when the therapeutic effect in the combined use case is superior than that in the case without combined use, then it is determined that the target specificity of the carrier, etc. is enhanced.

The dose ratio of the target specificity enhancing agent of the invention and the carrier, etc. targeted by the second ligand may be any ratio as long as target specificity of the carrier, etc. is enhanced; those skilled in the art can appropriately determine the suitable ratio by the following method, for example: to a subject such as an experimental animal, either a predetermined amount of the labeled carrier, etc. and a varying amount of the target specificity enhancing agent relative to the carrier, etc., or a predetermined amount of the target specificity enhancing agent and a varying amount of the labeled carrier, etc. relative to the target specificity enhancing agent, are administered, then the amount of the label in the target tissue or cells is measured. For example, when mannose is used as the first ligand and fucose is used as the second ligand, the ratio of mannose to fucose is, for example when represented by a mass ratio, 20000:1-200:1, 10000:1-300:1, 5000:1-500:1, 3000:1-1000:1, 2500:1-1500:1; when represented by a molar ratio, 16000:1-160:1, 8000:1-240:1, 4000:1-400:1, 2400:1-500:1, 2000:1-1200:1, etc. In addition, when mannose is used as the first ligand, the dosage of the target specificity enhancing agent may be, in terms of mannose per 1 administration, 0.01-

10000 mg/kg body weight, 0.1-1000 mg/kg body weight, 0.5-500 mg/kg body weight, 1-100 mg/kg body weight, 5-50 mg/kg body weight, or 0.05-50000 μmole/kg body weight, 0.5-5000 μmole/kg body weight, 2.5-2500 μmole/kg body weight, 5-500 μmole/kg body weight, 25-250 μmole/kg body weight, etc.

The target specificity enhancing agent of the present invention can be administered simultaneously or sequentially with the carrier, etc. targeted by the second ligand. Accordingly, the target specificity enhancing agent may be administered simultaneously with the carrier, etc., administered before the carrier, etc., or administered after the carrier, etc. In the case of sequential administration of the target specificity enhancing agent and the carrier, etc., the carrier, etc. may be administered sequentially and immediately after the target specificity enhancing agent, the target specificity enhancing agent may be administered sequentially and immediately after the carrier, etc., the carrier, etc. may be administered with a certain time interval after administration of the target specificity enhancing agent, the target specificity enhancing agent may be administered with a certain time interval after administration of the carrier, etc., or a combination thereof may be adopted. Therefore, for example, following the administration of the target specificity enhancing agent, the target specificity enhancing agent and the carrier, etc. may be simultaneously administered after a certain time interval, then the target specificity enhancing agent may be administered after a further time interval. The time interval may be within 48 hr, within 36 hr, within 24 hr, within 12 hr, within 6 hr, within 5 hr, within 4 hr, within 3 hr, within 2 hr, within 1 hr, within 30 min, within 15 min, or within 10 min, etc. Those skilled in the art can appropriately determine the time interval as follows, for example: a target specificity enhancing agent and a carrier, etc. are administered to a subject such as an experimental animal with various sequences and time intervals, then the amount of label in target tissue or cells is measured.

The pharmaceutical preparation, pharmaceutical composition, or target specificity enhancing agent of the present invention may be administered via various routes including both oral and parenteral routes, and examples include, but are not limited to, oral, intravenous, intramuscular, subcutaneous, topical, rectal, intraarterial, intraportal, intraventricular, transmucosal, transdermal, intranasal, intraperitoneal, intrapulmonary, and intrauterine routes, etc., and the composition may be formulated in a dosage form suitable for each of the administration routes. As such dosage form and formulation method, any known dosage forms and formulation methods may be appropriately adopted (for example, see Hyojun Yakuzaigaku (Standard Pharmaceutics), Ed. Yoshiteru Watanabe et al., Nankodo, 2003).

Dosage forms suitable for oral administration include, but are not limited to, powders, granules, tablets, capsules, solutions, suspensions, emulsions, gels, syrups, etc., and dosage forms suitable for parenteral administration include injections such as solution injections, suspension injections, emulsion injections and injections in a form that is prepared at the time of use. Formulations for parenteral administration may be in a form of aqueous or non-aqueous isotonic sterile solution or suspension.

The pharmaceutical preparation or pharmaceutical composition of the present invention may be supplied in any forms, and from the viewpoint of preservation stability, it may be provided in a form that can be prepared at the time of use, for example, in a form that it can be prepared at a site of clinical practice or its vicinity by a doctor, and/or pharmacist, nurse, or other paramedical staff. In this case, the pharmaceutical preparation or pharmaceutical composition of the present invention is provided in one or more containers containing at least one of the essential constituents, and it is prepared before use, for example within 24 hr, preferably within 3 hr, and more preferably just prior to use. Upon preparation, reagents, solvents and formulation tools usually available at a site of preparation can be appropriately used.

Another aspect of the present invention relates to a kit for preparing a pharmaceutical preparation of the invention, or for treating a disease related to a target cell, comprising one or more containers comprising, singly or in combination, a first ligand for a polyspecific lectin in a reticuloendothelial cell and a medicament for treating a disease related to a target cell, wherein the medicament is targeted by a second ligand for a polyspecific lectin in a reticuloendothelial cell which is different from the first ligand, and also relates to essential constituents of the pharmaceutical preparation of the invention provided in the form of such a kit. Furthermore, the present invention also relates to a kit comprising one or more containers comprising, singly or in combination, a first ligand for a polyspecific lectin in a reticuloendothelial cell and a carrier or a labeling agent targeted by a second ligand for a polyspecific lectin in a reticuloendothelial cell which is different from the first ligand, for preparing a pharmaceutical composition of the invention, for delivering a substance to a target cell, for labeling a target cell or a tissue containing a target cell, for detecting a target cell or a tissue containing a target cell, for imaging a target cell or a tissue containing a target cell, for diagnosing, detecting and/or monitoring a disease related to a target cell, for detecting the possibility of a disease related to a target cell, and/or for evaluating effects of treatment for a disease related to a target cell, and also relates to essential constituents of the pharmaceutical composition of the invention provided in the form of such a kit.

Each constituent of the kit of the present invention is as described above for the pharmaceutical preparation and pharmaceutical composition of the present invention. The kit of the invention may further contain, in addition to the above, instructions regarding preparation method and administration method of the pharmaceutical preparation and pharmaceutical composition of the invention, for example, an instruction leaflet, or a recording medium containing information on the method of use such as flexible disk, CD, DVD, blue ray disk, memory card, USB memory, etc. Furthermore, the kit of the present invention may contain all the constituents necessary for completing the pharmaceutical preparation or the pharmaceutical composition of the invention, but it does not necessarily contain all the constituents. Accordingly, the kit of the present invention does not have to contain reagents and solvents usually available at a clinical practice site or experimental facility, such as sterile water, physiological saline, and glucose solution, etc.

Further aspect of the present invention relates to a method for controlling an activity or growth of a target cell, or for treating a disease related to a target cell, comprising administering an effective amount of the pharmaceutical preparation and/or pharmaceutical composition of the invention to a subject in need thereof; and furthermore relates to a method for specifically delivering a substance to a target cell, for labeling a target cell or a tissue containing a target cell, for detecting a target cell or a tissue containing a target cell, for imaging a target cell or a tissue containing a target cell, for diagnosing, detecting and/or monitoring a disease related to a target cell, for detecting the possibility of a disease related to a target cell, and/or for evaluating effects of a treatment for a disease related to a target cell, comprising administering an effective amount of the pharmaceutical composition of the invention to a subject in need thereof. Here, the effective amount may be, for example, in the case of the method for controlling the activity or growth of a target cell, an amount that can increase or decrease the activity or growth of the target cell; in the case of a method for treating a disease related to a target cell, it is an amount to suppress the onset or recurrence of, to alleviate the symptoms of, or to delay or halt the progression of said disease, and it is preferably an amount to prevent the onset or recurrence of, and to cure said disease; in the case of a method for specifically delivering a substance to a target cell, it is an amount that can deliver the substance to the target cell more rapidly and/or in a larger amount compared to non-target cells; in the case of a method for labeling in vivo or in vitro a target cell or a target tissue, for detecting in vivo or in vitro a target cell or a tissue containing a target cell, for imaging in vivo or in vitro a target cell or a tissue containing a target cell, for diagnosing, detecting and/or monitoring a disease related to a target cell, for detecting the possibility of a disease related to a target cell, and/or for evaluating effects of treatment for a disease related to a target cell, the effective amount is an amount that can, for example, detectably label the target cell or target tissue.

In addition, an amount that does not cause an adverse effect exceeding the benefit from the administration is preferred. Such an amount can be appropriately determined by in vitro tests using culture cells, or by tests using a laboratory animal such as a mouse, rat, dog or pig or disease model animals, and such test methods are well known to those skilled in the art. Moreover, the doses of the first ligand and second ligand contained in the pharmaceutical preparation and of a drug and label used in the method of the present invention are known to a person skilled in the art, or may be determined as appropriate by the above-mentioned tests, etc. In the method for labeling a target cell or a target tissue, a substance to be delivered by the carrier is the label described above in relation to the pharmaceutical composition.

The possibility of a disease related to a target cell includes presence of an index that has high relevance with the disease related to the target cell, and examples of such index include the number of target cells which is larger than that in normal individuals, activity of target cells which is higher than that in normal individuals, and detection result of target cells which is different from that in normal individuals, etc.

The specific dose of a pharmaceutical preparation or pharmaceutical composition administered in the method of the present invention can be determined by taking into account various conditions regarding the subject in need of treatment, such as, type of target, aim of the method, contents of therapy, kind of disease, severity of symptoms, general health conditions of the subject, age, body weight, gender of the subject, diet, time and frequency of administration, concomitant medicines, response to therapy, and compliance to therapy.

Regarding the administration route, various routes including both oral and parenteral routes are included, for example, oral, intravenous, intramuscular, subcutaneous, topical, rectal, intraarterial, intraportal, intraventricular, transmucosal, transdermal, intranasal, intraperitoneal, intrapulmonary and intrauterine routes, etc.

Frequency of administration differs depending on the nature of the preparation or composition used and the above conditions of the subject; examples may include multiple times per day (namely, 2, 3, 4 times, or 5 times or more per day), once a day, once every several days (namely, every 2, 3, 4, 5, 6, 7 days, etc.), several times per week (e.g., 2, 3, or 4 times a week), every one week, and every several weeks (namely, every 2, 3, or 4 weeks). In these cases, it is preferable to administer both the first and second components of the pharmaceutical preparation or pharmaceutical composition of the invention in each administration; when the administration frequency is high, for example, administration is performed multiple times per day, then the administration frequency of the first component may be decreased compared to that of the second component. Here, when the first component is administered plural times per single administration of the second component, each administration means this series of administration.

The methods of detection, imaging, diagnosis, monitoring and/or evaluation of the present invention may furthermore contain detecting a label contained in said label-containing composition. A label may be contained in the composition at the time of detection, or may be present separately. Detection of the label may be carried out by any means that can detect the label, and examples include, but are not limited to, naked eye, optical examination apparatus (e.g., optical microscope, fluorescence microscope, phase contrast microscope, in vivo imaging apparatus, etc.), X-ray apparatus (e.g., plain X-ray apparatus, computed tomography (CT) apparatus, etc.), magnetic resonance imaging (MRI) apparatus, nuclear medicine apparatus (e.g., scintigraphic apparatus, PET apparatus, SPECT apparatus, etc.), ultrasonographic apparatus and thermographic apparatus, etc. Labels suitable for each detection means are known to a person skilled in the art (for example, refer to Lecchi et al., Q J Nucl Med Mol. Imaging. 2007; 51(2): 111-26, etc.), and non-limiting examples are already described above.

In one embodiment of the present invention, target cells is detected (for example, imaged) in vivo. In such detection, any apparatus suitable for in vivo detection can be used, and examples include, but are not limited to, optical examination apparatus (e.g., in vivo imaging apparatus, etc.), X-ray apparatus (e.g., plain X-ray apparatus, computed tomography (CT) apparatus, etc.), magnetic resonance imaging (MRI) apparatus, nuclear medicine apparatus (e.g., scintigraphic apparatus, PET apparatus, SPECT apparatus, etc.), ultrasonographic apparatus and thermographic apparatus, etc. Labels suitable for such detection are also known to a person skilled in the art (for example, refer to Lecchi et al., Q J Nucl Med Mol. Imaging. 2007; 51(2): 111-26, etc.).

By detecting (for example, imaging) a target cell in vivo, it is possible to determine the location (for example, organ or part of a body) of the target cell, and the lesion of a disease related to the target cell. Accordingly, the present invention also relates to a method for determining the location of a target cell and/or the lesion of a disease related to a target cell, the method comprising administering an effective amount of said label-containing composition to a subject in need thereof. Such method can contribute to the diagnosis of diseases related to the target cell.

Furthermore, by detecting a label in vitro or in vivo, it is possible to obtain information that contributes to the diagnosis of a disease related to a target cell, such as the number and distribution of target cells. Therefore, the present invention also relates to a method for aiding the diagnosis of a disease related to a target cell, the method comprising administering an effective amount of said label-containing composition to a subject in need thereof. This method may further comprise providing information that contributes to the diagnosis of diseases related to the target cell, to a medical doctor.

The method for detecting and the method for diagnosing a disease related to a target cell, the method for detecting the possibility of a disease related to a target cell, and the method for aiding the diagnosis of a disease related to a target cell of the present invention may furthermore comprise comparing the detection result of a label in a subject with the detection result of a reference label. The detection result of the reference label may be, for example, a detection result of a label in a subject who is determined not to have the disease related to the target cell (also referred to as "negative detection result"), or may be a detection result of a label in a subject who is determined to have the disease related to the target cells (also referred to as "positive detection result"). Here, for instance, when the detection result of a label in a subject is equal to the negative detection result (for example, there is no significant difference between them), then the subject can be determined to be negative, and when the detection result of a label in a subject significantly exceeds the negative detection result, then the subject can be determined to be positive. In addition, when the detection result of a label in a subject is equal to the positive detection result (for example, there is no significant difference between them), then the subject can be determined to be positive.

The detection result of a label in the methods of detection, imaging, diagnostic aid, monitoring and/or evaluation of the present invention may be a signal intensity and/or signal distribution of the detected label.

Here, the signal intensity of a label is meant herein to refer to an intensity or a measurement similar thereto of various signals emitted from the label, such as fluorescent signal, luminescent signal, magnetic signal and radioactive signal, and typically is measured by an appropriate detection means. Specific examples of detection means are already discussed above. The signal intensity may be those obtained from an entire subject or those obtained from a specific site or region of a subject. The signal intensity may also be an average value or an integrated value with regard to the area or the volume of a site to be measured. In cases where a signal intensity changes over time, the signal intensity of the present method may be of a specific time point, or may be integrated for a given time period. When the number and activity, etc. of target cells increase with progression of a disease, then an increase in the signal intensity can be an index of presence or progression of the disease, and conversely, a decrease in the signal intensity can be an index of improvement of the disease.

The signal distribution of a label is meant herein to refer to information on the position of a signal emitted from the label in a subject, and it may be two-dimensional or three-dimensional. By matching the signal distribution with an anatomical relative position of organs or with structural information of tissues such as CT image, MRI image or ultrasound image, it is possible to identify from which tissue the signal is emitted. In cases where the signal distribution changes over time, the signal distribution of the present method may be of a specific time point, or may be integrated for a given time period. When a region where target cells are present expands with progression of a disease, then an expansion in the signal distribution can be an index of presence or progression of the disease, and conversely, a shrinkage in the signal distribution can be an index of improvement of the disease.

In the method of the present invention, it is also possible to evaluate the combination of signal intensity and signal distribution. A simultaneous evaluation of both intensity and position of the signal allows a more accurate determination, as well as provision of more accurate information.

The monitoring method of the present invention may comprise a step of comparing a detection result at a first time point with a detection result at a second time point that is later than the first time point. For instance, when the detection result is an index regarding the number of target cells (e.g., a signal intensity or signal distribution, etc. of a label taken up by target cells), and when the index at the second time point is smaller than the index at the first time point, this indicates a decrease in the number of target cells; when a disease related to a target cell is the one that worsens with growth of target cells, then this result means that the disease related to the target cell has been improved. For instance, when the signal intensity at the second time point is lower than the signal intensity at the first time point, then it can be determined that the disease has improved, and conversely, when the signal intensity at the second time point is higher than the signal intensity at the first time point, then it can be determined that the disease has worsened. Furthermore, for instance, when the signal distribution at the second time point is narrower than the signal distribution at the first time point, then it can be determined that the disease has improved, and conversely, when the signal distribution at the second time point is broader than the signal distribution at the first time point, then it can be determined that the disease has worsened.

The evaluation method of effects of a treatment of the present invention may further comprise a step of comparing a detection result of a first time point prior to the treatment with a detection result of a second time point after the treatment, which is later than the first time point, or comparing a detection result of a first time point that is after a first treatment with a detection result of a second time point that is after a second treatment performed after the first treatment. For instance, when the detection result is an index regarding the number of target cells (e.g., a signal intensity or signal distribution, etc. of a label taken up by target cells), and when the index at the second time point is smaller than the index at the first time point, this indicates a decrease in the number of target cells; when a disease related to a target cell is the one that worsens with growth of target cells, then this result means that the disease related to the target cell has been improved, namely, the effects of the treatment is positive. For instance, when the signal intensity at the second time point is lower than the signal intensity at the first time point, then it can be determined that the disease has improved by the treatment, and therefore the treatment is successful. Conversely, when the signal intensity at the second time point is higher than the signal intensity at the first time point, then it can be determined that the disease has worsened by the treatment, so that the treatment is not so successful or is unsuccessful. Furthermore, for instance, when the signal distribution at the second time point is narrower than the signal distribution at the first time point, then it can be determined that the disease has improved by the treatment, and therefore the treatment is successful, and conversely, when the signal distribution at the second time point is broader than the signal distribution at the first time point, then it can be determined that the disease has worsened by the treatment, so that the treatment is not so successful or is unsuccessful.

Further aspect of the present invention relates to a method for enhancing the target specificity of a carrier, medicament or labeling agent targeted by the second ligand of the present invention (hereinafter, those may be abbreviated as targeted carrier, etc.), comprising administering an effective amount of the target specificity enhancing agent of the invention to a subject in need thereof. Here, the effective amount may be, for example, an amount to increase the target specificity of the above-mentioned carrier, medicament or labeling agent, or to increase therapeutic effect of the above medicament. In addition, an amount that does not cause an adverse effect exceeding the benefit from the administration is preferred. Such an amount can be appropriately determined by in vitro tests using culture cells, or by tests using a laboratory animal such as a mouse, rat, dog or pig, or disease model animals which aims to evaluate the target specificity as mentioned above. Moreover, the dose of the first ligand contained in the target specificity enhancing agent may be determined as appropriate by the above-mentioned tests, etc. When mannose is used as the first ligand and fucose is used as the second ligand, the ratio of mannose to fucose, and the dose of mannose are as described above for the target specificity enhancing agent of the present invention.

The specific dose of a target specificity enhancing agent to be administered in the method of the present invention can be determined by taking into account various conditions regarding the subject in need of treatment, such as, type of target, kind of disease, severity of symptoms, general health conditions of the subject, age, body weight, gender of the subject, diet, time and frequency of administration, concomitant medicines, response to therapy, and compliance to therapy.

Regarding the administration route, various routes including both oral and parenteral routes are included, for example, oral, intravenous, intramuscular, subcutaneous, topical, rectal, intraarterial, intraportal, intraventricular, transmucosal, transdermal, intranasal, intraperitoneal, intrapulmonary and intrauterine routes, etc.

Frequency of administration differs depending on the nature of the agent used and the above conditions of the subject; examples may include multiple times per day (namely, 2, 3, 4 times, or 5 times or more per day), once a day, once every several days (namely, every 2, 3, 4, 5, 6, 7 days, etc.), several times per week (e.g., 2, 3, or 4 times a week), every one week, and every several weeks (namely, every 2, 3, or 4 weeks). In these cases, it is preferable to administer both the target specificity enhancing agent and the carrier, etc., targeted by the second ligand in each administration; when the administration frequency is high, for example, administration is performed multiple times per day, then the administration frequency of the target specificity enhancing agent may be decreased compared to that of the carrier, etc. Moreover, for a single administration of the carrier, etc., the target specificity enhancing agent may be administered plural times (2, 3, 4, 5 or more times), and such administration may be simultaneously with, and/or before and/or after the administration of the carrier, etc. Accordingly, the target specificity enhancing agent can be administered plural times at such timing as once before the administration of the carrier, etc., once simultaneously with the administration of the carrier, etc., and further once after the administration of the carrier, etc.

In the method of the present invention, the term "subject" means any individual organism, and is preferably an animal, more preferably a mammal, and furthermore preferably a human individual. In the present invention, the subject may be healthy or may suffer from a certain disease; when the treatment, detection, diagnosis, diagnostic aid or monitoring of a disease related to a target cell, or the detection of the possibility of a disease related to a target cell is contemplated, the subject means those suffer from said disease, or have a risk of suffering from said disease; when the enhancement of target specificity of a targeted medicament, labeling agent or carrier is contemplated, the subject means those who are planned to be administered with, or those who have already administered with such medicament, labeling agent or carrier; when the evaluation of effects of a treatment for a disease related to a target cell is contemplated, the subject typically means those who are receiving the treatment of said disease, or those who are going to receive the treatment.

In addition, the term "treatment" is intended to encompass any kinds of medically acceptable preventive and/or therapeutic intervention with the aim of cure, transient remission or prevention of a disease. For example, the term "treatment" encompasses medically acceptable interventions with various objects, including delay or halt of progression of a disease related to a target cell, regression or elimination of lesions, prevention of onset of or prevention of recurrence of said disease.

One aspect of the present invention relates to a substance delivery carrier for fucosylated molecule-producing cells, which comprises fucose. One embodiment of the present invention relates to a carrier that is targeted at fucosylated molecule-producing cells by fucose. The carrier may comprise an effective amount of fucose for the targeting of fucosylated molecule-producing cells. Accordingly, one embodiment of the present invention relates to a carrier comprising an effective amount of fucose for the targeting of fucosylated molecule-producing cells, which is targeted at said cells. In addition, the carrier may be used to deliver a substance to fucosylated molecule-producing cells. Accordingly, one embodiment of the present invention relates to a carrier for delivering a substance to fucosylated molecule-producing cells, which comprises fucose. Fucosylated molecule-producing cells are as described above for the combined pharmaceutical preparation of the invention.

Another aspect of the present invention relates to a substance delivery carrier for cells having a fucose binding mechanism, which comprises fucose. This carrier targets the fucose binding mechanism. Therefore, one embodiment of the present invention relates to a carrier that is targeted by fucose at cells having a fucose binding mechanism. Details of the fucose binding mechanism are as mentioned above. This carrier may comprise an effective amount of fucose for the targeting of cells having a fucose binding mechanism. Accordingly, one embodiment of the present invention relates to a carrier that is targeted at cells having a fucose binding mechanism, which comprises an effective amount of fucose for the targeting of said cells. Furthermore, this carrier can be used for delivering a substance to cells having a fucose binding mechanism. Accordingly, one embodiment of the present invention relates to a carrier for delivering a substance to cells having a fucose binding mechanism, which comprises fucose. Furthermore, since the fucose binding mechanism is associated with the amount of production of fucosylated molecule and the amount of expression of fucosyltransferase, these can be used as an index of having a fucose binding mechanism. Therefore, in one embodiment of the present invention, the cell having a fucose binding mechanism produces a fucosylated molecule. In addition, in another embodiment of the present invention, the cell having a fucose binding mechanism expresses a fucosyltransferase. Details regarding the production of fucosylated molecule and expression of fucosyltransferase are as described above for the combined pharmaceutical preparation of the invention.

A further aspect of the present invention relates to a substance delivery carrier for cells expressing a fucosyltransferase, which comprises fucose. Said carrier may comprise an effective amount of fucose for the targeting of fucosyltransferase-expressing cells. Accordingly, one embodiment of the present invention relates to a carrier that is targeted at fucosyltransferase-expressing cells, which comprises an effective amount of fucose for the targeting of said cells. Moreover, said carrier can be used for delivering a substance to fucosyltransferase-expressing cells. Accordingly, one embodiment of the present invention relates to a carrier for delivering a substance to fucosyltransferase-expressing cells, which comprises fucose. Details regarding the expression of fucosyltransferase are as described above. Since the expression of fucosyltransferase is associated with the production of fucosylated molecule and presence of fucose binding mechanism, these can be used as an index of expression of fucosyltransferase. Accordingly, in one embodiment of the present invention, the fucosyltransferase-expressing cell produces a fucosylated molecule. Also, in another embodiment of the present invention, the fucosyltransferase-expressing cell has a fucose binding mechanism. Details regarding the production of fucosylated molecule and presence of fucose binding mechanism are as described above for the combined pharmaceutical preparation of the invention.

As used herein, "targeting" means that, compared to non-targeted substances, a substance such as a drug or carrier is delivered to a specific target, for example, a specific cell and tissue (in the present invention, a fucosylated molecule-producing cell and/or a cell having a fucose binding mechanism and/or a fucosyltransferase-expressing cell (hereinafter, only the fucosylated molecule-producing cell is mentioned as their representative), as well as a tissue containing said cell), more rapidly, efficiently and/or in a larger amount than to non-target cells and tissues, namely, such a substance is specifically delivered to the target; a targeting agent means a substance that, when it is bound to or reacted with another substance, it can make this another substance to be targeted in such a manner. Therefore, the fucose in the present invention functions as a targeting agent. In addition, target specificity means a degree of rapidness, efficiency, and/or an amount at which a targeted substance such as a medicament or carrier is delivered to a target cell compared to non-target cells; when target specificity is high, then the targeted substance is delivered to the target cell more efficiently, while its delivery to non-target cells is suppressed.

The fucose contained in the carrier of the present invention is not particularly limited as long as it facilitates the delivery of a substance to fucosylated molecule-producing cells, and examples include L-fucose, D-fucose, a sugar chain comprising L-fucose and/or D-fucose, for example, a sugar chain comprising L-fucose and/or D-fucose at its side chain, or a sugar chain comprising L-fucose and/or D-fucose at its non-reducing terminal, and a polypeptide or lipid to which L-fucose and/or D-fucose is bound.

The carrier of the invention may be composed of these kinds of fucose themselves, or may be composed by binding or including fucose to a carrier constituent other than fucose. Accordingly, the carrier of the invention may comprise a carrier constituent other than fucose. In this case, the relationship between fucose and a carrier constituent other than fucose is not particularly limited as long as the fucose forms a complex with a structure formed by the carrier constituent other than fucose, in a manner that the fucose can function as a targeting agent, and it includes those wherein the fucose binds to the structure formed by the carrier constituent other than fucose directly, or via an intervening chemical element such as a linker or a spacer, in a manner that the fucose can be in contact with a target cell element. As examples of the carrier constituent other than fucose, without limitation, any components known in the fields of medicine and pharmacology may be used; however, those that can include fucose or that can bind to fucose are preferable.

Examples of such constituent include lipids, for example, phospholipid such as glycerophospholipid, sphingolipid such as sphingomyelin, sterol such as cholesterol, vegetable oil such as soybean oil and poppy seed oil, mineral oil, lecithins such as egg yolk lecithin, polyethylene glycol, PEG:polymer carrier, etc., but they are not limited thereto. Of these, those which can constitute a liposome, for example, natural phospholipid such as lecithin, semi-synthetic phospholipid such as dimyristoyl phosphatidylcholine (DMPC), dipalmitoylphosphatidylcholine (DPPC) and distearoylphosphatidylcholine (DSPC), as well as dioleyl phosphatidylethanolamine (DOPE), dilauroyl phosphatidylcholine (DLPC), and cholesterol are preferable.

Particularly preferable constituents include those which can avoid being trapped by the reticuloendothelial system, for example, cationic lipids such as N-(α-trimethylammonioacetyl)-didodecyl-D-glutamate chloride (TMAG), N,N',N'',N'''-tetramethyl-N,N',N'',N'''-tetrapalmityl spermine (TMTPS), 2,3-dioleyloxy-N-[2(sperminecarboxamide)ethyl]-N,N-dimethyl-1-propanaminium trifluoroacetate (DOSPA), N-[1-(2,3-dioleyloxy)propyl]-N,N,N-trimethylammonium chloride (DOTMA), dioctadecyl dimethyl ammonium chloride (DODAC), didodecyl ammonium bromide (DDAB), 1,2-dioleyloxy-3-trimethylammoniopropane (DOTAP), 3β-[N—(N',N'-dimethylaminoethane)carbamoyl]cholesterol (DC-Chol), 1,2-dimyristoyloxypropyl-3-dimethylhydroxyethyl ammonium bromide (DMRIE), O,O'-ditetradecanoyl-N-(α-trimethylammonioacetyl) diethanolamine chloride (DC-6-14), etc.

Binding or inclusion of fucose in the carrier of the invention is also possible by binding or inclusion of fucose to other constituents of the carrier by means of chemical and/or physical method. Examples of the method to bind fucose to a carrier include, but are not limited to: a method wherein a liposome is treated to have a hydrophilic property using tris(hydroxyalkyl)aminoalkane, to which a linker protein, for example a protein derived from living organisms such as human serum albumin (HSA) and bovine serum albumin (BSA), is bound, and a sugar chain is bound to the linker protein (WO2007/091661, Hirai et al., Biochem Biophys Res Commun. 2007; 353(3): 553-8, Hirai et al., Int J. Pharm. 2010; 391(1-2): 274-83), a method to prepare liposomes using a sugar-added cholesterol derivative (Patent Literature 1), a method wherein a sugar is added to poly-L-lysine (Negre et al., Supra), a method wherein a liposome is prepared using a glycolipid, or a method wherein p-aminophenyl-D-glycoside is covalently bound to phosphatidylethanolamine liposome using glutaraldehyde (Ghosh P et al., Biochim Biophys Acta. 1980; 632(4): 562-72), a method wherein a liposome is prepared using cholesten-5-yloxy-N-(4-((1-imino-2-β-D-thioglycosylethyl)amino)butyl)formamide (Non-patent Literature 1), and the like. Alternatively, binding or inclusion of fucose to the carrier of the invention is possible by mixing fucose with other constituents of the carrier at the time of preparing the carrier.

The amount of fucose to be bound to or included in the carrier of the invention may be, without limitation, expressed by the weight ratio in the constituents of the carrier, 0.01%-100%, preferably 0.2%-20%, and more preferably 1-5%. Binding or inclusion of fucose to/in the carrier of the invention may be carried out before a drug, etc. is supported by the carrier, or by simultaneously mixing the carrier, fucose, and a drug, etc., or by mixing the carrier which has already supported a drug, etc. with fucose. Accordingly, the present invention also relates to a process for preparing a formulation specific to fucosylated molecule-producing cells, which includes a step of binding fucose to any existing drug-bound carrier or drug-encapsulated carrier, for example liposomal formulations such as DaunoXome®, Doxil, Caelyx®, Myocet®, etc.

The form of the carrier of the invention may be any form, as long as it can deliver a desired substance or matter to target cells, and examples include, but are not limited to, polymer micelle, liposome, emulsion, microsphere, nanosphere, polymer matrix, and lipoplex. In the present invention, from the viewpoints of level of delivery efficiency, range of substances being delivered, easiness of formulation and the like, a liposomal form or lipoplex form is preferable, and a cationic liposome comprising a cationic lipid is particularly preferable. When the carrier is in a liposomal form, the molar ratio of the fucose to the liposome-constitutive lipid is preferably from 8:1 to 1:8, more preferably from 4:1 to 1:4, yet more preferably from 2:1 to 1:2, and in particular, it is 1:1. In another embodiment, the concentration of the fucose in a carrier suspension is 5-500 μg/ml, preferably 10-250 μg/ml, more preferably 20-200 μg/ml, and furthermore preferably 25-100 μg/ml.

In the carrier of the present invention, as long as the fucose contained therein is present in a manner that it can function as a targeting molecule, the carrier may comprise a substance being transported in its interior, or the carrier may be attached to the external of a substance being transported, or the carrier may be mixed with a substance being transported. Here, "function as a targeting molecule" means that the carrier comprising fucose reaches and/or is taken up by the target cell more rapidly and/or in a larger amount compared to the carrier without fucose; this can be easily confirmed, e.g., by adding to a cell culture a carrier to which a label is attached or that comprises a label, and by analyzing the site of the label after a certain period of time. Structurally, when the fucose is at least partially exposed outside of the formulation comprising the carrier, or the fucose is present in a form that it can be recognized by a target cell element, at the latest before reaching a target cell, then, the above requirements can be satisfied.

The substance or matter that is delivered by the carrier of the invention is not particularly limited, and it desirably has a size with which it can physically move inside the body from the administration site to the site of lesion where a target cell is present. Accordingly, the carrier of the invention can transport not only substances such as atoms, molecules, compounds, proteins, and nucleic acids, etc., but also matters such as vectors, virus particles, cells, drug-release systems composed of one or more elements, micromachines, etc. The above substances or matters preferably have a characteristic to influence target cells and/or their periphery, and they include, for example, those which can label target cells, or can control (for example, enhance or suppress) the activity or growth of target cells and/or cells present in their periphery.

Therefore, in one embodiment of the present invention, the substance delivered by the carrier is "a drug that controls the activity or growth of fucosylated molecule-producing cells" which is described above in relation to the combined pharmaceutical preparation of the invention. The substance to be delivered by the carrier of the invention is a drug to treat a disease related to fucosylated molecule-producing cells. These drugs are as described above for the combined pharmaceutical preparation of the invention.

In the present invention, "for fucosylated molecule-producing cell" means that it is suitable to use a fucosylated molecule-producing cell as a target; this includes, e.g., that a substance can be delivered to a fucosylated molecule-producing cell more rapidly, with higher efficiency and/or in a larger amount than to a fucosylated molecule-non-producing cell. For instance, the carrier of the invention can deliver a substance to a fucosylated molecule-producing cell, at a rate and/or efficiency of 1.1 times or more, 1.2 times or more, 1.3 times or more, 1.5 times or more, 2 times or more, and furthermore, 3 times or more than to a fucosylated molecule-non-producing cell.

The present invention also relates to a composition comprising said carrier and said drug that controls the activity or growth of fucosylated molecule-producing cells (hereinafter, this may be referred to as drug-containing composition), and to the use of said carrier in the preparation of such compositions. In one embodiment of the present invention, said composition may be those used for controlling the activity or growth of fucosylated molecule-producing cells, or for treating diseases related to fucosylated molecule-producing cells. Moreover, said composition may comprise a drug that controls the activity or growth of fucosylated molecule-producing cells in an effective amount for controlling the activity or growth of fucosylated molecule-producing cells, or for treating diseases related to fucosylated molecule-producing cells. Here, the effective amount is, in the latter case, an amount to suppress the onset or recurrence of, to alleviate the symptoms of, or to delay or halt the progression of said diseases, and it is preferably an amount to prevent the onset or recurrence of, and to cure said diseases. In addition, an amount that does not cause an adverse effect exceeding the benefit from the administration is preferred. Such an amount can be appropriately determined by in vitro tests using culture cells, and by examination using a model animal such as a mouse, rat, dog or pig, and such examination methods are well known to those skilled in the art. Moreover, the doses of fucose contained in the carrier and of a drug used in the method of the present invention are known to a person skilled in the art, or may be determined as appropriate by the above-mentioned tests, etc.

A drug that controls the activity or growth of fucosylated molecule-producing cells in the composition of the present invention and a disease related to fucosylated molecule-producing cells are as described above in relation to the combined pharmaceutical preparation of the present invention. Accordingly, said composition may comprise a labeled drug. Furthermore, said composition may comprise, in addition to the drug that controls the activity or growth of fucosylated molecule-producing cells, a label, and other drugs, for example, the above-mentioned drugs, etc. that treat diseases related to fucosylated molecule-producing cells.

The present invention also relates to a composition comprising said carrier and a label (hereinafter, this may be referred to as a label-containing composition), and to the use of said carrier in the preparation of such compositions. In one embodiment of the present invention, said composition may be those for labeling fucosylated molecule-producing cells or tissue containing said cells, for detecting fucosylated molecule-producing cells or tissue containing said cells, for diagnosing, detecting and/or monitoring a disease related to fucosylated molecule-producing cells, for detecting the possibility of a disease related to fucosylated molecule-producing cells, for aiding the diagnosis of a disease related to fucosylated molecule-producing cells, or for evaluating the effects of a treatment of a disease related to fucosylated molecule-producing cells. Fucosylated molecule-producing cells or tissue containing said cells may be detected by in vivo or in vitro imaging. Accordingly, the above-mentioned composition may be used for in vivo or in vitro imaging of fucosylated molecule-producing cells or tissue containing said cells. Furthermore, said composition may comprise a label in an effective amount for labeling fucosylated molecule-producing cells or tissue containing said cells, for detecting fucosylated molecule-producing cells or tissue containing said cells, for in vivo or in vitro imaging fucosylated molecule-producing cells or tissue containing said cells, for diagnosing, detecting and/or monitoring a disease related to fucosylated molecule-producing cells, for detecting the possibility of a disease related to fucosylated molecule-producing cells, for aiding the diagnosis of a disease related to fucosylated molecule-producing cells, or for evaluating the effects of a treatment of a disease related to fucosylated molecule-producing cells.

Here, the effective amount of a label for labeling fucosylated molecule-producing cells or tissue containing said cells, for detecting fucosylated molecule-producing cells or tissue containing said cells, for in vivo or in vitro imaging fucosylated molecule-producing cells or tissue containing said cells, for diagnosing, detecting and/or monitoring a disease related to fucosylated molecule-producing cells, for detecting the possibility of a disease related to fucosylated molecule-producing cells, for aiding the diagnosis of a disease related to fucosylated molecule-producing cells, or for evaluating the effects of a treatment of a disease related to fucosylated molecule-producing cells may be an amount that is taken into fucosylated molecule-producing cells to a degree that the label can be detected in vivo or in vitro. In addition, an amount that does not cause an adverse effect exceeding the benefit from the administration is preferred. Such an amount can be appropriately determined by in vitro tests using culture cells, and by examination using a model animal such as a mouse, rat, dog or pig, and such examination methods are well known to those skilled in the art.

A label in the label-containing composition and a disease related to fucosylated molecule-producing cells, and a tissue containing fucosylated molecule-producing cells are as described above in relation to the combined pharmaceutical preparation and combined pharmaceutical preparation of the present invention. Said composition may comprise, in addition to a label, any drug such as the above-described drug that controls the activity or growth of fucosylated molecule-producing cells, and a drug that treats a disease related to fucosylated molecule-producing cells, etc.

In the composition of the present invention, as long as fucose contained in the carrier is present such that it functions as a targeting molecule, the carrier may comprise a substance being delivered in its interior, or the carrier may attach to the exterior of a substance being delivered, or the carrier may be mixed with a substance being delivered. Accordingly, depending on the route of administration and the manner of drug release, the above composition may be covered with an appropriate material, such as enteric coating or a material with timed disintegration, or the composition may be incorporated in an appropriate drug release system.

The composition of the present invention may be administered via various routes including both oral and parenteral routes, and examples include, but are not limited to, oral, intravenous, intramuscular, subcutaneous, topical, rectal, intraarterial, intraportal, intraventricular, transmucosal, transdermal, intranasal, intraperitoneal, intrapulmonary, and intrauterine routes, etc., and the composition may be formulated in a dosage form suitable for each of the administration routes. As such dosage form and formulation method, any known dosage forms and formulation methods may be appropriately adopted (for example, see Hyojun Yakuzaigaku (Standard Pharmaceutics), Ed. Yoshiteru Watanabe et al., Nankodo, 2003).

Dosage forms suitable for oral administration include, but are not limited to, powders, granules, tablets, capsules, solutions, suspensions, emulsions, gels, syrups, etc., and dosage forms suitable for parenteral administration include injections such as solution injections, suspension injections, emulsion injections and injections in a form that is prepared at the time of use. Formulations for parenteral administration may be in a form of aqueous or non-aqueous isotonic sterile solution or suspension.

Therefore, the composition of the present invention may be a pharmaceutical composition comprising one or more pharmaceutically acceptable surfactants, carriers, diluents and/or excipients. Pharmaceutically acceptable carriers and diluents, etc. are well known in the field of pharmaceuticals, and are described, for example, Remington's Pharmaceutical Sciences, 18th Ed., Mack Publishing Co., Easton, Pa. (1990), which is incorporated herein by reference in its entirety.

The carrier or the composition of the present invention may be supplied in any forms, and from the viewpoint of preservation stability, preferably it is provided in a form that can be prepared at the time of use, for example, in a form that it can be prepared at a site of clinical practice or its vicinity by a doctor, and/or pharmacist, nurse, or other paramedical staff. In this case, the carrier or the composition of the present invention is provided in one or more containers containing at least one of the essential constituents, and it is prepared before use, for example within 24 hr, preferably within 3 hr, and more preferably just prior to use. Upon preparation, reagents, solvents and formulation tools usually available at a site of preparation can be appropriately used.

Accordingly, the present invention also relates to a kit for preparing the carrier or composition, the kit containing one or more containers that contain fucose, and/or a substance being delivered, and/or a carrier constituent other than fucose, singly or in a combination thereof, and also relates to an essential constituent of the carrier or composition provided in such a kit. The kit of the present invention may further contain, in addition to the above, instructions regarding preparation method and administration method of the carrier and composition of the invention, for example, an instruction leaflet, or a recording medium containing information on the method of use such as flexible disk, CD, DVD, blue ray disk, memory card, USB memory, etc. Furthermore, the kit of the present invention may contain all the constituents necessary for completing the carrier or composition of the invention, but it does not necessarily contain all the constituents. Accordingly, the kit of the present invention does not have to contain reagents and solvents usually available at a clinical practice site or experimental facility, such as sterile water, physiological saline, and glucose solution, etc.

The present invention further relates to a method for controlling the activity or growth of fucosylated molecule-producing cells, or for treating a disease related to fucosylated molecule-producing cells, the method comprising administering an effective amount of said drug-containing composition to a subject in need thereof. A fucosylated molecule-producing cell, activity of fucosylated molecule-producing cells, a disease related to fucosylated molecule-producing cells, and an effective amount, dose, administration route, administration frequency, subject and treatment are the same as those described above for the combined pharmaceutical preparation of the present invention, etc.

The present invention further relates to a method that comprises administering an effective amount of said label-containing composition to a subject in need thereof, in order to label in vivo or in vitro fucosylated molecule-producing cells or tissue containing said cells, to detect in vivo or in vitro fucosylated molecule-producing cells or tissue containing said cells, to image in vivo or in vitro fucosylated molecule-producing cells or tissue containing said cells, to diagnose, detect and/or monitor a disease related to fucosylated molecule-producing cells, to detect the possibility of a disease related to fucosylated molecule-producing cells, to aid the diagnosis of a disease related to fucosylated molecule-producing cells, or to evaluate the effects of a treatment of a disease related to fucosylated molecule-producing cells. Said effective amount may be an amount that is effective for labeling fucosylated molecule-producing cells or tissue containing said cells, for detecting fucosylated molecule-producing cells or tissue containing said cells, for imaging fucosylated molecule-producing cells or tissue containing said cells, for diagnosing, detecting and/or monitoring a disease related to fucosylated molecule-producing cells, for detecting the possibility of a disease related to fucosylated molecule-producing cells, for aiding the diagnosis of a disease related to fucosylated molecule-producing cells, or for evaluating the effects of a treatment of a disease related to fucosylated molecule-producing cells, or an amount effective for detection. A fucosylated molecule-producing cell, a disease related to fucosylated molecule-producing cells, and an effective amount, etc. are the same as those described above for the combined pharmaceutical preparation and combined pharmaceutical composition of the present invention, etc.

The present invention furthermore relates to a method for delivering a substance to fucosylated molecule-producing cells using the above carrier that is targeted at fucosylated molecule-producing cells. This method includes, but is not limited to, for example a step of making said carrier to support a substance being delivered, and a step of administering or adding the carrier that supports the substance being delivered to an organism or a medium, such as a culture medium, comprising fucosylated molecule-producing cells. These steps can be appropriately realized in accordance with any known method, or any method described herein. The above delivery method may be combined with other delivery method, such as other delivery method targeting at an organ in which fucosylated molecule-producing cells are present. Furthermore, the above method includes an embodiment wherein the method is carried out in vitro, and an embodiment wherein the method is carried out in vivo, e.g., an embodiment wherein fucosylated molecule-producing cells in the body are targeted.

EXAMPLES

The present invention is described more in detail with reference to the following Examples; however, these examples are intended for exemplification, and they do not limit the scope of the present invention.

Cell culture method used in the Examples of the present invention is shown below. Pancreatic cancer cell lines KP4, PK-59, PK-45H, MIAPaCa2 and PANC-1, biliary tract cancer cell lines HuCCT1, RBE, TGBC24TKB, TGBC14TKB, SSP-25, YSCCC, TKKK and HuH-28, stomach cancer cell lines MKN45, MKN74, NUGC-4 and KATO-III were obtained from RIKEN BioResource Center, pancreatic cancer cell lines AsPC-1 and BxPC-3, colorectal cancer cell lines SW1116, COLO205, HT-29 and HCT-15, stomach cancer cell line NCI-N87, leukemia cell lines HL-60, RPMI8226, KG-1 and MOLT-4 were obtained from American Type Culture Collection (ATCC), colorectal cancer cell line LS174T was obtained from Tohoku University, colorectal cancer cell line LS180 was obtained from DS Pharma, stomach cancer cell line OCUG-1 was obtained from JCRB, stomach cancer cell lines JR-St and HSC-39 were obtained from IBL.

Cells were cultured as follows: BxPC-3, AsPC-1, PANC-1, PK-45H, and PK-59 cells were cultured in RPMI-1640 medium (GIBCO) comprising L-glutamine and 1% penicillin-streptomycin (Invitrogen); KP4 and MIAPaCa2 cells were cultured in 10% FBS-supplemented DMEM (GIBCO) comprising L-glutamine and 1% penicillin-streptomycin (Invitrogen); COLO205, HCT-15, HuCCT1, RBE, SSP-25, YSCCC, NCI-N87, MKN45, MKN74, NUGC-4, KATO-III, HL-60, RPMI8226, KG-1 and MOLT-4 cells were cultured in 10% FBS-supplemented RPMI1640 medium (GIBCO); SW1116 cells were cultured in 10% FBS-supplemented Leibovitz's L-15 medium; LS174T, LS180 and HuH-28 cells were cultured in 10% FBS-supplemented MEM; HT-29 cells were cultured in 10% FBS-supplemented McCoy's 5A medium; OCUG-1, TGBC24TKB, TGBC14TKB and TKKK cells were cultured in 10% FBS-supplemented DMEM (GIBCO); JR-St and HSC-39 cells were cultured in 10% FBS-supplemented TIL medium. Culture conditions of each cell are known to those skilled in the art, and are available from suppliers of the cells.

Example 1. Investigation of Tumor Marker Concentration in Supernatant of Various Pancreatic Cancer Cell Cultures $5 \times 10^6$ cells of each pancreatic cancer cell line were seeded in a 25-cm$^2$ flask, and cultured with 3 ml of serum-free medium Opti-MEM® for 48 hr. The concentrations of the fucosylated carbohydrate antigen tumor markers CA19-9, Span-1 and Dupan-2 in the supernatant of the cultures were investigated by ELISA method. Results are shown in FIG. 1(a). Based on the results, PK59 and AsPC-1 were designated to be fucosylated sugar chain high-producing cell lines, and MIAPaCa2 and PANC-1 to be fucosylated sugar chain low-producing cell lines.

Example 2. Expression of Fucosyltransferase (FUT) in Various Pancreatic Cancer Cell Lines With respect to each cell line PK59, AsPC-1, MIAPaCa2 and PANC-1, total RNA was extracted from $1 \times 10^6$ cells and subjected to RT-PCR. Using random hexamer (100 pM) and MMLV (GIBCO), total RNA (1 μg) was reverse-transcribed in accordance with manufacturer's instructions. Table 1 shows sequences of PCR primers used.

TABLE 1

Table 1.

| Gene | | Nucleic Acid Sequence (5'->3') | SEQ ID NO |
|---|---|---|---|
| FUT1 | U: | ATGTGGCTCCGGAGCCATCGTCAG | 1 |
| | L: | AGGATCTCTCAAGTCCGCGTACTC | 2 |

TABLE 1-continued

Table 1.

| Gene | | Nucleic Acid Sequence (5'->3') | SEQ ID NO |
|---|---|---|---|
| FUT2 | U: | CTAGCGAAGATTCAAGCCATGTGG | 3 |
| | L: | GACGTACTCCCCCGGGATGTG | 4 |
| FUT3 | U: | ATGGATCCCCTGGGTGCAGCCAAG | 5 |
| | L: | TCAGGTGAACCAAGCCGCTATGCT | 6 |
| FUT4 | U: | GTGCCCGAAATTGGGCTCCTGCAC | 7 |
| | L: | GAAGGAGGTGATGTGGACAGCGTA | 8 |
| FUT5 | U: | CTTATGGCAGTGGAACCTGTCACC | 9 |
| | L: | CCAGCCGTAGGGCGTGAAGATGTC | 10 |
| FUT6 | U: | CCCACTGTGTACCCTAATGGGTCC | 11 |
| | L: | CTCTCAGGTGAACCAAGCCGCTAT | 12 |
| FUT7 | U: | TCGGACATCTTTGTGCCCTATG | 13 |
| | L: | CGCCAGAATTTCTCCGTAATGTA | 14 |
| FUT8 | U: | TGCCTGGGGGACCTTGCTGT | 15 |
| | L: | CCCGCCAATCACCTGCTCCA | 16 |
| β actin | U: | ATCTGGCACCACACCTTCTACAATGAGCTGCG | 17 |
| | L: | CGTCATACTCCTGCTTGCTGATCCACATCTGC | 18 | cDNA was amplified with 25-30 cycles using Pfu Turbo (Stratagene), 0.2 mM of each dNTP, and 100 mM of each primer. The cycle consists of 30 sec at 95° C., 30 sec at 55° C., and 60 sec at 72° C. In addition, primers for each FUT were prepared based on the reference: Mas. et al., Glycobiology. 1998; 8(6): 605-13.

PCR products were subjected to 1.2% agarose-gel electrophoresis, and expression was observed under UV. Results are shown in FIG. 1(b). Expression of all the FUT genes except FUT7 was observed in various cell lines. Based on this result, PK59 and AsPC-1 were designated to be fucosyltransferase high-expression cell lines, and MIAPaCa2 and PANC-1 to be fucosyltransferase low-expression cell lines.

Example 3. Presence of Fucose Binding Mechanism in Various Pancreatic Cancer Cells Binding of fucose (fucose refers to L-fucose, unless otherwise stated) to the fucosylated sugar chain high-producing cell line AsPC-1 and fucosylated sugar chain low-producing cell line PANC-1 was investigated using radio-labeled fucose.

In a 12-well culture plate, $1 \times 10^5$ cells were seeded and cultured overnight, and $^{14}$C-fucose (specific activity: 55 mCi/mmol) diluted with BSA-PBS at a concentration of 0-200 nM was added to the cells and cultured at 4° C. for 1 hr. The cells were washed with cold BSA-PBS, lysed by 1% Triton X100/PBS-0.25% trypsin, and the radioactivity of the $^{14}$C-fucose bound to the cell membrane was measured (FIGS. 2 and 3).

In another experiment, in a 12-well culture plate, $2 \times 10^5$ cells were seeded and cultured overnight, 10 nmol of $^{14}$C-fucose (specific activity: 55 mCi/mmol) were added to the cells either singly or together with 1 pmol of fucose, and cultured at 4° C. for 1, 3, or 24 hr. The cells under each condition were washed with cold BSA-PBS, lysed by 1% Triton X100/PBS-0.25% trypsin, and the radioactivity of the $^{14}$C-fucose was measured (FIG. 4).

From these results, it has been clarified that fucose binds to AsPC-1 and PANC-1 via a receptor-like mechanism, and its affinity is higher in the fucosylated sugar chain high-producing cell line AsPC-1. In addition, because binding of $^{14}$C-fucose was inhibited by non-labeled fucose, this mechanism was clarified to be fucose-specific. This indicates the presence of a fucose-specific receptor-like binding mechanism in fucosylated sugar chain-producing cells, in particular, fucosylated sugar chain high-producing cells.

Example 4. Introduction of siRNA by Fucosylated Liposomes

Liposome (Lipotrust, 10 nmol) and L-fucose (0-20 nmol) (SIGMA, MO, USA) were suspended and left at a room temperature for 5 min, then free fucose was removed by a micropartition system (Sartorion VIVASPIN 5000MWCO PES). Next, FAM-labeled siRNA (random) (sense strand: 5'-CGAUUCGCUAGACCGGCUUCAUUGCAG-3' (SEQ ID NO: 19), antisense strand: 5'-GCAAUGAAGCCGGU-CUAGCGAAUCGAU-3' (SEQ ID NO: 20)) was added and incubated, which was then added to AsPC-1 cells seeded on a chamber slide, and cultured for 1 hr. After culturing, the cells were washed with PBS and fixed with 4% paraformaldehyde, washed with PBS, and counterstained with DAPI and observed under a fluorescence microscope. The result revealed that the molar ratio of liposome:fucose of 1:1 provides the highest introduction efficiency (FIGS. 5 and 6).

Example 5. Effect of Fucose on Introduction by Fucosylated Liposomes

In order to confirm that the introduction of siRNA is due to the fucose-specific receptor-like binding mechanism present in fucosylated molecule-producing cells, introduction efficiency of siRNA under the presence of an excessive amount of fucose was investigated. Liposome (Lipotrust, 10 nmol) and fucose (10 nmol) were suspended, left at a room temperature for 5 min, then free fucose was removed by a micropartition system (Sartorion VIVASPIN 5000MWCO PES). Then, the above FAM-labeled siRNA (random) was added and incubated, which was then added to AsPC-1 cells seeded on a chamber slide, and cultured for 1 hr (Liposome+ F). In addition, a group with liposome alone (Liposome), and a group wherein 1 μmol (×100) of fucose was added and pre-incubation was carried out for 10 min before addition of liposomes (Liposome+F+CE), were simultaneously investigated. After culturing, the cells were washed with PBS, fixed with 4% paraformaldehyde, washed with PBS, and counterstained with DAPI and observed under a fluorescence microscope. As a result, introduction of siRNA was significantly suppressed by the presence of fucose (FIG. 7). Namely, introduction of siRNA was inhibited by an excessive amount of fucose, indicating that introduction of siRNA by fucosylated liposomes is via a fucose-specific receptor-like binding mechanism.

Example 6. Comparison of siRNA Introduction Efficiency in Various Pancreatic Cancer Cell Lines Introduction efficiencies of siRNA by fucosylated liposomes in fucosylated sugar chain high-producing cells and low-producing cells were investigated. In accordance with the above-mentioned procedure, fucosylated liposomes were prepared, and introduction of FAM-siRNA in high-producing cell lines (PK59, AsPC-1) and in low-producing cell lines (MIAPaCa2, PANC-1) was observed under a fluorescence microscope. As a result, while a large amount of green FAM was observed inside the cells in the high-producing cell lines, the amount of green FAM inside the cells in the low-producing cell lines was significantly small (FIGS. 8 and 9). This indicates that fucosylated liposomes deliver a substance to cells in a manner depending on the amount of production of fucosylated sugar chains.

Example 7. Fucosyltransferase-Dependent Production of CA19-9 in Pancreatic Cancer Cell Line In order to verify that FUT is a causative gene of CA19-9 production in pancreatic cancer cell lines, cells were transfected with siRNA and expression of various FUT genes was inhibited. siRNA oligonucleotides were prepared in a purified and annealed double-stranded form. Sequences targeting human FUT genes are shown in Table 2.

TABLE 2

Table 2.

| Gene | siRNA | * | Nucleic acid sequence (5'->3') | SEQ ID NO |
|---|---|---|---|---|
| | random-FT | S | CCUUAUACCUAACGACAGACCCUUU | 21 |
| | | AS | AAAGGGUCUGUCGUUAGGUAUAAGG | 22 |
| FUT1 | FT1-1 | S | CCUCCAUAUCCAUCAAGACAGCUUU | 23 |
| | | AS | AAAGCUGUCUUGAUGGAUAUGGAGG | 24 |
| | FT-1-2 | S | CGGACUUGAGAGAUCCUUUCCUGAA | 25 |
| | | AS | UUCAGGAAAGGAUCUCUCAAGUCCG | 26 |
| FUT2 | FT2-1 | S | CACUCUGUCCCGGUUUCCUUCAGCA | 27 |
| | | AS | UGCUGAAGGAAACCGGGACAGAGUG | 28 |
| | FT2-2 | S | CAUCUCUCUUCUGUGAAGAUGCGUU | 29 |
| | | AS | AACGCAUCUUCACAGAAGAGAGAUG | 30 |
| FUT3 | FT3-1 | S | CCGCACUGCUAUUUCAGCUGCUGGU | 31 |
| | | AS | ACCAGCAGCUGAAAUAGCAGUGCGG | 32 |
| | FT3-2 | S | CAGACACGGUCAUCGUGCACCACUG | 33 |
| | | AS | CAGUGGUGCACGAUGACCGUGUCUG | 34 |
| FUT4 | FT4-1 | S | CGAAGCCUGGCAAGUAACCUCUUCA | 35 |
| | | AS | UGAAGAGGUUACUUGCCAGGCUUCG | 36 |
| | FT4-2 | S | GCUACAAGUUCUACCUGGCUUUCGA | 37 |
| | | AS | UCGAAAGCCAGGUAGAACUUGUAGC | 38 |
| FUT5 | FT5-1 | S | UAGGCCAGGGCUUAUGGCAGUGGAA | 39 |
| | | AS | UUCCACUGCCAUAAGCCCUGGCCUA | 40 |
| | FT5-2 | S | CAUCGUGCACCACUGGGAUAUCAUG | 41 |
| | | AS | CAUGAUAUCCCAGUGGUGCACGAUG | 42 |
| FUT6 | FT6-1 | S | GCUGUCUGACCACGCUGCUGUUUCA | 43 |
| | | AS | UGAAACAGCAGCGUGGUCAGACAGC | 44 |
| | FT6-2 | S | ACACGCGGCAUAGCGGCUUGGUUCA | 45 |
| | | AS | UGAACCAAGCCGCUAUGCCGCGUGU | 46 |
| FUT7 | FT7-1 | S | CGCCUCAUCUGCGGGUGGAUGUCUU | 47 |
| | | AS | AAGACAUCCACCCGCAGAUGAGGCG | 48 |
| | FT7-2 | S | GCGGGAACGUUUCUGUGCCAUCUGU | 49 |
| | | AS | ACAGAUGGCACAGAAACGUUCCCGC | 50 |
| FUT8 | FT8-1 | S | CAUCCCAGGUCUGUCGAGUUGCUUA | 51 |
| | | AS | UAAGCAACUCGACAGACCUGGGAUG | 52 |
| | FT8-2 | S | GAGAUAUCAUUGGUGUGGCUGGAAA | 53 |
| | | AS | UUUCCAGCCACACCAAUGAUAUCUC | 54 |

*Sense strand (S), Antisense strand (AS)

siRNA transfection experiment was performed using 100 nM of siRNA and TransMessenger Transfection Reagent (QIAGEN), in accordance with manufacturer's instructions. 40 hrs after the siRNA transfection, expression of FUT mRNA was analyzed by RT-PCR. Results of inhibition of expression of FUT genes by siRNA were shown in FIG. 10(*a*).

Of the cells wherein expression of various FUT genes was inhibited, absorption of $^{14}$C-fucose was suppressed in FUT3- or FUT6-knockdown cells. In addition, also in the FUT3- or FUT6-knockdown cells, production of CA19-9 was suppressed (FIG. 10(*b*)). In the figure, "NT" indicates no treatment, and "2", "3" and "6" indicate cells wherein siRNA of FUT2, FUT3 and FUT6 was transfected, respectively.

These results suggested that FUT3 and FUT6 are required in the production of CA19-9.

Example 8. Preparation of Fucosylated Liposomes Encapsulating Cy5.5 and CDDP

Fucosylated liposomes encapsulating Cy5.5 and cis-diaminedichloroplatinum(II) (cisplatin, CDDP) of the present invention were prepared as follows. First, CDDP3 was synthesized by a method of Dahara, S., Indian J. Chem. 1970; 7:193-194. Potassium tetrachloroplatinate(II) (4.15 g, 10 mmol) was dissolved in distilled water, potassium iodide (6.64 g, 40 mmol) was added, and stirred on ice under nitrogen atmosphere in the dark for 5 min. Then, aqueous ammonium solution (28%, 1.35 mL) was added to the reaction solution and stirred on ice for 3 hr. Yellow crystal formed was washed with distilled water and ethanol, dried at 40° C. under reduced pressure for 10 hr. In this step, 4.49 g of cis-diaminediiodoplatinum(II) (CDDP2) were obtained. After CDDP2 (2.41 g, 5 mmol) was suspended in distilled water, silver nitride (1.68 g, 9.9 mmol) was added, and stirred on ice in the dark for 24 hr. The reaction solution was filtered through filtering paper to remove silver iodide, and then concentrated using a rotary evaporator, giving white crystal. The crystal was washed with ice-cold distilled water and ethanol, and dried at 40° C. under reduced pressure for 10 hr. The final amount of production of CDDP3 was 1.0 g.

Next, dipalmitoylphosphatidylcholine (DPPC), cholesterol (Chol), ganglioside, dicetyl phosphate (DCP) and dipalmitoylphosphatidylethanolamine (DPPE) were mixed in a molar ratio of 35:40:5:15:5 (456 mg total lipids), and cholic acid (469 mg) was added to facilitate the micelle formation. The mixture was dissolved in a 30-mL methanol/chloroform solution (1:1, v/v). To obtain a lipid thin film, the solvent was evaporated at 37° C. using a rotary evaporator, and dried under reduced pressure. The lipid thin film obtained was dissolved in 30 mL of 10 mM N-[tris(hydroxymethyl)methyl]-3-aminopropanesulfonate (TAPS) buffer (pH 8.4) without NaCl, and subjected to ultrasonic treatment in order to obtain a homogenous micelle suspension.

FIG. 11 shows an encapsulation scheme of CDDP. 1 g of CDDP3 was completely dissolved in 70 mL of 10 mM TAPS buffer without NaCl (pH 8.4), and pH is adjusted to 8.4 using 1M NaOH. A solution of CDDP3 and Cy5.5 was added to the above micelle suspension. To remove cholic acid, free CDDP3 and free Cy5.5, the micelle solution was ultrafiltrated with 10 mM TAPS buffer (pH 8.4) using an ultrafiltration disc membrane (molecular weight cut off: 10,000) (Amicon PM10, Millipore) and an ultrafiltration cell holder (Amicon model 8200, Millipore) matched to the membrane. As a result, 100 mL of liposomes encapsulating CDDP3 were obtained. In order to convert CDDP3 in the liposome to CDDP, the obtained liposome was filtered through an ultrafiltration disc membrane (molecular weight cut off: 300,000) (Amicon XM300, Millipore), and the buffer was changed to 10 mM TAPS buffer comprising 150 mM NaCl (pH 8.4).

FIG. 12(a) shows a fucosylation scheme of liposomes. In the figure, HSA indicates human serum albumin, $BS_3$ indicates bis(sulfosuccinimidyl)suberate, "Tris" indicates tris (hydroxymethyl)aminomethane, and DTSSP indicates 3,3'-dithiobis(propionate 3-sulfosuccinimidyl).

A treatment to provide hydrophilic property and binding of L-fucose to the liposome surface were performed following the methods described in Yamazaki, N. J Membrane Sci 1989; 41:249-267 and Yamazaki et al., Methods Enzymol. 1994; 242:56-65. To exchange buffer, the solution was ultrafiltrated with 5 mM sodium hydrogen carbonate buffer (CBS, pH 8.5) through Amicon XM300 membrane. To 100 mL of the liposome solution, 100 mg of a crosslinking agent $BS_3$ were added, and stirred at 25° C. for 2 hr. After $BS_3$ bound to the liposome surface, the suspension was stirred at 4° C. overnight. 400 mg of Tris were added and stirred at 25° C. for 2 hr, and further stirred at 4° C. overnight so that Tris bound to $BS_3$. To remove residual Tris, the suspension was ultrafiltrated with 10 mM TAPS buffer (pH 8.4) through Amicon XM300 membrane.

Furthermore, in accordance with a method described in Hirai et al. 2007, supra, and Hirai et al. 2010, supra, human serum albumin (HSA) was bound to the liposome surface. To acidify the liposome surface, 108 mg of sodium periodate were added to 100 mL of the liposome solution, and stirred at 4° C. overnight. To remove residual sodium periodate, the suspension was ultrafiltrated with 10 mM phosphate buffered saline (PBS, pH 8.0) through Amicon XM300 membrane. Then, 200 mg of HSA were added to the suspension, and stirred at 25° C. for 2 hr. 31.3 mg of sodium cyanoborohydride were added and stirred at 25° C. for 2 hr, then further stirred at 4° C. overnight. To remove residual sodium cyanoborohydride, the solution was ultrafiltrated with CBS buffer (pH 8.5) through Amicon XM300 membrane.

L-fucose was bound to the liposome surface by a crosslinking agent DTSSP. 100 mg of DTSSP were added to 100 mL of the liposome solution, stirred at 25° C. for 2 hr, then further stirred at 4° C. overnight. To remove residual DTSSP, the solution was ultrafiltrated with CBS buffer (pH 8.5) through Amicon XM300 membrane. Fucose reducing terminal was aminated by glycosylamination reaction. 8 mg of fucose were dissolved in 2 mL of distilled water, 1 g of ammonium hydrogen carbonate was added, and stirred at 37° C. for 3 days. Aminated fucose was added such that its final concentration became 10, 25, 50, 100 g/mL, and stirred at 25° C. for 2 hr. Thereafter, in order to repeatedly make the liposome surface hydrophilic, Tris was added such that its final concentration became 132 mg/mL, and stirred at 4° C. overnight. To remove residual fucose and Tris, the solution was ultrafiltrated with HEPES buffer (pH 7.2) through Amicon SM300 membrane.

Non-fucosylated liposomes were prepared similarly to the above-mentioned CDDP-encapsulated fucosylated liposomes, excluding the step of fucose binding. CDDP-encapsulated liposomes and CDDP-encapsulated fucosylated liposomes were ultrafiltrated with 20 mM HEPES buffer (pH 7.2) using Amicon XM300 membrane, and 10-times concentrated.

Example 9. Physiochemical Characteristics of Cy5.5-Encapsulated Fucosylated Liposomes Liposomes were prepared by modified cholic acid dialysis, so that their final concentrations became 25 (F25), 50 (F50), and 100 (F100) μg/mL, as shown in FIG. 12(a), and aminated fucose was crosslinked to these liposomes via DTSSP. Furthermore, to make the liposome surface hydrophilic, $BS_3$ and Tris were bound. By making the liposome surface hydrophilic, intake of liposomes into the reticuloendothelial system of the liver and spleen, macrophages and vascular endothelial cells can be prevented, and furthermore, adsorption of opsonic proteins in the plasma can be prevented, thereby enabling to keep the liposomes in the blood stream for a longer period of time. From the result of electron microscopic observation shown in FIG. 12(b), almost all fucosylated liposomes were spherical, and the size of the Cy5.5-encapsulated liposomes was approximately 80 nm.

Physiochemical characteristics of Cy5.5-included fucosylated liposomes were shown in FIG. 13 and Table 3.

TABLE 3

| (Cy5.5-encapsulated liposomes and Cy5.5-encapsulated fucosylated liposomes were 10 times concentrated) | | | | |
|---|---|---|---|---|
| Fucose concentration in the binding reaction (μg/mL) | 0 (F0) | 25 (F25) | 50 (F50) | 100 (F100) |
| Lipid concentration (mg/mL)[a] | 3.4 | 3.8 | 3.7 | 3.8 |
| Particle size (nm) | 73 | 98 | 72 | 73 |
| Zeta potential (mV)[b] | −64 | −43 | −45 | −46 |
| Protein concentration (mg/mL)[c] | 0.7 | 0.7 | 0.8 | 0.7 |
| Protein/lipid weight ratio[d] | 0.21 | 0.18 | 0.22 | 0.18 |

[a]Total cholesterol was measured using a cholesterol E test Wako kit.
[b]Zeta potential was measured using Malvern Nano-S90.
[c]Protein mass was measured at OD 680 nm.
[d]Protein/lipid weight ratio was calculated by the equation below: Protein concentration (mg/mL)/Lipid concentration (mg/mL)

An average particle size and zeta potential of liposomes prepared in water were measured at 25° C. using a dynamic light scattering photometer calibrated with standard latex nanoparticles (Zetasizer Nano-S90, Malvern). The particle sizes measured by Zetasizer Nano-S90 coincided with microscopic observation results, and zeta potential that indicates an electric charge at the surface of liposome membrane was negative at −40 mV or less in each liposome. The particle size distribution after 6-month storage at 4° C. was almost the same as that immediately after preparation, indicating a stable nature of these liposomes.

Example 10. Introduction of Cy5.5 Encapsulated in Fucosylated Liposomes

To investigate specific delivery by fucosylated liposomes, a fucosylated liposome that encapsulates Cy5.5 was transfected in CA19-9 producing or CA19-9 non-producing pancreatic adenocarcinoma cells. AsPC-1 cells were incubated with Cy5.5-encapsulated fucosylated liposomes for 2 hr, then washed twice with phosphate buffered saline, and visualized under a fluorescence microscope (FIG. 14). In the AsCP-1 cells which secrete a large amount of CA19-9, fucosylated liposomes (F50), but not fucosylated liposomes (F0) efficiently introduced Cy5.5.

Flow cytometry results (FIG. 15) also showed that fucosylated liposomes (F50) most efficiently transfected Cy5.5 in CA19-9 producing cells (FIG. 15(a)), but not in CA19-9 non-producing cells (FIG. 15(b)). Moreover, because excessive fucose inhibited the efficient introduction (in the figure, +Fuc×100), it is suggested that the introduction of Cy5.5 by fucosylated liposomes is mediated in a fucose receptor-dependent manner.

Example 11. Physiochemical Characteristics of CDDP-Encapsulated Fucosylated Liposomes Table 4 shows physiochemical characteristics of CDDP-encapsulated fucosylated liposomes. The particle size of the CDDP-encapsulated fucosylated liposomes was approximately 200 nm, and the final concentration of CDDP was estimated to be approximately 2 mg/mL.

TABLE 4

Initial amount of CDDP3 (mg) used for the preparation of 1 mL of CDDP-encapsulated liposomes: 100 mg
(CDDP-encapsulated liposomes and CDDP-encapsulated fucosylated liposomes were 10 times concentrated)

| Fucose concentration in the binding reaction (μg/mL) | 0 (F0) | 25 (F25) | 50 (F50) | 100 (F100) |
|---|---|---|---|---|
| Lipid concentration (mg/mL)$^a$ | 8.2 | 8.3 | 8.4 | 8.9 |
| Particle size (nm)$^b$ | 232 | 235 | 234 | 229 |
| PDI$^c$ | 0.17 | 0.17 | 0.19 | 0.18 |
| Zeta potential (mV)$^d$ | −64 | −56 | −63 | −62 |
| CDDP concentration (mg/mL)$^e$ | 2.1 | 1.8 | 2.1 | 2.0 |
| CDDP encapsulation efficiency$^f$ | 2.1 | 1.8 | 2.1 | 2.0 |
| CDDP/lipid weight ratio$^g$ | 0.26 | 0.22 | 0.25 | 0.22 |

$^a$Total cholesterol was measured using a cholesterol E test Wako kit.
$^b$Encapsulation of CDDP3 into liposomes, followed by conversion to CDDP in NaCl-containing TAPS buffer.
$^c$PDI was measured by photon correlation spectrum using Malvern Nano-S90.
$^d$Zeta potential was measured using Malvern Nano-S90.
$^e$An amount of platinum was measured by SHIMADZU AA-6700 atomic absorption spectrometer, and an amount of CDDP was calculated by the equation below: Amount of platinum × (300/195) wherein "300" indicates the molecular weight of CDDP, and "195" indicates the molecular weight of platinum.
$^f$Encapsulation efficiency was calculated by the equation below: (Amount of CDDP in liposome/initial amount of chemical substance) × 100
$^g$CDDP/lipid weight ratio was calculated by the equation below: CDDP concentration (mg/mL)/Lipid concentration (mg/mL)

Analysis of lipid concentration was carried out by the following procedure. CDDP-encapsulated liposomes and CDDP-encapsulated fucosylated liposomes were measured using a cholesterol E-test Wako kit under the presence of 0.5% Triton X-100, in terms of total cholesterol. Lipid concentrations were calculated from the molar ratio of each lipid (4.5) by Eq. (1).

$$\text{Lipid concentration (mg/mL)} = \text{Cholesterol concentration (mg/mL)} \times 4.5 \quad \text{Eq. (1)}$$

Measurement of CDDP, and calculation of CDDP concentration and encapsulation efficiency were carried out as follows. Fucosylated liposomes encapsulating CDDP were 10,000 times diluted with distilled water, and platinum concentration was measured using an automated flameless atomic absorption spectrometer (FAAS) (Model AA-6700, SHIMADZU). Cis-diaminedichloroplatinum was used as a standard substance. A calibration curve of platinum concentration of 50-250 ng/mL was made prior to analysis of each sample. A CDDP amount was calculated by Eq. (2).

$$\text{CDDP concentration} = A \times (300/195) \quad \text{Eq. (2)}$$

In Eq. (2), "A" indicates platinum concentration, "300" indicates the molecular weight of CDDP, and "195" indicates the molecular weight of platinum.

Encapsulation efficiency and weight ratio of CDDP to lipid were calculated by Eqs. (3) and (4), respectively.

$$\text{Encapsulation efficiency (\%)} = (\text{Amount of CDDP in liposome})/(\text{Initial amount of CDDP}) \times 100 \quad \text{Eq. (3)}$$

$$\text{Weight ratio of CDDP to lipid} = \text{CDDP concentration (mg/mL)/Lipid concentration (mg/mL)} \quad \text{Eq. (4)}$$

Example 12. Effects of CDDP-Encapsulated Fucosylated Liposomes on Various Pancreatic Cancer Cell Lines FIG. 16 shows results of investigation of cytotoxic effects of CDDP-encapsulated fucosylated liposomes by WST-1 assay. $2 \times 10^4$ cells from each cell line (AsPC-1, etc.) were transferred to a 24-well plate, and cultured for 1 day with RPMI-1640 supplemented by 10% fetal bovine serum, 5% L-glutamine, and 1% antibiotics. Then, the cells were incubated with various administration amounts of CDDP-encapsulated fucosylated liposomes or CDDP-encapsulated liposomes. After 2 hr incubation, the cells were washed twice with PBS, and finally suspended in RPMI-1640 comprising serum and antibiotics. After 72 hr culturing, WST-1 reagent was added, and growth assay was performed in accordance with the method of Sato, Y. Nat. Biotechnol. 2008; 26(4): 431-42. The experiments were triplicated and repeated at least twice.

As a result, CDDP-encapsulated liposomes (F50) (50 μg/mL of fucose bound to liposome) exhibited the highest cytotoxic effect (FIG. 16(a)). In addition, in CA19-9 producing cells (PK45H, AsPC-1 and KP4), CDDP-encapsulated liposomes (F50) are more efficient than CDDP-encapsulated liposomes (F0), indicating a fucose-dependent cytotoxic effect (FIG. 16(b)).

Example 13. Preparation of Subcutaneous Pancreatic Cancer Model

In the preparation of subcutaneous model, AsPC-1 cells ($2 \times 10^6$ cells) were seeded on the back side of a mouse (4-6 weeks old). Bioluminescence was measured from 0 to 4 days after injection, and the mice were randomly divided into multiple groups before starting the treatment. In vivo optical imaging was performed using Xenogen-IVIS-cooled COD optical system (Xenogen-IVIS). Bound CDD (such as CDDP in fucosylated liposomes) or free CDDP was in a dose of 2 mg/kg for each administration. Injection was performed twice in the first week, then twice in the second and third weeks. All the mice used week, sacrificed on the next day of the final injection prior to the final measurement of bioluminescence.

Example 14. Accumulation of Fucosylated Liposomes in Tumor by Mannose Treatment Delivery of fucosylated liposomes in a pancreatic cancer model mouse was investigated, and it was observed that Cy5.5 encapsulated by fucosylated liposomes accumulates in the liver, and Cy5.5 accumulation in the tumor lesions is decreased. The present inventors predicted that this capture of fucosylated liposomes in the liver is caused by lectins present in non-parenchymal cells.

Therefore, in order to suppress the incorporation of fucose via lectin, treatment with an excessive amount of mannose was performed before and after injection of fucosylated liposomes. Cy5.5-encapsulated fucosylated liposomes or Cy5.5-encapsulated liposomes were administered via the tail vein (50 μl/mouse). The region of the tumor in the same mouse (behind the lesions of both flanks) was observed before injection and 0-96 hr after injection, using an IVIS imaging system. D-mannose (SIGMA) was diluted in PBS, and 50 μL (0.02 mg/μL) were injected in the tail vein of the mouse. The amount of mannose administered was 1000 times excess relative to fucose.

As a result, when fucosylated Liposome was used in combination with mannose, accumulation of Cy5.5 in the tumor and reduction of Cy5.5 in the liver were observed (FIG. 17, FIG. 18(a)). Accumulation of Cy5.5 was maintained up to one week after the administration of fucosylated liposomes. Furthermore, as a result of microscopic observation of tumor tissue, accumulation of Cy5.5 was confirmed (FIG. 18(b)).

The impact of excessive amount of mannose on the transfection efficiency of fucosylated liposomes were also investigated using flow cytometry, but no apparent impact was observed (FIG. 19). Mannose is phosphorylated to mannose-6-phosphate by hexokinase, then converted to fructose-6 phosphate that is used in the glycolysis. However, 90% of the mannose taken into the body is excreted unchanged into urine within 30-60 min, and 99% of the remaining mannose is excreted within 8 hr. The amount of mannose administered corresponds to 1 mg of mannose for a mouse, which corresponds to 0.6 g for a human, and no apparent adverse effect was observed with this amount.

Table 5 shows results of hematologic/biochemical analyses during the treatment period. Samples were collected from mouse orbital venous plexus. In the table, WBC represents white blood cell count, RBC represents red blood cell, count, Hb represents hemoglobin concentration, PLT represents Platelet count, AST represents aspartate aminotransferase concentration, represents alanine aminotransferase concentration, Bil represents bilirubin concentration, BS represents blood glucose, Cr represents creatinine concentration.

TABLE 5

| | WBC (/ul) | RBC (×10$^4$/ul) | Hb (g/dl) | PLT (×10$^4$/ul) | AST (IU/L) | ALT (IU/L) | Bil (mg/dL) | BS (mg/dL) | Cr (mg/dL) |
|---|---|---|---|---|---|---|---|---|---|
| Day 2 | | | | | | | | | |
| NT | 6400 | 942 | 16 | 28.3 | 300 | 45 | 0.2 | 30 | 0.4 |
| F0, CDDP 2 mg | 3600 | 866 | 14.4 | 13.9 | 450 | 45 | 0.2 | 50 | 0.7 |
| F50, CDDP 2 mg | 3700 | 973 | 16.3 | 28.7 | 235 | 40 | 0.2 | 90 | 0.8 |
| Day 9 | | | | | | | | | |
| NT | 2700 | 865 | 14.5 | 13.7 | 340 | 50 | 0.2 | 55 | 0.5 |
| F0, CDDP 2 mg | 3200 | 893 | 14.2 | 12.1 | 305 | 45 | 0.2 | 70 | 0.5 |
| F50, CDDP 2 mg | 5600 | 1017 | 16.6 | 49.2 | 190 | 25 | 0.2 | 100 | 0.8 |
| Day 16 | | | | | | | | | |
| NT | 3900 | 1051 | 14.8 | 52.9 | 355 | 16 | 0.2 | 94 | 0.5 |
| F0, CDDP 2 mg | 6800 | 856 | 13.5 | 27.2 | 178 | 56 | 0.2 | 123 | 0.4 |
| F50, CDDP 2 mg | 7800 | 895 | 12.3 | 35.3 | 374 | 20 | 0.2 | 106 | 0.5 |

Since the serum of a heal comprises average 54.1±11.9 μM of mannose, the amount of mannose used is a small amount relative to the total mannose in the human body.

Example 15. Inhibition of Tumor Growth by CDDP-Encapsulated Fucosylated Liposomes in Xenograft Model In pancreatic cancer model mice (AsPC-1), effects of suppression of tumor growth by CDDP, CDDP-encapsulated liposomes (F0), and CDDP-encapsulated liposomes (F50) were compared (FIG. 20). A solution of CDDP (2 mg/kg), CDDP-encapsulated liposomes (F0) (2 mg/kg CDDP), or CDDP-encapsulated liposomes (F50) (2 mg/kg CDDP) was injected via the tail vein of a mouse twice a week. Mannose treatment was carried out 1 hr before administration of liposomes, simultaneously with the administration, and 1 day after the administration. Tumor volumes were measured at 4, 8, 11, 15, 18 and 22 days after the transplant. As a result, CDDP-encapsulated fucosylated liposomes almost completely inhibited the tumor growth (FIG. 20).

In the tumors treated with CDDP-encapsulated fucosylated liposomes (F50) it was observed by TUNEL staining that the number of apoptotic cells was larger than that in other tumors (FIG. 21(a)). In addition, measurement of the concentration of CDDP in tumor cells confirmed that CDDP was delivered to and accumulated in the tumor cells (FIG. 21(b)). The measurement was performed by ICP analysis, using tumors collected from the mice sacrificed on the next day of the last injection.

In addition, shown in Table 5, administration of mannose or CDDP-encapsulated fucosylated liposomes does not have any adverse effects.

Example 16. Investigation of CA19-9 Concentration in Supernatant of Various Colorectal Cancer Cell Cultures $5 \times 10^6$ cells from each colorectal cancer cell line were seeded in a 25-cm² flask, and cultured with 3 ml of a serum-free medium. Opti-MEM® for 48 hr. The concentrations of CA19-9 in the supernatant of cultures were investigated by ELISA. Results are shown in FIG. 22 and Table 6.

TABLE 6

| Cell line | CA19-9 concentration (ng/ml) |
|---|---|
| SW1116 | 4620 |
| LS174T | 3080 |
| COLO205 | 2170 |
| LS180 | 890 |
| HT-29 | 39 |
| HCT-15 | <5 |

On the basis of the above results, COLO205 was used as the high-producing cell line and HT-29 was used as the low-producing cell line in the following investigations.

Example 17. Introduction of Cy5.5 Encapsulated in Fucosylated Liposomes

To investigate specific delivery by fucosylated liposomes, first, introduction of Cy5.5 into cells was confirmed by fluorescence microscopy. $1 \times 10^5$ COLO205 cells were seeded on a chamber slide, and incubated with the Cy5.5-included fucosylated liposomes obtained in Example 8 for 2 hr, then washed with phosphate buffered saline (PBS). After fixation with 4% paraformaldehyde, the cells were washed with PBS, counterstained with DAPI, and visualized by a fluorescence microscope (FIG. 23). In the case of liposomes without fucose (F0), almost no red fluorescence of Cy5.5 is observed in the cells; however, it is shown that the fucosylated liposomes (F25, F50 and F100) efficiently introduced Cy5.5.

Specific delivery by fucosylated liposomes was also investigated by flow cytometry. $1 \times 10^6$ COLO205 cells were seeded in a 6-well culture flask, and cultured for 2 hr after addition of Cy5.5-included fucosylated liposomes. After culturing, the cells were washed with PBS and the cell suspension was prepared, then Cy5.5-positive cells were detected by FACSCalibur™ flow cytometer (BD Biosciences, San Jose, Calif., USA) (FIG. 24). The results obtained also confirmed efficient introduction of Cy5.5 into cells by fucosylated liposomes.

Example 18. Effects of CDDP-Encapsulated Fucosylated Liposomes on Various Colorectal Cancer Cell Lines Using WST-1 assay, cytotoxic effects of CDDP-encapsulated fucosylated liposomes were investigated. $2 \times 10^4$ cells of each type were seeded in a 96-well culture flask, and the cells were incubated with liposomes encapsulating CDDP, which are not fucosylated (F0), or which are fucosylated with various degrees (F50, F100). After 2 hr incubation, the cells were washed with PBS, and after replacement of the culture solution (10% FBS-supplemented RPMI1640 medium for COLO205, and 10% FBS-supplemented McCoy's 5A medium for HT-29), further 72 hr of culturing was performed; then an assay using WST-1 reagent was performed similarly to Example 12, and viable cells were counted. From the results shown in FIG. 25, it was confirmed that a higher cytocidal effect by CDDP-encapsulated fucosylated liposomes was observed in the CA19-9 high-producing cell line, compared to the CA19-9 low-producing cell line.

In another experiment, under the same conditions, cells were incubated with fucosylated liposomes including various concentrations of CDDP (F100) or with non-fucosylated liposomes including CDDP (F0), and viable cells were counted similarly (FIG. 26). As a result, it has been clarified that CDDP-included fucosylated liposomes exhibit a cytocidal effect in a dose-dependent manner.

Example 19. Accumulation of Fucosylated Liposomes in Tumor by Mannose Treatment $1 \times 10^6$ LS180 cells were subcutaneously transplanted at each of two places on the back of a nude mouse (5 weeks old, Sankyo Lab Services). After tumor size reached 5 mm (approximately 2 weeks after the transplant), 50 µl of Cy5.5-included fucosylated liposomes (F100) were injected through the tail vein (Cy5.5: 0.3 µg, equivalent to 1 µg of fucose). In the mannose treatment group (F100+M) 5 mg/100 µl of D-Mannose (SIGMA) dissolved in PBS were intraperitoneally administered 1 hr before liposome administration, and were administered again via the tail vein at the time of liposome administration (total 10 mg/200 µl). In each administration, mannose was 5000-times excess to the fucose. On clays 2, 5 and 14 after the liposome administration, accumulation of Cy5.5 was observed by an in vivo image analyzer (IVIS® Lumina, Caliper Life Sciences). FIG. 27 shows results of accumulation of Cy5.5 in the liver, and FIG. 28 shows results of accumulation in tumors. These results clarified that when mannose and fucosylated liposomes are used in combination, accumulation of Cy5.5 in the liver decreases (FIG. 27), whereas that in the tumors significantly increases (FIG. 28).

Example 20. Inhibition of Tumor Growth by CDDP-Encapsulated Fucosylated Liposomes $1 \times 10^6$ LS180 cells were subcutaneously transplanted at each of two places on the back of a nude mouse (5 weeks old, Sankyo Lab Services). After tumor size reached 5 mm (approximately 2 weeks after the transplant), the nice were divided into 5 groups (each containing 6 mice): non-treatment group (NT), CDDP-alone group (CDDP), CDDP-included non-fucosylated liposome group (F0-CDDP), CDDP-included fucosylated liposome groups (F50-CDDP and F100-CDDP), and the mice (except those in the non-treatment group) were injected with 100 µg of each treatment agent that is equivalent to 2 mg/kg of CDDP via the tail vein twice a week. Regarding the mannose treatment 5 mg/100 µl of D-mannose (SIGMA) dissolved in PBS were intraperitoneally administered 1 hr before administration of each treatment agent, and were administered again via the tail vein at the time of administration of each treatment agent (total 10 mg/200 µl). Tumor size was measured on days 4, 8, 11, 15, 18 and 22 after beginning of the treatment. Results shown in FIG. 29 clarified that the tumor volume in the F100-CDDP group to which CDDP-included fucosylated liposomes were administered significantly decreased compared to that in the non-treatment group, CDDP-alone group and CDDP-included non-fucosylated liposome group.

Example 21. Investigation of CA19-9 Concentration in Supernatant of Various Biliary Tract Cancer Cell Cultures $5 \times 10^6$ cells from each biliary tract cancer cell line were seeded in a 25-cm$^2$ flask, and cultured with 3 ml of a serum-free medium Opti-MEM® for 48 hr. The concentrations of CA19-9 in the supernatant of cultures were investigated by ELISA. Results are shown in FIG. 30. Based on the results, a high-producing cell line HuCCT1 was used in the following investigation.

Example 22. Introduction of Cy5.5 Encapsulated in Fucosylated Liposomes

To investigate specific delivery by fucosylated liposomes, introduction of Cy5.5 into cells was confirmed by flow cytometry. $1 \times 10^6$ HuCCT1 cells were seeded in a 6-well culture flask, and the Cy5.5-encapsulated fucosylated liposomes obtained in Example 8 were added and cultured for 2 hr. After culturing, the cells were washed with PBS and the cell suspension was prepared, and Cy5.5-positive cells were detected by FACSCalibur™ flow cytometer (BD Biosciences, San Jose, Calif., USA) (FIG. 31). As a result, it has been clarified that Cy5.5 was introduced more efficiently by fucosylated liposomes (F50) than by non-fucosylated liposomes (F0). In addition, the finding that excessive fucose inhibited the efficient introduction (in the figure, F50+Fuc) indicates that introduction of Cy5.5 by fucosylated liposomes is fucose-receptor dependent.

Example 23. Investigation of CA19-9 Concentration in Supernatant of Various Stomach Cancer Cell Cultures $5 \times 10^6$ cells from each stomach cancer cell line were seeded in a 25-cm$^2$ flask, and cultured with 3 ml of a serum-free medium Opti-MEM® for 48 hr. The concentrations of CA19-9 in the supernatant of cultures were investigated by ELISA. Results are shown in Table 7.

TABLE 7

| Cell line | CA19-9 concentration (ng/ml) |
| --- | --- |
| JR-St | 1645 ± 54 |
| HSC-39 | 436 ± 12 |
| NCI-N87 | 204 ± 11 |
| MKN45 | <5 |
| MKN74 | <5 |
| NUGC-4 | <5 |
| KATO-III | 15 ± 4 |

On the basis of the above results, JR-St was used as the high-producing cell line and MKN45 was used as the low-producing cell line in the following investigations.

Example 24. Introduction of Cy5.5 Encapsulated in Fucosylated Liposomes

To investigate specific delivery by fucosylated liposomes, introduction of Cy5.5 into cells was confirmed by flow cytometry and fluorescence microscopy.

In flow cytometry, $1 \times 10^6$ cells of each type were seeded in a 6-well culture flask, the Cy5.5-included fucosylated liposomes obtained in Example 8 were added, and incubated for 1 hr. After incubation, the cells were washed with PBS and the cell suspension was prepared, then Cy5.5-positive cells were detected by FACSCalibur™ flow cytometer (BD Biosciences, San Jose, Calif., USA). From the results of the charts on the left side of FIGS. 32 and 33, it is shown that, in the high-producing cell line JR-St cells, efficient introduction of Cy5.5 by fucosylated liposomes (F50 and F100) was achieved compared to non-fucosylated liposomes (F0); whereas in the low-producing cell line MKN45 cells, introduction of Cy5.5 even by the fucosylated liposomes (F50 and F100) was at a low level similar to that by non-fucosylated liposomes (F0). In addition, the fact that excessive fucose inhibited the efficient introduction of Cy5.5 by fucosylated liposomes in JR-St cells (in the figure, F100+Fuc) indicates that introduction of Cy5.5 by fucosylated liposomes is fucose-receptor dependent.

In fluorescence microscopy, $1 \times 10^5$ cells of each type were seeded on a chamber slide, and incubated with the Cy5.5-included fucosylated liposomes obtained in Example 8 for 1 hr, then washed with phosphate buffered saline (PBS). After fixation with 4% paraformaldehyde, the cells were washed with PBS, counterstained with DAPI, and visualized by a fluorescence microscope. From the fluorescence microscopic images on the right side of FIGS. 34 and 35, it is shown that, in the high-producing cell line JR-St cells, a larger amount of red fluorescence of Cy5.5 is observed in the cells treated with fucosylated liposomes (F50 and F100) compared to non-fucosylated liposome-treated cells (F0); whereas in the low-producing cell line MKN45 cells, the amount of Cy5.5 introduced into the cells by the fucosylated liposomes (F100) is at a low level similar to that by non-fucosylated liposomes (F0). In addition, the fact that almost no introduction of Cy5.5 into JR-St cells was observed due to the excessive fucose (in the figure, F100+Fuc) indicates that introduction of Cy5.5 by fucosylated liposomes is fucose-receptor dependent, thus supporting the results obtained by flow cytometry.

Example 25. Effects of CDDP-Encapsulated Fucosylated Liposomes on Various Stomach Cancer Cell Lines Using WST-1 assay, cytotoxic effects of CDDP-encapsulated fucosylated liposomes were investigated. $2 \times 10^4$ cells of each type were seeded in a 96-well culture flask, and the cells were incubated with liposomes encapsulating CDDP, which were not fucosylated (F0), or which were fucosylated with various degrees (F25, F50, or F100). After 1 hr incubation, the cells were washed with PBS, and after replacement of the culture solution (10% FBS-supplemented RPMI1640 medium), further 72 hr of culturing was performed; then an assay using WST-1 reagent was performed similarly to Example 12, and viable cells were counted. As shown by the results of the graphs on the left side of FIGS. 34 and 35, a higher cytocidal effect by CDDP-included fucosylated liposomes was observed in the CA19-9 high-producing cell line (JR-St), compared to the CA19-9 low-producing cell line (MKN45).

In another experiment, under the same conditions, cells were incubated with various concentrations (0, 0.1, 1, 10 or 100 μM) of CDDP-included fucosylated liposomes (F100) or CDDP-included non-fucosylated liposomes (F0), and viable cells were counted similarly (graphs on the right side of FIGS. 34 and 35). As a result, it has been clarified that CDDP-included fucosylated liposomes exhibit a dose-dependent cytocidal effect in the CA19-9 high-producing cell line.

Example 26. Investigation of Expression of CD33 and Notch-1 in Cells of Various Leukemia Cell Lines $1 \times 10^6$ cells of each leukemia cell line were washed with 0.1% BSA/PBS, and labeled by the reaction for 10 min with 10 µl of antibodies (PE-conjugated CD33 antibody (R&D) and FITC-conjugated Notch-1 antibody (R&D)) in 1 ml of PBS, then the cells were washed with PBS and the cell suspension was prepared. This cell suspension was subjected to FACSCalibur™ flow cytometer (BD Biosiences, San Jose, Calif., USA) to detect positive cells, and they were analyzed by CellQuest Pro software (BD Biosciences). As clearly demonstrated by the results of FIG. 36, both CD33 and Notch-1 were expressed in each of HL-60, KG-1 and RPMI8226 cells, and expression rate of Notch-1 was particularly high in HL-60 cells; however, almost no CD33 and Notch-1 were expressed in MOLT-4.

Example 27. Expression of Fucosyltransferase in Various Leukemia Cell Lines

For each leukemia cell line, total RNA was extracted from $1 \times 10^6$ cells and subjected to RT-PCR. Using random hexamer (100 µM) and MMLV (GIBCO), total RNA (1 µg) was reverse-transcribed in accordance with manufacturer's instruction. Primers for each fucosyltransferase are listed in the table below.

TABLE 8

Table 8. Primers for FUT1-10 and POFUT1

| Name | Type | Sequence |
|---|---|---|
| FUT1 | Upper strand | ATGTGGCTCCGGAGCCATCGTCAG (SEQ ID NO 1) |
| | Lower strand | AGGATCTCTCAAGTCCGCGTACTC (SEQ ID NO 2) |
| FUT2 | Upper strand | CTAGCGAAGATTCAAGCCATGTGG (SEQ ID NO 3) |
| | Lower strand | GACGTACTCCCCCGGGATGTG (SEQ ID NO 4) |
| FUT3 | Upper strand | ATGGATCCCCTGGGTGCAGCCAAG (SEQ ID NO 5) |
| | Lower strand | TCAGGTGAACCAAGCCGCTATGCT (SEQ ID NO 6) |
| FUT4 | Upper strand | GTGCCCGAAATTGGGCTCCTGCAC (SEQ ID NO 7) |
| | Lower strand | GAAGGAGGTGATGTGGACAGCGTA (SEQ ID NO 8) |
| FUT5 | Upper strand | CTTATGGCAGTGGAACCTGTCACC (SEQ ID NO 9) |
| | Lower strand | CCAGCCGTAGGGCGTGAAGATGTC (SEQ ID NO 10) |
| FUT6 | Upper strand | CCCACTGTGTACCCTAATGGGTCC (SEQ ID NO 11) |
| | Lower strand | CTCTCAGGTGAACCAAGCCGCTAT (SEQ ID NO 12) |
| FUT7 | Upper strand | TCGGACATCTTTGTGCCCTATG (SEQ ID NO 13) |
| | Lower strand | CGCCAGAATTTCTCCGTAATGTA (SEQ ID NO 14) |
| FUT8 | Upper strand | TGCCTGGGGGACCTTGCTGT (SEQ ID NO 15) |
| | Lower strand | CCCGCCAATCCTGCTCCA (SEQ ID NO 16) |
| FUT9 | Upper strand | CTTACCGCCGTGATTCAGAT (SEQ ID NO 55) |
| | Lower strand | AATGCTTGCCCGTAGGTATG (SEQ ID NO 56) |
| FUT10 | Upper strand | TCGGACATCTTTGTGCCCTATG (SEQ ID NO 57) |
| | Lower strand | TTTCAGTGGCCTCCAGAACT (SEQ ID NO 58) |
| POFUT1 | Upper strand | GAAGGAAGGAAACCCCTTTG (SEQ ID NO 59) |
| | Lower strand | TCTCCCGTCTTCACCATTTC (SEQ ID NO 60) |
| β-actin | Upper strand | ATCTGGCACCACACCTTCTACAATGAGCTGCG (SEQ ID NO 17) |
| | Lower strand | CGTCATACTCCTGCTTGCTGATCCACATCTGC (SEQ ID NO 18) | cDNA was amplified with 25-30 cycles using Pfu Turbo (Stratagene), 0.2 mM of each dNTP, and 100 µM of each primer. Each cycle consists of 30 sec at 95° C., 30 sec at 55° C., and 60 sec at 72° C.

PCR products were subjected to 1.2% agarose-gel electrophoresis, and expression was observed under UV. From the results shown in FIG. 37, it is clarified that POFUT1, which is considered to be involved in the fucosylation of Notch-1, is expressed in each of Notch-1-positive HL-60, KG-1 and RPMI8226 cells, whereas almost no POFUT1 is expressed in Notch-1-negative MOLT-4. Based on this finding, HL-60 was used as the Notch-1 expressing strain, and MOLT-4 was used as the Notch-1 non-expressing strain in the following investigations.

Example 28. Introduction of Fluorescent Labels Encapsulated in Fucosylated Liposomes To investigate specific delivery by fucosylated liposomes, introduction of fluorescent labels into cells was confirmed by flow cytometry and fluorescence microscopy.

In flow cytometry, $1 \times 10^6$ cells of each type were seeded in a 6-well culture flask, Cy5.5-included fucosylated liposomes (HL-60 cells) obtained in Example 8 or FAM-included fucosylated liposomes (MOLT-4 cells) obtained similarly to Example 8 were added, and they were incubated for 2 hr. After incubation, the cells were washed with PBS, and the cell suspension was prepared, then fluorescent-labeled positive cells were detected by FACSCalibur™ flow cytometer (BD Biosciences, San Jose, Calif., USA). From the results shown in FIG. 38, it is clarified that in Notch-1 expressing HL-60 cells, fluorescent labels are efficiently introduced by fucosylated liposomes (F25 and F50) compared to non-fucosylated liposomes (F0); whereas in Notch-1 non-expressing MOLT-4 cells, introduction of fluorescent labels even by the fucosylated liposomes is at a low level similar to the case of non-fucosylated liposomes.

In fluorescence microscopy, $1\times10^5$ cells of each type were seeded on a chamber slide, and incubated with the FAM-included fucosylated liposomes obtained similarly to Example 8 for 2 hr, then washed with phosphate buffered saline (PBS). After fixation with 4% paraformaldehyde, the cells were washed with PBS, counterstained with DAPI, and visualized by a fluorescence microscope. In the fluorescence microscopic images in FIG. 39, in Notch-1 expressing cell line HL-60 cells, a significantly larger amount of fluorescence of FAM was observed in the fucosylated liposome-treated cells (F25 and F50), compared to non-fucosylated liposome-treated cells (F0); whereas in Notch-1 non-expressing cell line MOLT-4 cells, the amount of FAM introduced in the cells even by the fucosylated liposomes was at a low level similar to that by the non-fucosylated liposomes, thus supporting the results of flow cytometry.

Example 29. Effects of Doxorubicin-Encapsulated Fucosylated Liposomes on Various Leukemia Cell Lines Using WST-1 assay, cytotoxic effects of doxorubicin-encapsulated fucosylated liposomes were investigated. Doxorubicin-included fucosylated liposomes were prepared by a method similar to Example 8. $2\times10^4$ cells of each type were seeded in a 96-well culture flask, and the cells were incubated with various concentrations of doxorubicin-encapsulated fucosylated liposomes (F-DOX) or with doxorubicin alone (DOX). After 2 hr incubation, the cells were washed with PBS, and after replacement of the culture solution (10% FBS-supplemented RPMI1640 medium), further 72 hr of culturing was performed; then an assay using a WST-1 reagent was performed similarly to Example 12, and viable cells were counted. As shown in FIG. 40, in the Notch-1 expressing cell line (HL-60), doxorubicin-included fucosylated liposomes (F-DOX) exhibited a significant dose-dependent cytocidal effect compared to doxorubicin alone (DOX). In contrast, in the Notch-1 non-expressing cell line (MOLT-4), such a dose-dependent cytocidal effect was not observed.

Example 30. Investigation of Expression of CD33 and Notch-1 in Samples from Leukemia Patients Regarding samples from leukemia patients, peripheral blood was collected after obtaining patient consent, then mononuclear cells were separated by Ficoll-Hypaque and stored in liquid nitrogen before use. Conditions of patients from which samples were collected are listed in Table 9 below.

TABLE 9

| case No. | Diagnosis | sex | Age | Tx | |
|---|---|---|---|---|---|
| 1 | AML M1 | M | 81 | BSC | dead |
| 2 | AML M2 | F | 57 | IDR/AraC | alive |
| 3 | AML M2 | M | 66 | IDR/AraC | alive |
| 4 | ALL | F | 71 | ALL202 | alive |
| 5 | AML M2 | M | 64 | IDR/AraC | dead |
| 6 | AML M2 | M | 44 | BMT | alive |
| 7 | AML M3 | M | 49 | | dead |

TABLE 9-continued

| case No. | Diagnosis | sex | Age | Tx | |
|---|---|---|---|---|---|
| 8 | AML M2 | M | 66 | IDR/AraC | alive |
| 9 | AML M4 | F | 43 | IDR/AraC | dead |
| 10 | AML M2 | F | 21 | BMT | dead |
| 11 | AML M4 | M | 64 | BMT | alive |
| 12 | AML M6 | M | 64 | BMT | alive |
| 13 | AML M2 | F | 80 | BSC | dead |

$1\times10^6$ cells of each sample were washed with 0.1% BSA/PBS, and labeled by the reaction for 10 min with 10 μl of antibodies (PE-conjugated CD33 antibody (R&D) and FITC-conjugated Notch-1 antibody (R&D)) in 1 ml of PBS, then the cells were washed with PBS and the cell suspension was prepared. This cell suspension was subjected to FACSCalibur™ flow cytometer (BD Biosiences, San Jose, Calif., USA) to detect positive cells, and they were analyzed by CellQuest Pro software (BD Biosciences). As demonstrated by the results shown in FIG. 41, Notch-1/CD33-positive cells were frequently observed in the acute myeloid leukemia (AML) samples except one sample of acute lymphatic leukemia (ALL). For reference, the ratios of Notch-1 and/or CD33-positive cells in each sample were listed in Table 10 below. In the table, values of 20 or more are enclosed by a rectangle. Here, the samples are listed in the same sequence as in the above Table 9.

TABLE 10

| Diagnosis | CD33 × Notch1 | Notch1 | CD33 |
|---|---|---|---|
| AML M1 | 38.53 | 48.56 | 68.84 |
| AML M2 | 32.83 | 33.64 | 97.13 |
| AML M2 | 24.27 | 54.5 | 33.81 |
| ALL | 1.16 | 11.76 | 14.41 |
| AML M2 | 16.68 | 29.8 | 22.75 |
| AML M2 | 24.13 | 29.34 | 42.26 |
| AML M3 | 10.42 | 16.91 | 15.93 |
| AML M2 | 27.59 | 39.2 | 57.69 |
| AML M4 | 70.54 | 72.51 | 92.54 |
| AML M2 | 12.65 | 26.78 | 19.49 |
| AML M4 | 36.75 | 37.46 | 97.3 |
| AML M6 | 33.87 | 55.73 | 37.81 |
| AML M2 | 7.65 | 15.44 | 37.55 |

Example 31. Effects of Doxorubicin-Encapsulated Fucosylated Liposomes on Various Leukemia Sample Cells Using WST-1 assay, cytotoxic effects of doxorubicin-encapsulated fucosylated liposomes were investigated. $2\times10^4$ cells of each type were seeded in a 96-well culture flask, and the cells were incubated with 0.1 μM or 1.0 μM of doxorubicin alone (DOX), doxorubicin-included fucosylated liposomes (F25) or doxorubicin-included non-fucosylated liposomes (F0). After 2 hr incubation, the cells were washed with PBS, and after replacement of the culture solution (10% FBS-supplemented RPMI1640 medium), further 72 hr of culturing was performed; then an assay using WST-1 reagent was performed similarly to Example 12, and viable cells were counted. As shown in FIG. 42, in the Notch-1 expressing samples (Cases 1 and 2), doxorubicin-included fucosylated liposomes exhibited a significant cytocidal effect compared to doxorubicin alone or doxorubicin-included non-fucosylated liposomes. In contrast, in the Notch-1 non-expressing sample (Case 4), such a significant cytocidal effect was not observed.

The invention claimed is:

1. A combined pharmaceutical preparation comprising a first component consisting of a free mannose or a free compound having terminal mannose and a second component containing a substance selected from the group consisting of a drug that controls the activity or growth of a fucosylated molecule-producing cell, a medicament for treating a disease related to a fucosylated molecule-producing cell, a carrier and a labeling agent,
wherein the substance is targeted by a fucose or a molecule having terminal fucose, and
wherein a mass ratio of mannose to fucose is from 20000:1 to 200:1, or a molar ratio of mannose to fucose is from 16000:1 to 160:1.

2. The pharmaceutical preparation according to claim 1, wherein the first component and the second component are administered simultaneously and/or sequentially.

3. The pharmaceutical preparation according to claim 1, wherein the medicament comprises a drug selected from the group consisting of an anti-inflammatory agent and an antitumor agent.

4. The pharmaceutical preparation according to claim 1, wherein the labeling agent contains a label selected from the group consisting of a gas or a substance that generates a gas under physiological conditions, a radioisotope, a magnetic substance, a nuclear magnetic resonance element, a substance that affects the relaxation time of a nuclear magnetic resonance element, a substance that binds to a labeling substance, a fluorescent substance, a fluorophore, a chemiluminescent substance, an enzyme, biotin or its derivative, avidin or its derivative, or a substance comprising one or more thereof.

5. A kit comprising one or more containers comprising, singly or in combination, a first component consisting of a free mannose or a free compound having terminal mannose and a substance selected from the group consisting of a drug that controls the activity or growth of a fucosylated molecule-producing cell, a medicament for treating a disease related to a fucosylated molecule-producing cell, a carrier and a labeling agent, wherein the substance is targeted by fucose or a molecule having terminal fucose, wherein a mass ratio of mannose to fucose is from 20000:1 to 200:1, or a molar ratio of mannose to fucose is from 16000:1 to 160:1.

6. A method for treating a disease related to a fucosylated molecule-producing cell in a subject in need thereof, comprising administering to the subject an effective amount of the pharmaceutical preparation of claim 1, wherein the pharmaceutical preparation comprises a medicament for treating the disease related to a fucosylated molecule-producing cell.

7. The method according to claim 6, wherein the disease is selected from the group consisting of a neoplastic disease and an inflammatory disease.

8. The method according to claim 7, wherein the neoplastic disease is selected from the group consisting of a solid tumor and leukemia.

9. The method according to claim 6, wherein the fucosylated molecule-producing cell produces a fucosylated molecule selected from the group consisting of CA19-9 and Notch-1.

10. The method according to claim 6, wherein the medicament comprises a drug selected from the group consisting of an anti-inflammatory agent and an antitumor agent.

11. The method according to claim 10, wherein the antitumor agent comprises a platinum complex.

12. A method for controlling an activity or growth of a fucosylated molecule-producing cell in a subject in need thereof, comprising administering to the subject an effective amount of the pharmaceutical preparation of claim 1, wherein the pharmaceutical preparation comprises a drug that controls the activity or growth of a fucosylated molecule-producing cell.

13. A method for specifically delivering a substance to a fucosylated molecule-producing cell in a subject in need thereof, comprising administering to the subject an effective amount of the pharmaceutical preparation of claim 1, wherein the pharmaceutical preparation comprises a carrier.

14. A method for labeling a fucosylated molecule-producing cell or a tissue containing a fucosylated molecule-producing cell in a subject in need thereof, comprising administering to the subject an effective amount of the pharmaceutical preparation of claim 1, wherein the pharmaceutical preparation comprises a labeling agent.

15. A method for detecting a fucosylated molecule-producing cell or a tissue containing a fucosylated molecule-producing cell in a subject in need thereof, comprising administering to the subject an effective amount of the pharmaceutical preparation of claim 1, wherein the pharmaceutical preparation comprises a labeling agent.

16. A method for imaging a fucosylated molecule-producing cell or a tissue containing a fucosylated molecule-producing cell in a subject in need thereof, comprising administering to the subject an effective amount of the pharmaceutical preparation of claim 1, wherein the pharmaceutical preparation comprises a labeling agent.

17. A method for diagnosing, detecting and/or monitoring a disease related to a fucosylated molecule-producing cell in a subject in need thereof, comprising administering to the subject an effective amount of the pharmaceutical preparation of claim 1, wherein the pharmaceutical preparation comprises a labeling agent.

18. A method for evaluating effects of a treatment for a disease related to a fucosylated molecule-producing cell in a subject in need thereof, comprising administering to the subject an effective amount of the pharmaceutical preparation of claim 1, wherein the pharmaceutical preparation comprises a labeling agent.

19. A method for enhancing, in a subject in need thereof, a target specificity of a substance selected from the group consisting of a medicament, a carrier and a labeling agent, which is targeted by fucose or a molecule having terminal fucose carrier, comprising administering to the subject an effective amount of a free mannose or a free compound having terminal mannose, wherein a mass ratio of mannose to fucose is from 20000:1 to 200:1, or a molar ratio of mannose to fucose is from 16000:1 to 160:1.

* * * * *